(12) United States Patent
Nie et al.

(10) Patent No.: US 11,524,970 B2
(45) Date of Patent: Dec. 13, 2022

(54) NITROGEN-CONTAINING COMPOUND, ELECTRONIC ELEMENT, AND ELECTRONIC DEVICE

(71) Applicant: SHAANXI LIGHTE OPTOELECTRONICS MATERIAL CO., LTD., Xi'an (CN)

(72) Inventors: Qiqi Nie, Xi'an (CN); Chao Yu, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/624,170

(22) PCT Filed: Oct. 10, 2020

(86) PCT No.: PCT/CN2020/120243
§ 371 (c)(1),
(2) Date: Dec. 30, 2021

(87) PCT Pub. No.: WO2021/088590
PCT Pub. Date: May 14, 2021

(65) Prior Publication Data
US 2022/0213124 A1 Jul. 7, 2022

(30) Foreign Application Priority Data
Nov. 5, 2019 (CN) .......................... 201911070958.7

(51) Int. Cl.
*C07D 519/00* (2006.01)
*H01L 51/00* (2006.01)
*H01L 51/50* (2006.01)

(52) U.S. Cl.
CPC .......... *C07D 519/00* (2013.01); *H01L 51/006* (2013.01); *H01L 51/0054* (2013.01);
(Continued)

(58) Field of Classification Search
CPC . H01L 51/0085; H01L 51/0072; H01L 51/00; H01L 51/0054; H01L 51/0067;
(Continued)

(56) References Cited

U.S. PATENT DOCUMENTS

| | | | |
|---|---|---|---|
| 2004/0124766 A1* | 7/2004 | Nakagawa | H01L 51/0064 313/506 |
| 2014/0042412 A1* | 2/2014 | Ryu | H01L 51/0052 544/46 |

(Continued)

FOREIGN PATENT DOCUMENTS

| | | |
|---|---|---|
| CN | 106467529 A | 3/2017 |
| CN | 108203417 A | 6/2018 |

(Continued)

OTHER PUBLICATIONS

The World Intellectual Property Organization (WIPO) International Search Report for PCT/CN2020/120243 dated Jan. 11, 2021 7 Pages (with translation).

(Continued)

*Primary Examiner* — Marcos D. Pizarro
*Assistant Examiner* — Quinton A Brasfield
(74) *Attorney, Agent, or Firm* — Anova Law Group, PLLC

(57) ABSTRACT

Provided are a nitrogen-containing compound, an electronic element, and an electronic device, and relates to the technical field of organic materials. The nitrogen-containing compound is shown as formula I, and can reduce the working voltage of an electronic element, improve the efficiency of an OLED, and prolong the service life of an OLED.

(Continued)

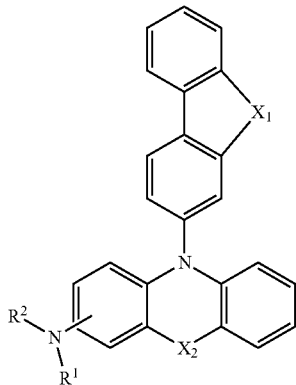

formula I

15 Claims, 2 Drawing Sheets

(52) U.S. Cl.
CPC ...... *H01L 51/0061* (2013.01); *H01L 51/0067* (2013.01); *H01L 51/0072* (2013.01); *H01L 51/0073* (2013.01); *H01L 51/0074* (2013.01); *H01L 51/5056* (2013.01)

(58) Field of Classification Search
CPC ............. H01L 51/0073; H01L 51/0074; H01L 51/006; H01L 51/0061; C07D 519/00
See application file for complete search history.

(56) References Cited

U.S. PATENT DOCUMENTS

2015/0295186 A1* 10/2015 Parham ............... H01L 51/0072
544/339
2015/0318511 A1   11/2015 Kim et al.

FOREIGN PATENT DOCUMENTS

| | | | | |
|---|---|---|---|---|
| CN | 108203428 A | | 6/2018 | |
| CN | 108863896 A | * | 11/2018 | ........... C07D 209/14 |
| CN | 109081783 A | | 12/2018 | |
| CN | 109574996 A | | 4/2019 | |
| CN | 110903260 A | | 3/2020 | |
| WO | 2012141393 A1 | | 10/2012 | |
| WO | 2014017045 A1 | | 1/2014 | |
| WO | 2018159663 A1 | | 9/2018 | |

OTHER PUBLICATIONS

China National Intellectual Property Administration Notification of the first Office Action for CN 201911070958.7 dated Jul. 7, 17, 2020 22 pages (with translation).

* cited by examiner

NITROGEN-CONTAINING COMPOUND, ELECTRONIC ELEMENT, AND ELECTRONIC DEVICE

CROSS REFERENCE TO RELATED APPLICATIONS

The application is a national phase entry under 35 U.S.C. § 371 of International Application No. PCT/CN2020/120243, filed on Oct. 10, 2020, which claims priority to Chinese Patent Application CN 201911070958.7 filed on Nov. 5, 2019, the full content of all of which are incorporated herein by reference in their entirety as part of the present disclosure.

TECHNICAL FIELD

The application relates to the technical field of organic materials, and specifically to a nitrogen-containing compound, an electronic element, and an electronic device.

BACKGROUND

In recent years, with the development of semiconductor technology, electronic elements have been widely used. For example, organic electroluminescent devices (OLEDs) have gradually come into the picture as a new generation of display devices. Compared with traditional display devices, OLEDs show great advantages in voltage characteristics, luminous intensity, luminous efficiency, color quality, response speed, viewing angle, and other aspects, and have low cost. Therefore, OLEDs have promising market prospects.

In order to improve the luminous intensity, efficiency, and service life of OLEDs, a laminated structure is usually used for the OLEDs, which mainly includes: an anode, a cathode, and an organic layer arranged between the cathode and the anode. When a voltage is applied to the cathode and the anode, the two electrodes generate an electric field; and under the action of the electric field, electrons on the cathode side and holes on the anode side move towards a light-emitting layer (EML) at the same time and are combined in the EML to form excitons, and the excitons in an excited state release energy outwards to change from the excited state to a ground state, which results in light emission.

At present, when OLEDs are driven at high temperatures, problems such as increased working voltage, reduced luminous efficiency, and shortened service life may occur, resulting in decreased performance of the OLEDs.

There is also related research in existing technical literatures. For example, Chinese patent CN109081783A provides a symmetrical triarylamine derivative, which can be used to prepare a hole transport layer (HTL) in an OLED. However, in order to further improve the performance of electronic elements, it is still necessary to continue to develop new materials.

SUMMARY

In order to overcome the above-mentioned deficiencies in the art, the disclosure provides a nitrogen-containing compound, an electronic element, and an electronic device, which can reduce the working voltage, increase the luminous efficiency, and prolong the service life of an OLED.

According to one aspect of the disclosure, a nitrogen-containing compound is provided, with a general structural formula shown in formula I:

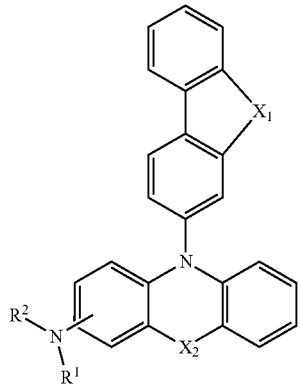

formula I wherein $R^1$ and $R^2$ are the same or different, and are each independently selected from the group consisting of substituted or unsubstituted alkyl with 1 to 20 carbon atoms, substituted or unsubstituted cycloalkyl with 3 to 20 carbon atoms, substituted or unsubstituted heterocycloalkyl with 2 to 20 carbon atoms, substituted or unsubstituted aralkyl with 7 to 40 carbon atoms, substituted or unsubstituted heteroaralkyl with 2 to 40 carbon atoms, substituted or unsubstituted aryl with 6 to 30 carbon atoms, and substituted or unsubstituted heteroaryl with 1 to 30 carbon atoms;

$X_1$ is independently selected from: O and S;

$X_2$ is independently selected from; $CR^3R^4$, $NR^5$, O, and S;

each of $R^3$ and $R^4$ is independently selected from the group consisting of hydrogen, substituted or unsubstituted alkyl with 1 to 20 carbon atoms, substituted or unsubstituted aryl with 6 to 30 carbon atoms, and substituted or unsubstituted heteroaryl with 1 to 30 carbon atoms;

or, $R^3$ and $R^4$ are linked to each other, $R^3$, $R^4$, and carbon atoms being linked to $R^3$ and $R^4$ form a ring system; the ring system is selected from the group consisting of substituted or unsubstituted aryl with 6 to 30 carbon atoms, and substituted or unsubstituted heteroaryl with 1 to 30 carbon atoms;

each of $R^5$ is independently selected from the group consisting of hydrogen, substituted or unsubstituted alkyl with 1 to 20 carbon atoms, substituted or unsubstituted aryl with 6 to 30 carbon atoms, and substituted or unsubstituted heteroaryl with 1 to 30 carbon atoms;

substituents of $R^1$, substituents of $R^2$, substituents of $R^3$, substituents of $R^4$, and substituents of $R^5$ are the same or different, and are each independently selected from the group consisting of deuterium, alkyl with 1 to 10 carbon atoms, cycloalkyl with 3 to 20 carbon atoms, aryl with 6 to 30 carbon atoms, heteroaryl with 1 to 30 carbon atoms, alkoxy with 1 to 10 carbon atoms, and alkylamino with 1 to 40 carbon atoms.

According to one aspect of the disclosure, an electronic element is provided, including an anode and a cathode that are arranged oppositely, and a functional layer arranged between the anode and the cathode, wherein the functional layer includes the nitrogen-containing compound described above.

According to one aspect of the disclosure, an electronic device is provided, including the electronic element described above.

In the nitrogen-containing compound, the electronic element, and the electronic device of the disclosure, a dibenzo-five-membered ring is combined with a naphthazinyl to serve as a core structure. Because naphthazinyl has a strong electron-donating ability and a large conjugated system and can increase electron density of the entire conjugated system, the core structure can enhance the electronic tolerance of the material and can also improve the efficiency and service life of the OLED. The combination of the electron-rich naphthazinyl and the rigid dibenzo-five-membered ring reduces the steric hindrance of an arylamine structure (to reduce an angle of twist between molecules), enables a large planar structure for the conjugated system (to further reduce an energy band width of the compound), and can effectively increase the hole mobility of the material (to promote the hole transport), such that the number of holes and the number of electrons are balanced and the electrons and holes are effectively combined to further improve the efficiency of the OLED.

It should be understood that the above general description and the following detailed description are only exemplary and explanatory, and should not be construed as a limitation to the disclosure.

BRIEF DESCRIPTION OF THE DRAWINGS

The accompanying drawings, which are incorporated in and constitute a part of this description, illustrate the examples of the disclosure, and together with the description, serve to explain the principles of the disclosure. Apparently, the accompanying drawings in the following description show merely some examples of the disclosure, and other drawings may be derived from these accompanying drawings by a person of ordinary skill in the art without creative efforts.

Figure 1:
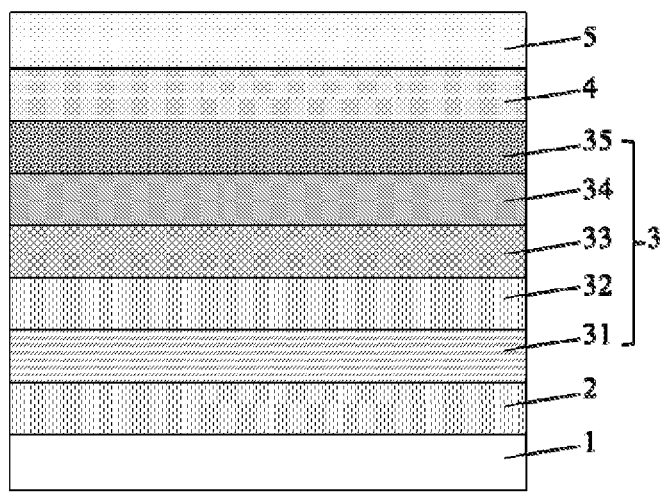
FIG. 1 is a schematic structure diagram of an OLED according to an embodiment of the disclosure.

In the figures: 1. anode; 2. hole injection layer (HIL); 3. functional layer; 31. hole transport layer (HTL); 32. electron blocking layer (EBL); 33. electroluminescent layer (EML); 34. hole blocking layer (HBL); 35. electron transport layer (ETL); 4. electron injection layer (EIL); 5. cathode; 100. substrate; 200. anode; 300. functional layer; 301. hole transport layer (HTL); 302. photosensitive active layer; 303. electron transport layer (ETL); 400. cathode; and 500. electronic device.

DETAILED DESCRIPTION

Exemplary embodiments will be described below comprehensively with reference to the accompanying drawings. However, the exemplary embodiments can be implemented in various forms and should not be construed as being limited to examples described herein. On the contrary, these embodiments are provided such that the disclosure is comprehensive and complete and the concept of the exemplary embodiments is fully conveyed to persons skilled in the art. The described features, structures, or characteristics are incorporated into one or more embodiments in any suitable manner. In the following description, many specific details are provided to give a full understanding of the embodiments of the disclosure.

The terms "a" and "the" are used to indicate that there are one or more elements, components, and the like. The terms "include" and "have" are used to indicate open-ended inclusion, which mean that there may be additional elements, components, and the like in addition to the listed elements, components, and the like. The description manners used in the disclosure such as "each of . . . is independently", " . . . is respectively and independently" and " . . . is(are) each independently selected from the group consisting of" can be used interchangeably, and should be understood in a broad sense, which can mean that, in different groups, specific options expressed by the same symbols do not affect each other, or in the same group, specific options expressed by the same symbols do not affect each other. For example, "

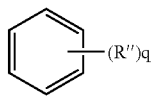

formula Q-1

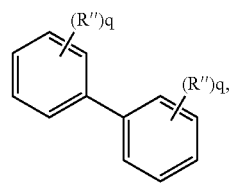

formula Q-2 wherein q is independently 0, 1, 2, or 3, and substituents R" are each independently selected from the group consisting of hydrogen, fluorine, and chlorine" means that, in formula Q-1, there are q substituents R" on the benzene ring, the substituents R" can be the same or different, and options for each substituent R" do not affect each other; and in formula Q-2, there are q substituents R" on each benzene ring of the biphenyl, the numbers q of substituents R" on the two benzene rings can be the same or different, the substituents R" can be the same or different, and options for each substituent R" do not affect each other.

In the disclosure, the halogen to serve as a substituent includes fluorine, chlorine, bromine, or iodine.

"Alkyl" is saturated linear or branched monovalent hydrocarbyl, and a group formed from alkyl is optionally substituted by one or more substituents. The alkyl in the disclosure may include 1 to 20 carbon atoms. In some embodiments, the alkyl may include 1 to 10 carbon atoms; in other embodiments, the alkyl may include 1 to 6 carbon atoms; and in still other embodiments, the alkyl may include 1 to 4 carbon atoms. For example, the number of carbon atoms in an alkyl group can be 1, 3, 4, 6, 8, or 10 carbon atoms. Of course, there can be any other number of carbon atoms, which will not be listed here. The alkyl may be optionally substituted by one or more substituents. For example, the alkyl may include: methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), and the like. However, these examples are provided merely for illustration, and are not intended to limit the disclosure.

The "aryl" can be a monocyclic structure formed by multiple carbon atoms, or can be a bicyclic or polycyclic system formed by carbon atoms, where there may be at least one aromatic ring system and each ring system may include a ring formed by 3 to 7 atoms. The terms "aryl" and "aromatic ring" can be used interchangeably. The aryl in the disclosure is include 6 to 30 carbon atoms. In some embodiments, the aryl may include 6 to 20 carbon atoms; in other embodiments, the aryl may include 6 to 18 carbon atoms; and in still other embodiments, the aryl may include 6 to 14 carbon atoms. For example, there can be 6, 12, 18, 20, 24, or 30 carbon atoms in the aryl. Of course, there can be any other number of carbon atoms, which will not be listed here. The aryl may refer to a monocyclic aryl group or a polycyclic aryl group. In other words, the aryl may refer a monocyclic aryl group, a fused-ring aryl group, two or more monocyclic aryl groups conjugated through carbon-carbon bonds, a monocyclic aryl group and a fused-ring aryl group conjugated through carbon-carbon bonds, and two or more fused-ring aryl groups conjugated through carbon-carbon bonds. That is, two or more aromatic groups conjugated through carbon-carbon bonds can also be regarded as the aryl of the disclosure. For example, the aryl includes phenyl, naphthyl, anthracenyl, fluorenyl, phenanthryl, indenyl, biphenyl, terphenyl, pyrenyl, perylenyl, chrysenyl, fluoranthenyl, and the like. However, these examples are provided merely for illustration, and are not intended to limit the disclosure.

It should be noted that the aryl can be independently optionally substituted by one or more substituents. In the disclosure, substituted aryl refers to aryl in which one or more hydrogen atoms are substituted by other groups. For example, at least one hydrogen atom is substituted by deuterium, F, Cl, I, CN, hydroxyl, nitro, amino, branched alkyl, linear alkyl, cycloalkyl, aryl, or heteroaryl. It should be appreciated that substituted aryl with 6 to 30 carbon atoms means that the total number of carbon atoms of the aryl and carbon atoms of substituents on the aryl is 6 to 30. The substituted or unsubstituted aryl can include 6 to 30, 6 to 20, 6 to 18, 6 to 15, or 6 to 14 carbon atoms, but is not limited thereto.

In the disclosure, aryl with 6 to 20 ring-forming carbon atoms means that the number of carbon atoms on an aromatic ring in the aryl is 6 to 20, which excludes the number of carbon atoms in substituents on the aryl. The aryl can include 6 to 20, 6 to 18, 6 to 14, or 6 to 10 ring-forming carbon atoms, but is not limited thereto.

The "aryl" can be attached to the remaining part of the molecule through one or more attachment points. When two single bonds in the aryl are attached to the remaining part of the molecule, the aryl is arylene.

In the disclosure, aryl with 6 to 14 carbon atoms to serve as a substituent includes, but is not limited to, phenyl, naphthyl, biphenyl, fluorenyl, dimethylfluorenyl, anthracenyl, and phenanthryl.

The term "heteroaryl" refers to a ring system with at least one aromatic ring, which can be a monocyclic, bicyclic, or polycyclic system formed by various atoms, where at least one aromatic system includes one or more heteroatoms selected from the group consisting of B, O, S, N, Si, and P and each ring system can include a ring consisting of 5 to 7 atoms. The terms "heteroaryl", "heteroaromatic ring", and "heteroaromatic compound" can be used interchangeably. The heteroaryl in the disclosure includes 1 to 30 carbon atoms. In some embodiments, the heteroaryl may include 1 to 20 carbon atoms; in other embodiments, the heteroaryl may include 4 to 20 carbon atoms; and in still other embodiments, the heteroaryl may include 5 to 12 carbon atoms. For example, there can be 1, 4, 5, 6, 12, 18, 20, 24, or 30 carbon atoms in the heteroaryl. Of course, there can be any other number of carbon atoms in the heteroaryl, which will not be listed here. The heteroaryl may be optionally substituted by one or more substituents. For example, monocyclic heteroaryl may include: furyl, imidazolyl, isoxazolyl, pyrrolyl, pyridyl, pyrimidinyl, pyridazinyl, thiazolyl, thienyl, pyrazolyl, isothiazolyl, pyrazinyl, triazinyl, and the like; bicyclic heteroaryl may include benzimidazolyl, benzofuranyl, benzothienyl, indolyl, purinyl, quinolinyl, isoquinolinyl, naphthyridinyl, and the like; and tricyclic heteroaryl may include dibenzofuranyl, dibenzothienyl, carbazolyl, phenanthrolinyl, acridinyl, and the like. Of course, the heteroaryl may also include other groups, which is not specifically limited here.

In the disclosure, substituted heteroaryl refers to heteroaryl in which one or more hydrogen atoms are substituted by other groups. For example, at least one hydrogen atom is substituted by deuterium, F, Cl, I, CN, amino, branched alkyl, linear alkyl, cycloalkyl, alkoxy, alkylamino, aryl, heteroaryl, or the like. It should be interpreted that substituted heteroaryl with 1 to 30 carbon atoms means that the total number of carbon atoms of the heteroaryl and carbon atoms of substituents on the heteroaryl is 1 to 30. The substituted heteroaryl can include 1 to 30, 1 to 20, 3 to 20, 4 to 20, 5 to 18, or 5 to 12 carbon atoms, but is not limited thereto.

In the disclosure, heteroaryl with 5 to 12 carbon atoms to serve as a substituent includes, but is not limited to, pyridyl, indolyl, quinolinyl, phenanthrolinyl, dibenzofuranyl, dibenzothienyl, and carbazolyl.

In the disclosure, heteroaryl with 1 to 20 ring-forming carbon atoms means that the number of carbon atoms on a heteroaromatic ring in the heteroaryl is 1 to 20, which excludes the number of carbon atoms in substituents on the heteroaryl.

The "heteroaryl" can be attached to the remaining part of the molecule through one or more attachment points. When two single bonds in the heteroaryl are attached to the remaining part of the molecule, the heteroaryl is heteroarylene.

For example,

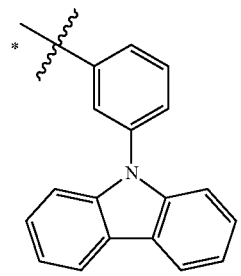 [SMILES: *c1cccc(-n2c3ccccc3c3ccccc32)c1]

is carbazolyl-substituted phenyl, which belongs to substituted aryl with 6 ring-forming carbon atoms and also belongs to substituted aryl with 18 carbon atoms; and

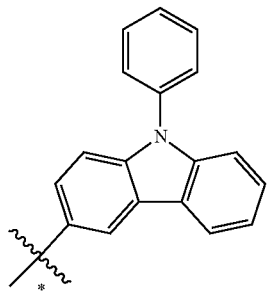 [SMILES: *c1ccc2c(c1)c1ccccc1n2-c1ccccc1]

is phenyl-substituted carbazolyl, which belongs to substituted heteroaryl with 12 ring-forming carbon atoms and also belongs to substituted heteroaryl with 18 carbon atoms.

An embodiment of the disclosure provides a nitrogen-containing compound, with a general structural formula shown in formula I:

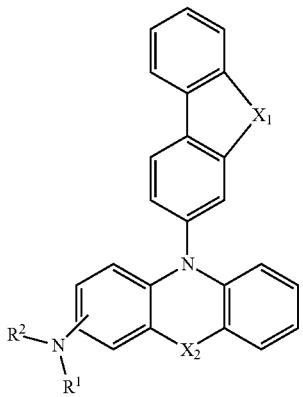

formula I wherein $R^1$ and $R^2$ are the same or different, and are each independently selected from the group consisting of substituted or unsubstituted alkyl with 1 to 20 carbon atoms, substituted or unsubstituted cycloalkyl with 3 to 20 carbon atoms, substituted or unsubstituted heterocycloalkyl with 2 to 20 carbon atoms, substituted or unsubstituted aralkyl with 7 to 40 carbon atoms, substituted or unsubstituted heteroaralkyl with 2 to 40 carbon atoms, substituted or unsubstituted aryl with 6 to 30 carbon atoms, and substituted or unsubstituted heteroaryl with 1 to 30 carbon atoms;

$X_1$ is independently selected from: O and S;

$X_2$ is independently selected from: $CR^3R^4$, $NR^5$, O, and S;

each of $R^3$ and $R^4$ is independently selected from the group consisting of hydrogen, substituted or unsubstituted alkyl with 1 to 20 carbon atoms, substituted or unsubstituted aryl with 6 to 30 carbon atoms, and substituted or unsubstituted heteroaryl with 1 to 30 carbon atoms;

or, $R^3$ and $R^4$ are linked to each other, $R^3$, $R^4$, and carbon atoms being linked to $R^3$ and $R^4$ form a ring system, the ring system is selected from the group consisting of substituted or unsubstituted aryl with 6 to 30 carbon atoms and substituted or unsubstituted heteroaryl with 1 to 30 carbon atoms;

each of $R^5$ is independently selected from the group consisting of hydrogen, substituted or unsubstituted alkyl with 1 to 20 carbon atoms, substituted or unsubstituted aryl with 6 to 30 carbon atoms, and substituted or unsubstituted heteroaryl with 1 to 30 carbon atoms;

substituents of $R^1$, substituents of $R^2$, substituents of $R^3$, substituents of $R^4$, and substituents of $R^5$ are the same or different, and are each independently selected from the group consisting of deuterium, alkyl with 1 to 10 carbon atoms, cycloalkyl with 3 to 20 carbon atoms, aryl with 6 to 30 carbon atoms, heteroaryl with 1 to 30 carbon atoms, alkoxy with 1 to 10 carbon atoms, and alkylamino with 1 to 40 carbon atoms.

In the nitrogen-containing compound, the electronic element, and the electronic device of the disclosure, a dibenzo-five-membered ring is combined with a naphthazinyl to serve as a core structure. Because a naphthazinyl has strong electron-donating ability and a large conjugated system and can increase an electron density of the entire conjugated system, the core structure can enhance the electronic tolerance of the material and can also improve the efficiency and service life of the OLED. The combination of the electron-rich naphthazinyl and the rigid dibenzo-five-membered ring reduces the steric hindrance of an arylamine structure (to reduce an angle of twist between molecules), enables a large planar structure for the conjugated system (to further reduce an energy band width of the compound), and can effectively increase the hole mobility of the material (to promote the hole transport), such that the number of holes and the number of electrons are balanced and the electrons and holes are effectively combined to further improve the efficiency of the OLED.

Each part of the nitrogen-containing compound of the embodiment of the disclosure is described in detail below:

The nitrogen-containing compound of the disclosure has a general structural formula shown in formula I:

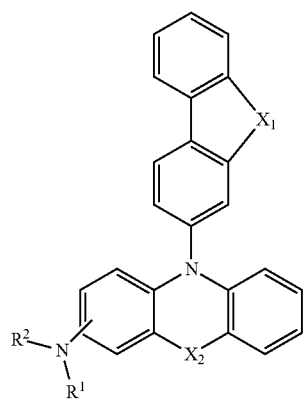

formula I $R^1$ and $R^2$ are the same or different, and are each independently selected from the group consisting of substituted or unsubstituted alkyl with 1 to 20 carbon atoms, substituted or unsubstituted cycloalkyl with 3 to 20 carbon atoms, substituted or unsubstituted heterocycloalkyl with 2 to 20 carbon atoms, substituted or unsubstituted aralkyl with 7 to 40 carbon atoms, substituted or unsubstituted heteroaralkyl with 2 to 40 carbon atoms, substituted or unsubstituted aryl with 6 to 30 carbon atoms, and substituted or unsubstituted heteroaryl with 1 to 30 carbon atoms.

The "hetero" means that a functional group includes at least one heteroatom selected from the group consisting of B, P, N, O, S, Si and Ge, and the rest atoms are carbon. The "substituted" means that at least one hydrogen atom in $R^1$ and $R^2$ is substituted by a substituent.

In some embodiments, $R^1$ and $R^2$ are each independently selected from the group consisting of substituted or unsubstituted aryl with 6 to 20 carbon atoms, and substituted or unsubstituted heteroaryl with 4 to 20 carbon atoms. For example, there can be 6, 10, 12, 13, 14, 16, 18, or 20 carbon atoms in the substituted or unsubstituted aryl. Of course, there can be any other number of carbon atoms, which will not be listed here. For example, there can be 4, 5, 10, 12, 13, 14, 16, 18, or 20 carbon atoms in the substituted or unsubstituted heteroaryl. Of course, there can be any other number of carbon atoms, which will not be listed here.

Substituents of R' and substituents of $R^2$ are the same or different, and the substituents are each independently selected from the group consisting of deuterium, alkyl with 1 to 10 carbon atoms, cycloalkyl with 3 to 20 carbon atoms, aryl with 6 to 30 carbon atoms, heteroaryl with 1 to 30 carbon atoms, alkoxy with 1 to 10 carbon atoms, and alkylamino with 1 to 40 carbon atoms.

In some more specific embodiments, $R^1$ and $R^2$ are each independently selected from the group consisting of substituted or unsubstituted aryl with 6 to 18 ring-forming carbon atoms, and substituted or unsubstituted heteroaryl with 5 to 12 ring-forming carbon atoms; and substituents of $R^1$ and substituents of $R^2$ are each independently selected from the group consisting of deuterium, alkyl with 1 to 4 carbon atoms, aryl with 6 to 14 carbon atoms, and heteroaryl with 5 to 12 carbon atoms.

In some embodiments, $R^1$ and $R^2$ are each independently selected from the group consisting of substituted or unsubstituted aryl with 6 to 14 ring-forming carbon atoms, and substituted or unsubstituted heteroaryl with 5 to 12 ring-forming carbon atoms.

In some more specific embodiments, $R^1$ and $R^2$ are each independently selected from the group consisting of substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted anthracenyl, substituted or unsubstituted phenanthryl, substituted or unsubstituted pyrenyl, substituted or unsubstituted perylenyl, substituted or unsubstituted pyridyl, substituted or unsubstituted quinolinyl, substituted or unsubstituted indolyl, substituted or unsubstituted dibenzothienyl, substituted or unsubstituted dibenzofuranyl, substituted or unsubstituted carbazolyl, and substituted or unsubstituted phenanthrolinyl. In some more specific embodiments, substituents of R' and substituents of $R^2$ may be the same or different, and are each independently selected from the group consisting of deuterium, methyl, ethyl, isopropyl, tert-butyl, phenyl, naphthyl, biphenyl, anthracenyl, phenanthryl, pyridyl, dibenzothienyl, dibenzofuranyl, and carbazolyl.

For example, there can be 6, 10, 12, 13, 14, 16, or 18 ring-forming carbon atoms in the aryl. Of course, there can be any other number of ring-forming carbon atoms, which will not be listed here. Aryl with 6 to 14 ring-forming carbon atoms, includes, but is not limited to, phenyl (with 6 ring-forming carbon atoms), naphthyl (with 10 ring-forming carbon atoms), anthracenyl (with 14 ring-forming carbon atoms), phenanthryl (with 14 ring-forming carbon atoms), and fluorenyl (with 13 ring-forming carbon atoms).

There can be 5, 8, 10, or 12 ring-forming carbon atoms in the heteroaryl. Heteroaryl with 5 to 12 ring-forming carbon atoms includes, but is not limited to, pyridyl (with 5 ring-forming carbon atoms), quinolinyl (with 9 ring-forming carbon atoms), dibenzothienyl (with 12 ring-forming carbon atoms), dibenzofuranyl (with 12 ring-forming carbon atoms), and carbazolyl (with 12 ring-forming carbon atoms).

For example, $R^1$ and $R^2$ may be the same or different, and $R^1$ and $R^2$ are each independently selected from the group consisting of the following groups:

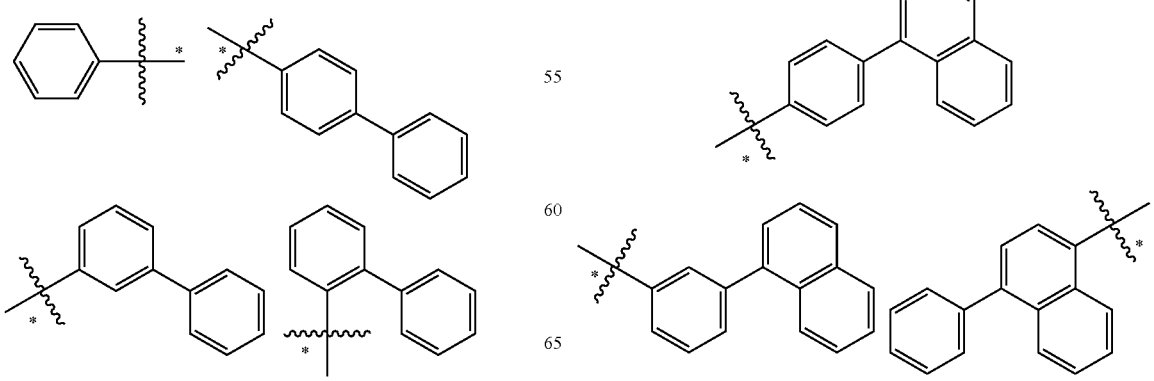

-continued

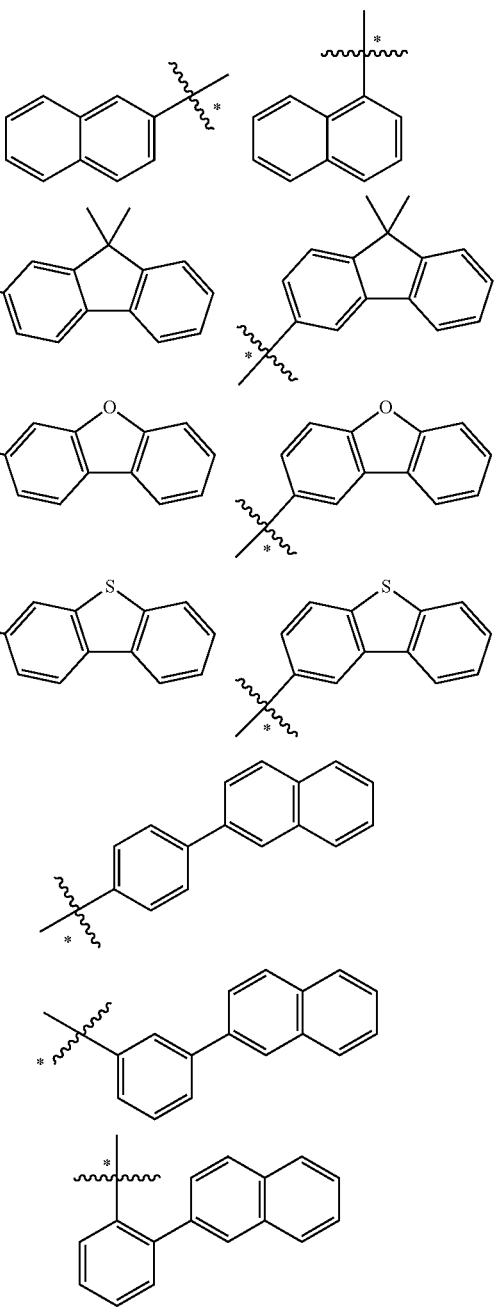

-continued

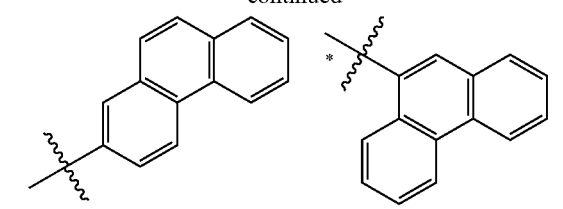
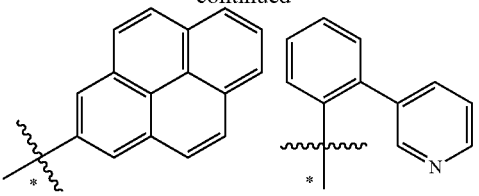
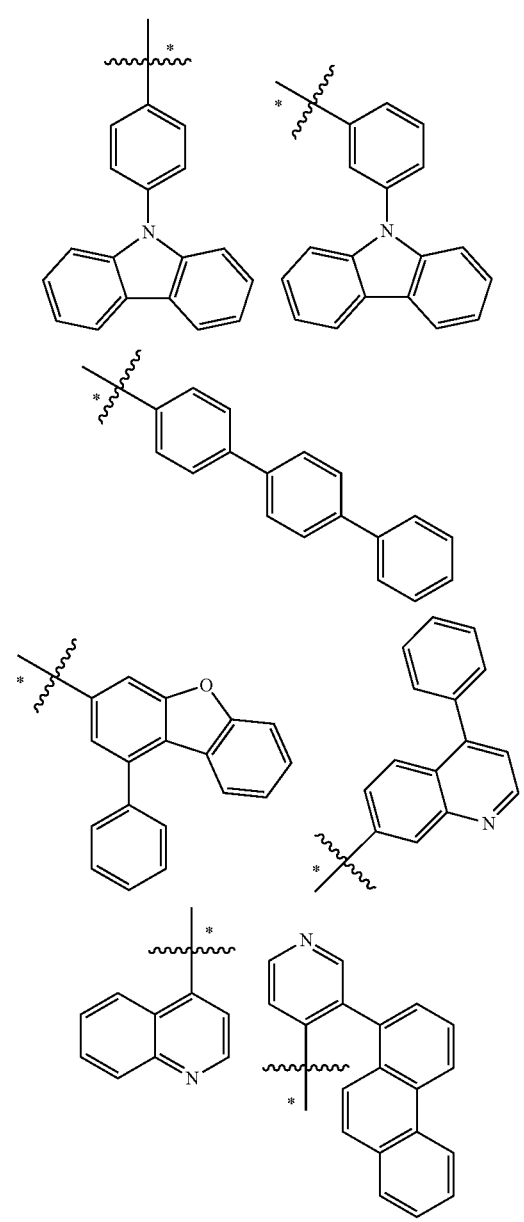
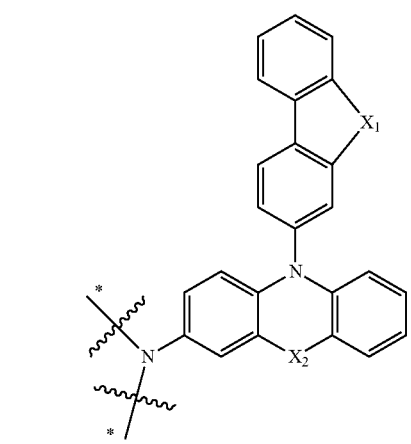

wherein * means a position where the above group is intended to link to in formula I.

$X_2$ is independently selected from the group consisting of $CR^3R^4$, $NR^5$, O, and S, wherein $R^3$ and $R^4$ are substituents attached to a carbon atom, $R^5$ is a substituent attached to a nitrogen atom, and $R^3$ and $R^4$ are each independently selected from the group consisting of hydrogen, substituted or unsubstituted alkyl with 1 to 20 carbon atoms, substituted or unsubstituted aryl with 6 to 30 carbon atoms, and substituted or unsubstituted heteroaryl with 1 to 30 carbon atoms; or, $R^3$ and $R^4$ are linked to each other, $R^3$, $R^4$, and carbon atoms being linked to $R^3$ and $R^4$ form a ring system, the ring system is selected from the group consisting of substituted or unsubstituted aryl with 6 to 30 carbon atoms, and substituted or unsubstituted heteroaryl with 1 to 30 carbon atoms.

Each of $R^5$ is independently selected from the group consisting of hydrogen, substituted or unsubstituted alkyl with 1 to 20 carbon atoms, substituted or unsubstituted aryl with 6 to 30 carbon atoms, and substituted or unsubstituted heteroaryl with 1 to 30 carbon atoms.

Substituents of $R^3$, substituents of $R^4$, and substituents of $R^5$ are the same or different, and the substituents are each independently selected from the group consisting of deuterium, alkyl with 1 to 10 carbon atoms, cycloalkyl with 3 to 20 carbon atoms, aryl with 6 to 30 carbon atoms, heteroaryl with 1 to 30 carbon atoms, alkoxy with 1 to 10 carbon atoms, and alkylamino with 1 to 40 carbon atoms.

In some embodiments, $X_2$ may be independently selected from the group consisting of $CR^3R^4$, $NR^5$, O, and S, wherein $R^3$ and $R^4$ are each independently selected from the group consisting of hydrogen, substituted or unsubstituted alkyl with 1 to 10 carbon atoms, substituted or unsubstituted aryl with 6 to 14 carbon atoms, and substituted or unsubstituted heteroaryl with 1 to 12 carbon atoms; or, $R^3$ and $R^4$ are linked to each other, $R^3$, $R^4$, and carbon atoms being linked to $R^3$ and $R^4$ form a ring system, the ring system is selected from the group consisting of substituted or unsubstituted aryl with 6 to 20 carbon atoms, and substituted or unsubstituted heteroaryl with 4 to 20 carbon atoms; and each of $R^5$ is selected from the group consisting of hydrogen, substituted or unsubstituted alkyl with 1 to 10 carbon atoms, substituted or unsubstituted aryl with 6 to 20 carbon atoms, and substituted or unsubstituted heteroaryl with 4 to 20 carbon atoms.

In some more specific embodiments, $X_2$ may be selected from: O, S, and $CR^3R^4$, wherein $R^3$ and $R^4$ are each independently selected from the group consisting of hydrogen, methyl, ethyl, propyl, isopropyl, butyl, isobutyl, tert-butyl, and phenyl.

In some more specific embodiments, substituents of IV, substituents of $R^2$, substituents of $R^3$, substituents of $R^4$, and substituents of $R^5$ may be the same or different, and are each independently selected from the group consisting of deuterium, alkyl with 1 to 4 carbon atoms, aryl with 6 to 14 carbon atoms, and heteroaryl with 5 to 12 carbon atoms. In some more specific embodiments, substituents of $R^1$, substituents of $R^2$, substituents of $R^3$, substituents of $R^4$, and substituents of $R^5$ may be the same or different, and the substituents are each independently selected from the group consisting of deuterium, methyl, ethyl, propyl, isopropyl, butyl, tert-butyl, phenyl, dibenzofuranyl, and dibenzothienyl.

It should be noted that 1, 2, 3, 4, or 5 in $R^1$, $R^2$, $R^3$, $R^4$, or $R^5$ are only used as marks, and are not intended to limit the number of the substituent.

For example, the nitrogen-containing compound shown in formula I can be selected from the group consisting of the following compounds:

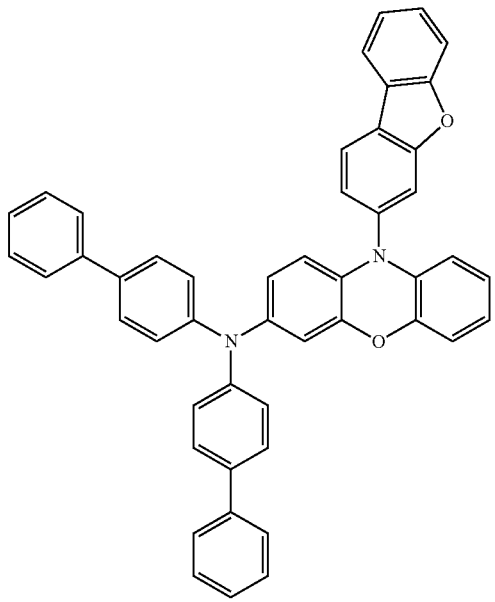

2

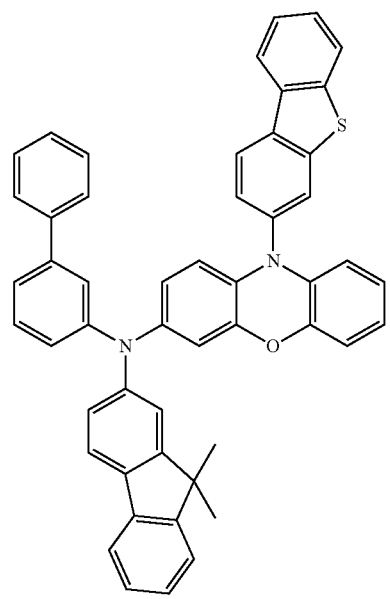

3

9
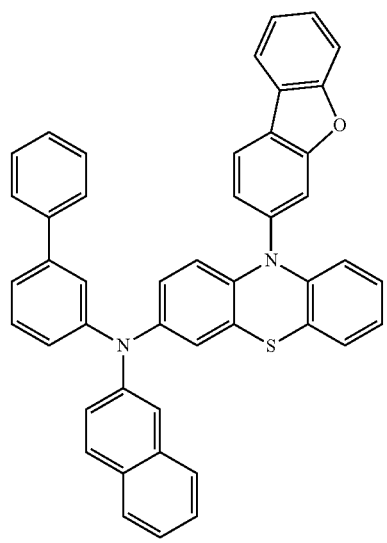
10
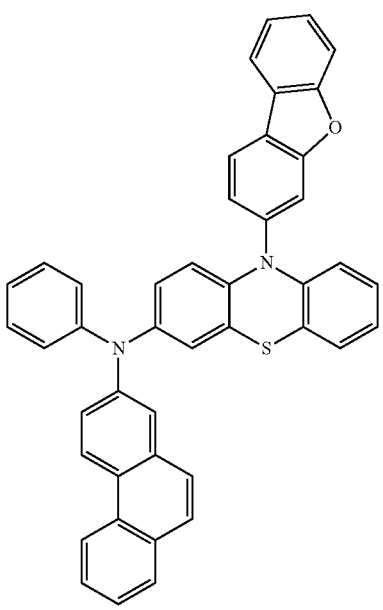
11
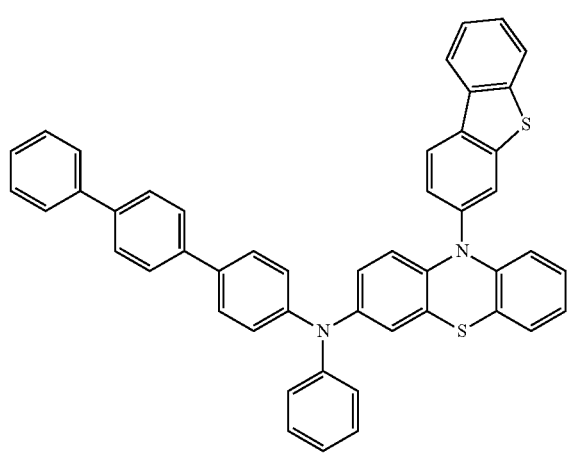
14
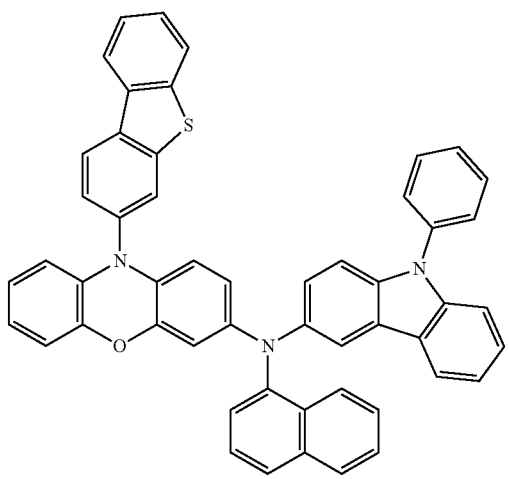 [SMILES: c1ccc(-n2c3ccccc3c3cc(N(c4ccc5c(c4)Oc4ccccc4N5c4ccc5c(c4)sc4ccccc45)c4cccc5ccccc45)ccc32)cc1]
16
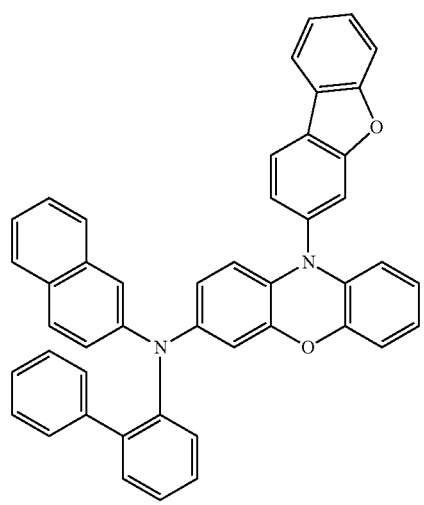 [SMILES: c1ccc(-c2ccccc2N(c2ccc3c(c2)Oc2ccccc2N3c2ccc3c(c2)oc2ccccc23)c2ccc3ccccc3c2)cc1]
17
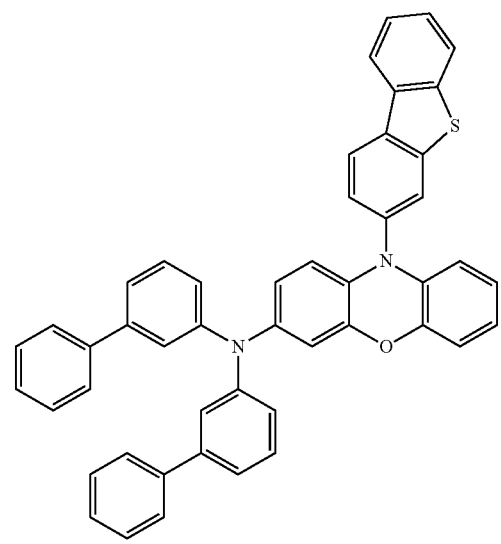

18
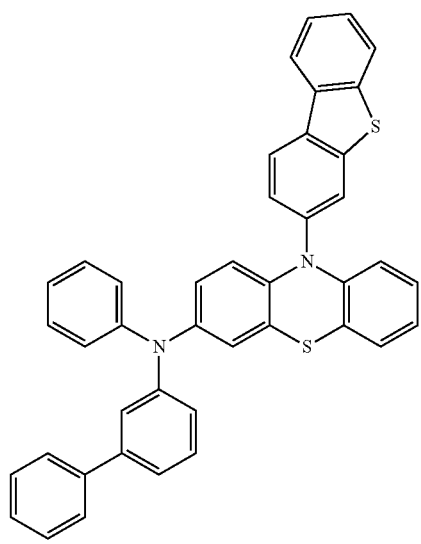
104
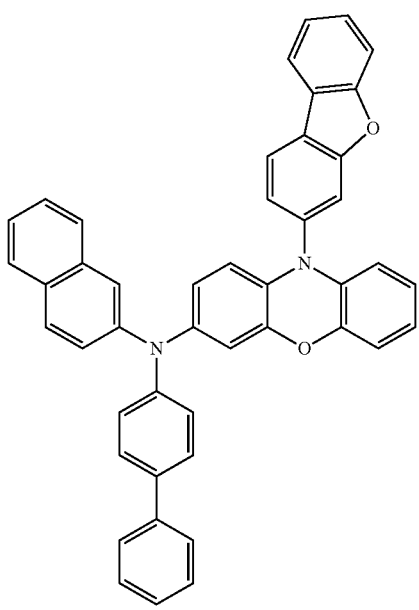
19
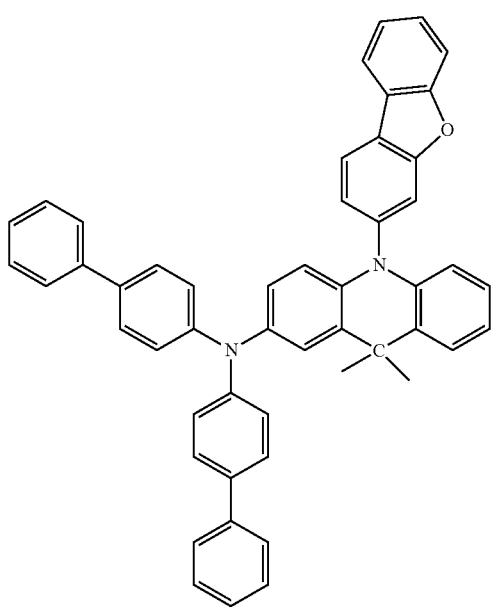
105
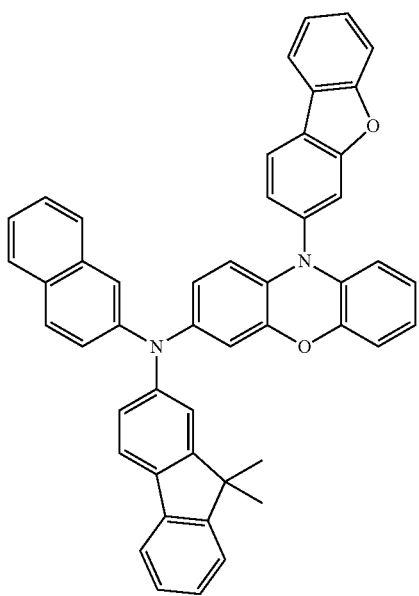

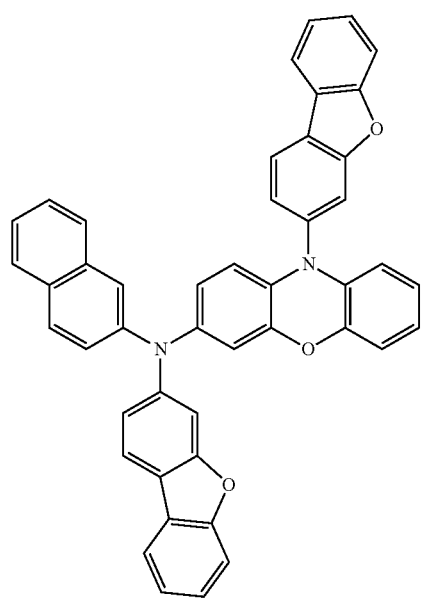
106
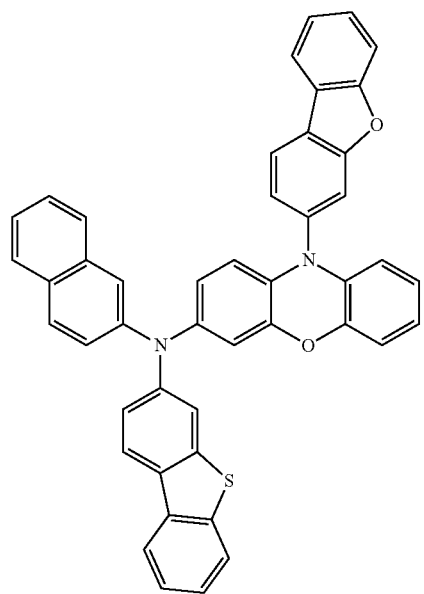
107
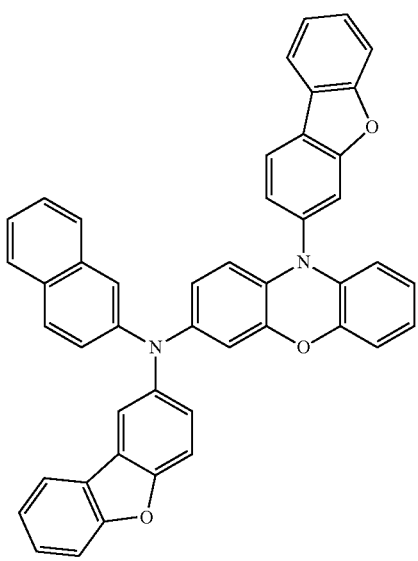
108
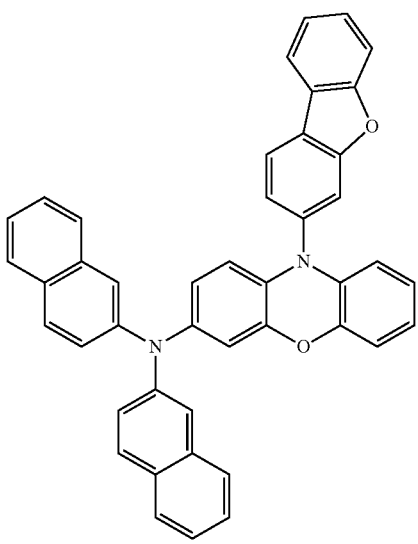
109
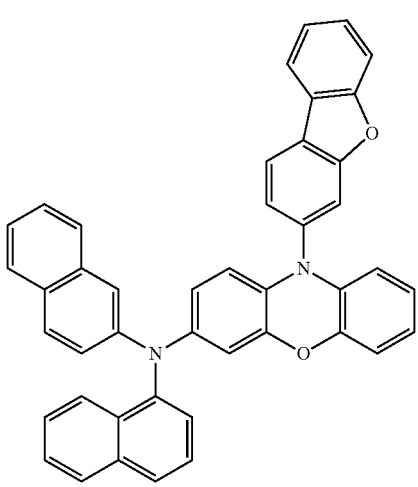
110

111
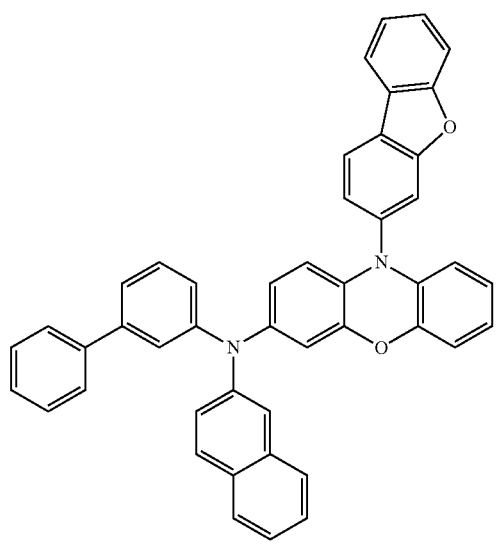
112
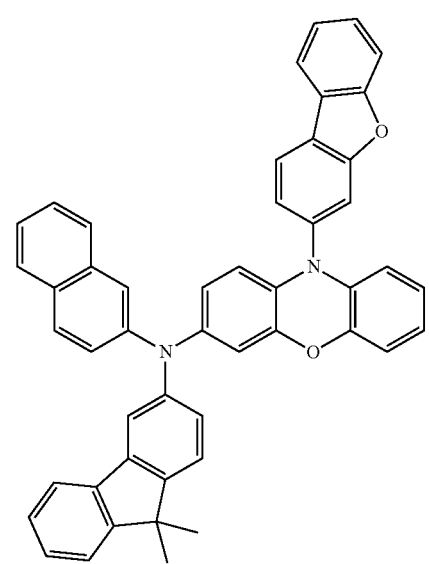
113
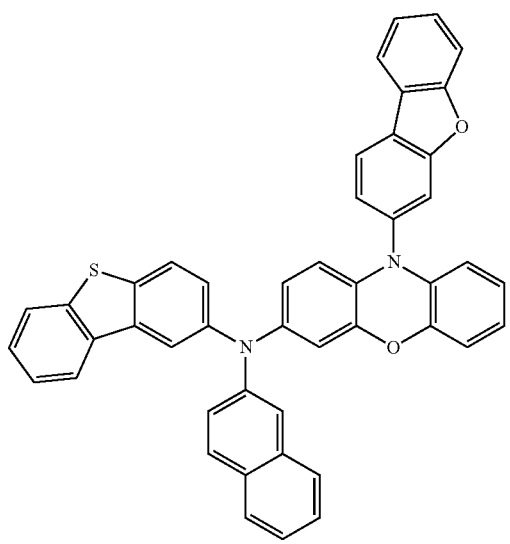
114
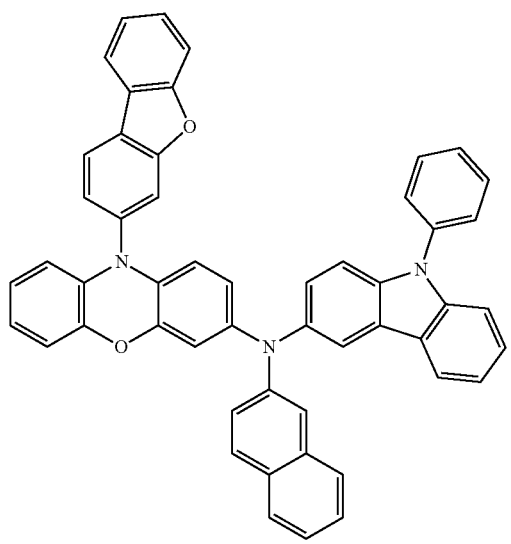
115
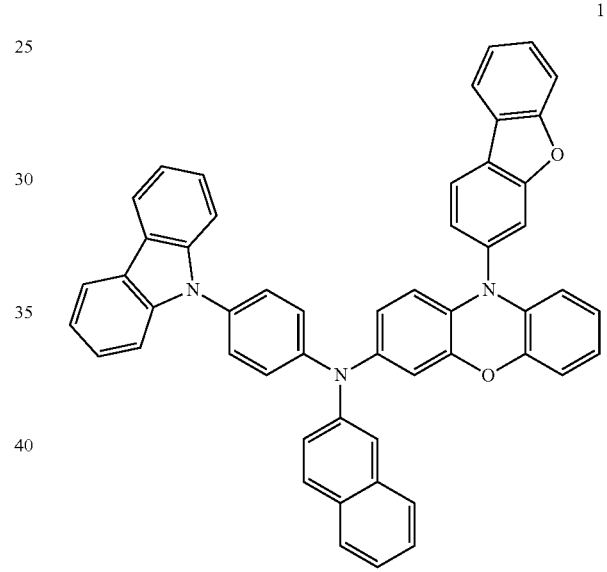
116
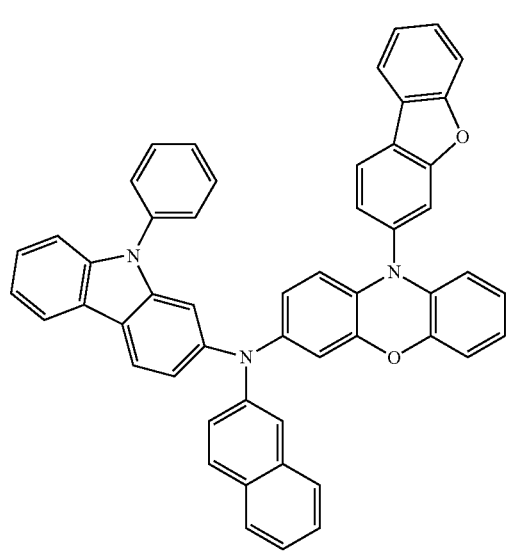

117
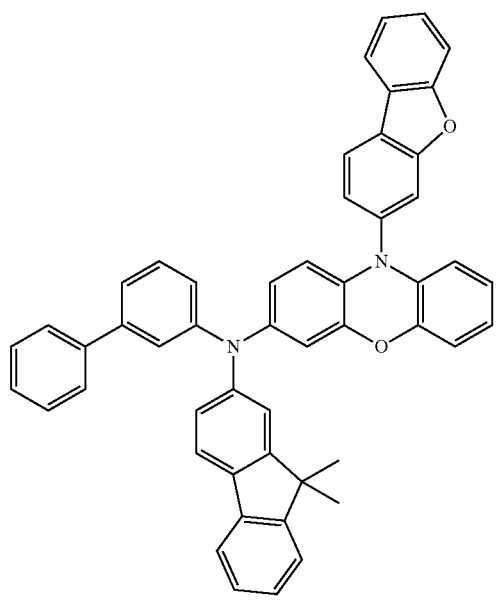
118
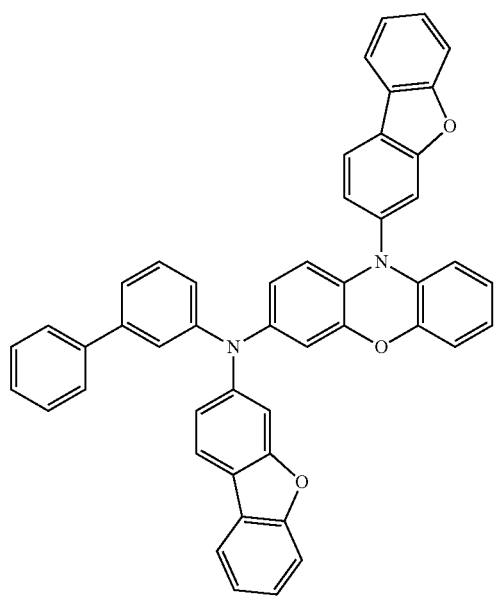
119
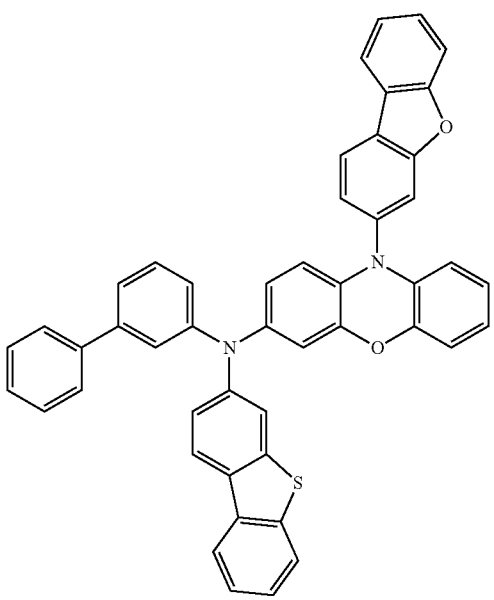
120
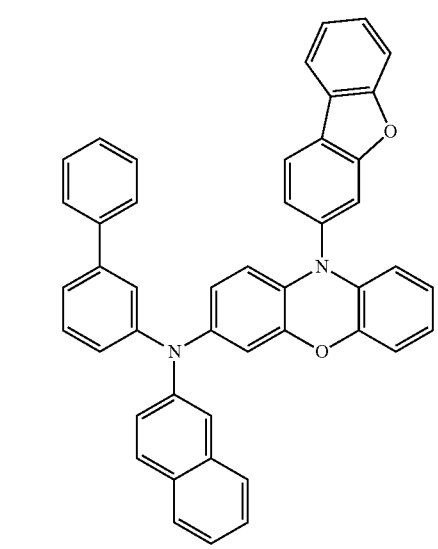
121
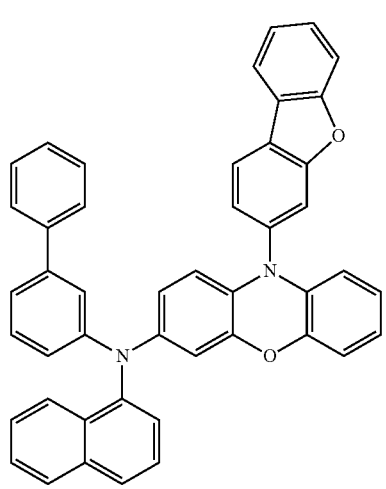

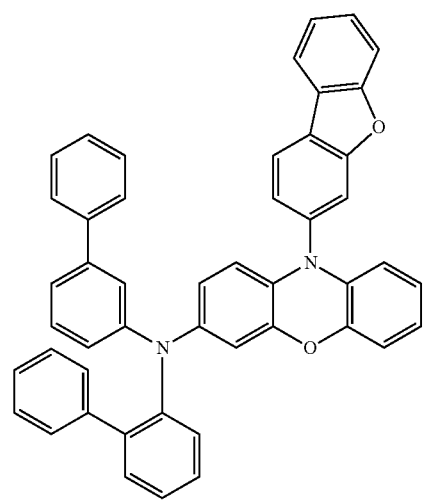
122
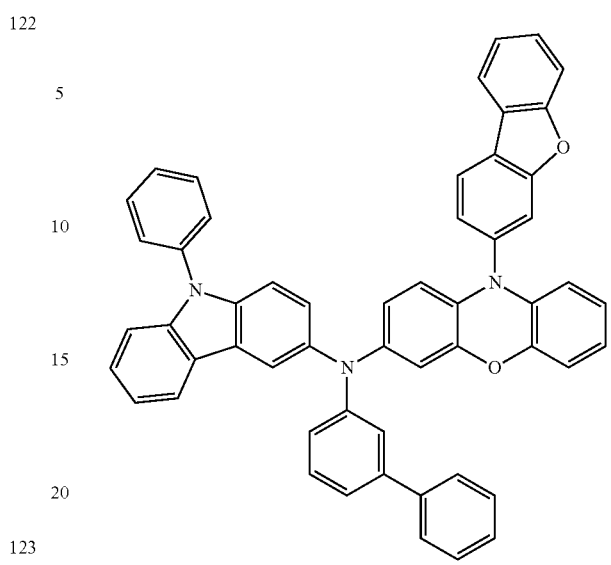
125
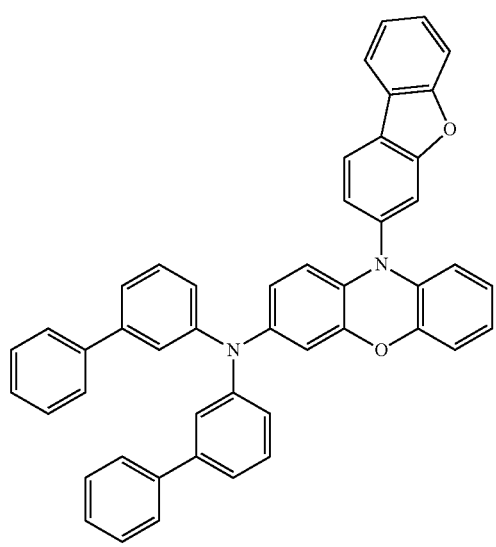 [SMILES: c1ccc(-c2cccc(N(c3cccc(-c4ccccc4)c3)c3ccc4c(c3)Oc3ccccc3N4c3ccc4c(c3)sc3ccccc34)c2)cc1]
123
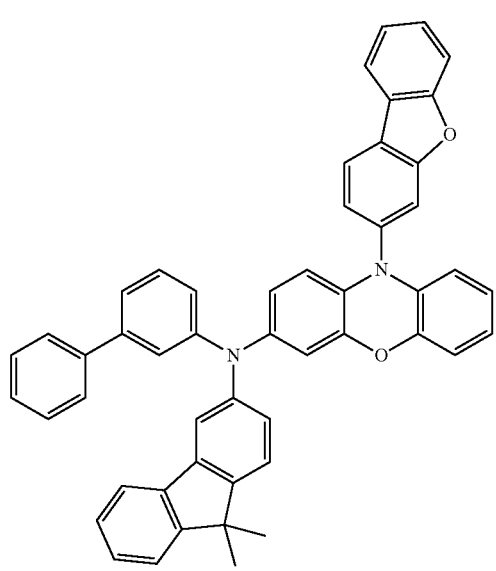
124
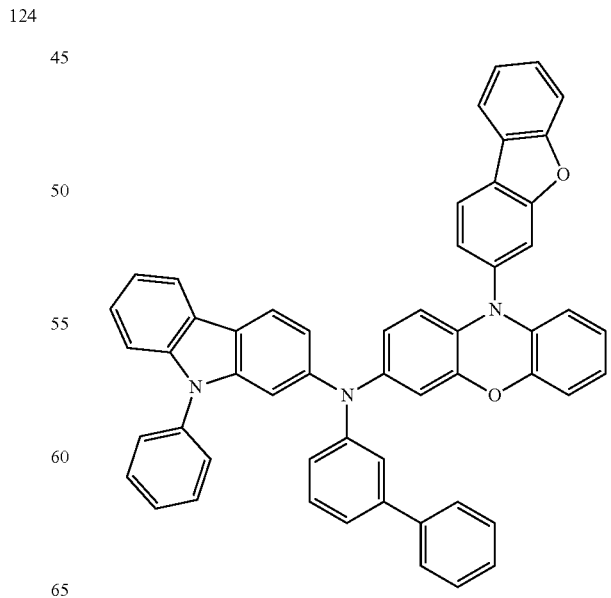
126

127
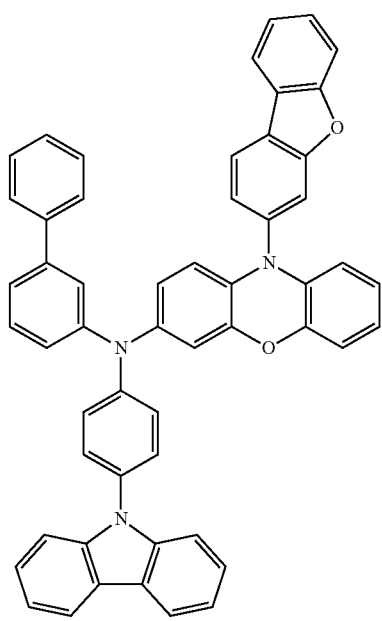
128
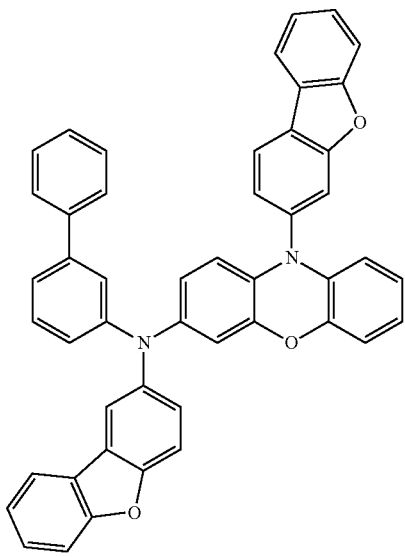
129
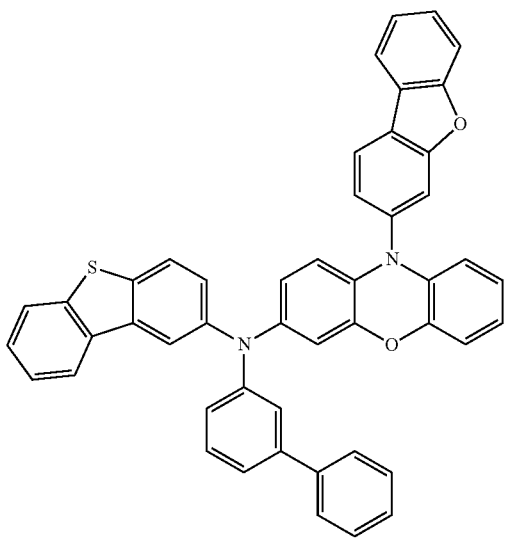
130
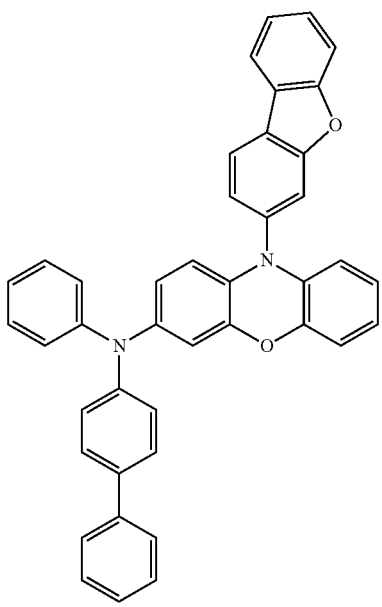

131 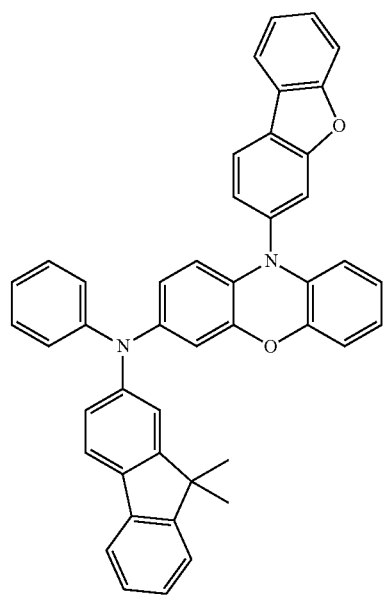
132 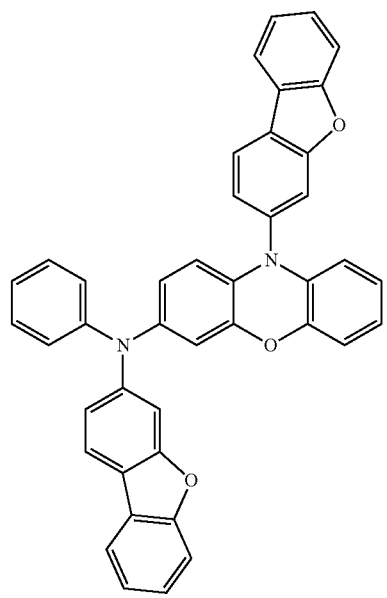
133 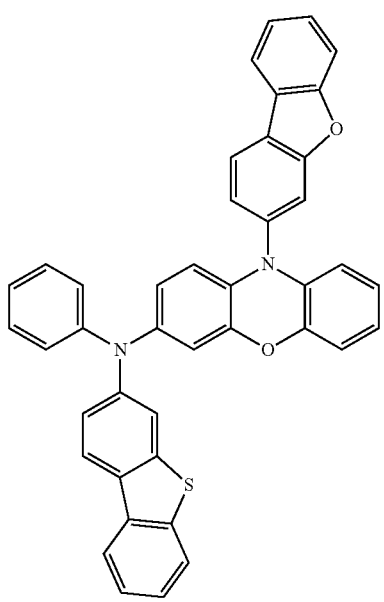
134 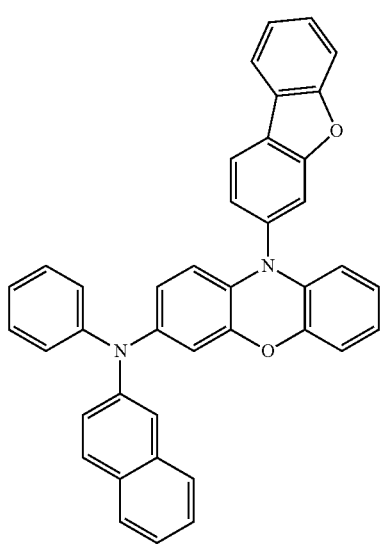
135 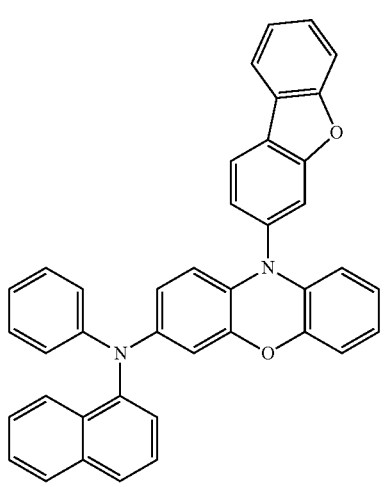

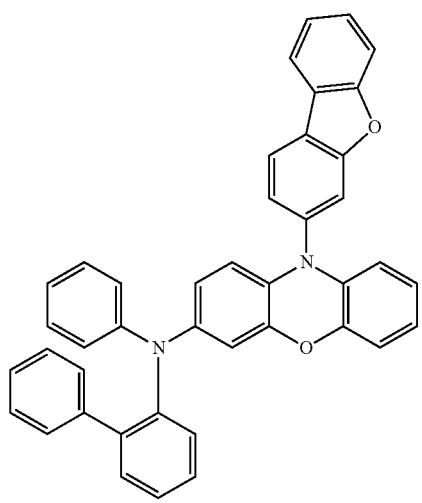
136
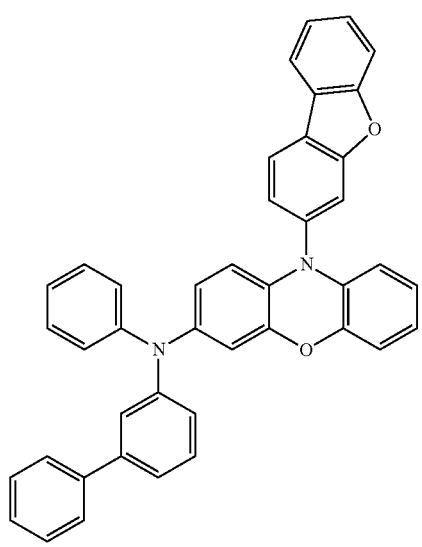 [SMILES: c1ccc(-c2cccc(N(c3ccccc3)c3ccc4c(c3)Sc3ccccc3N4c3ccc4c(c3)sc3ccccc34)c2)cc1]
137
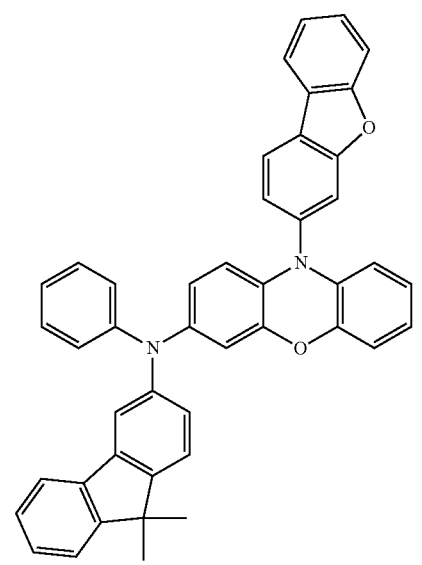
138
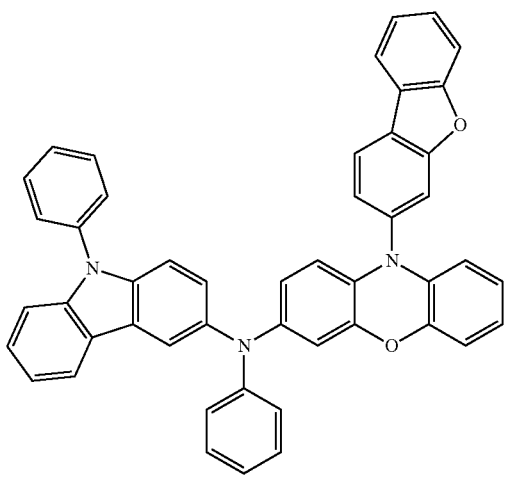
139
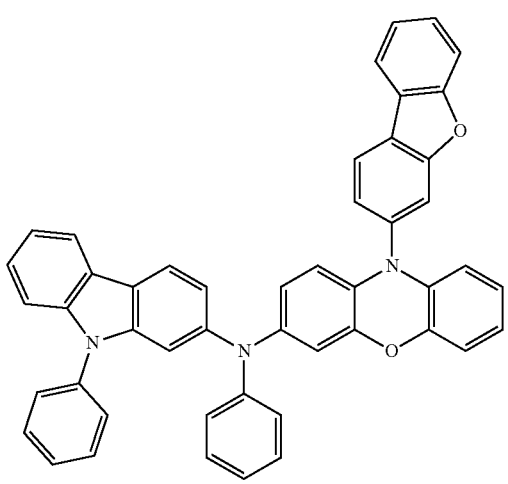
140
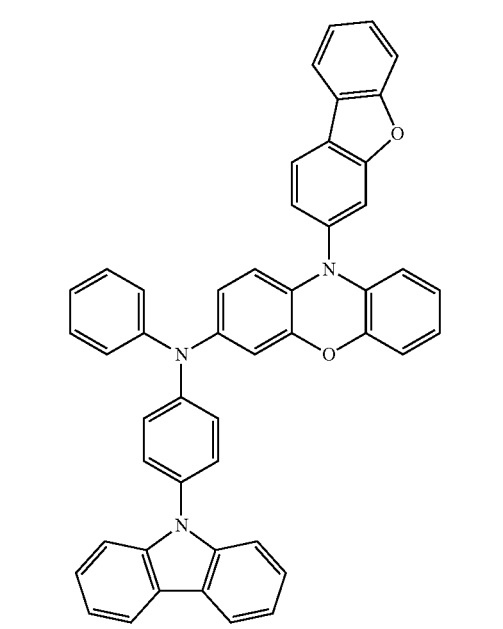
141

142
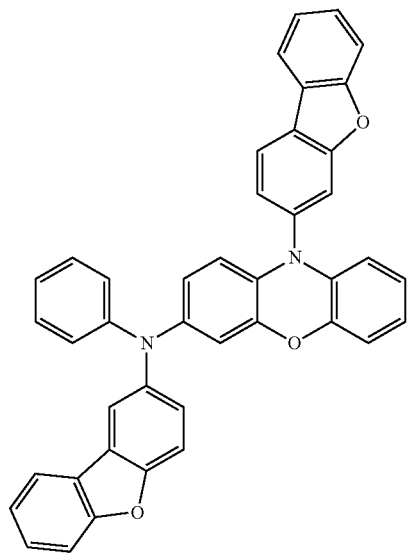
143
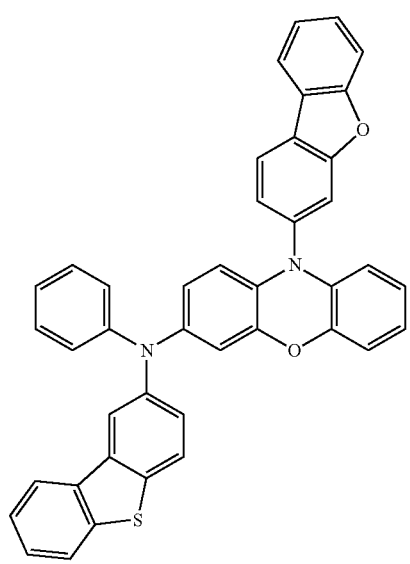
144
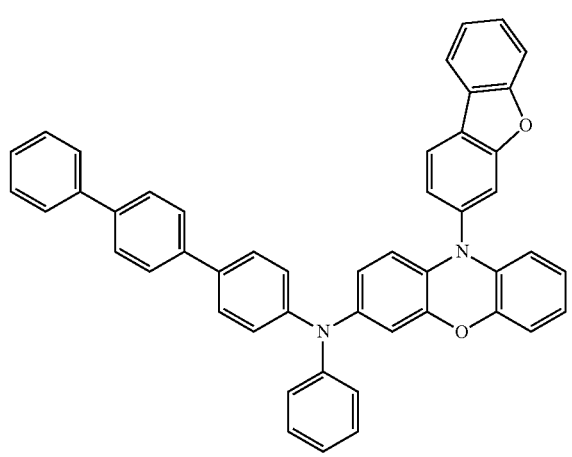
145
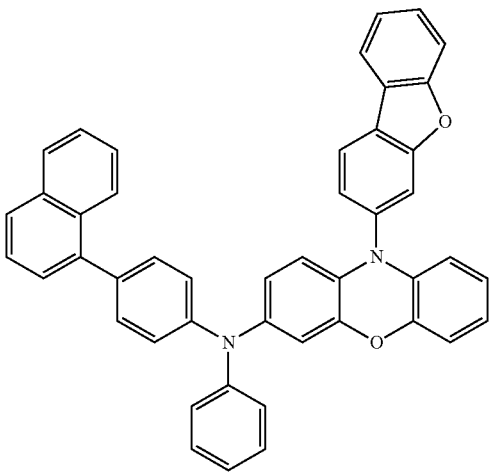
146
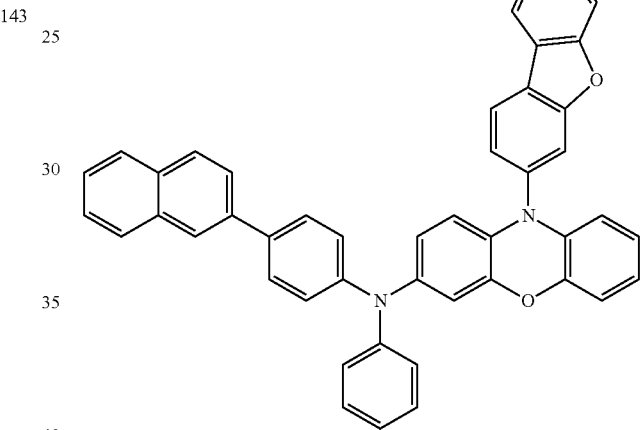
147
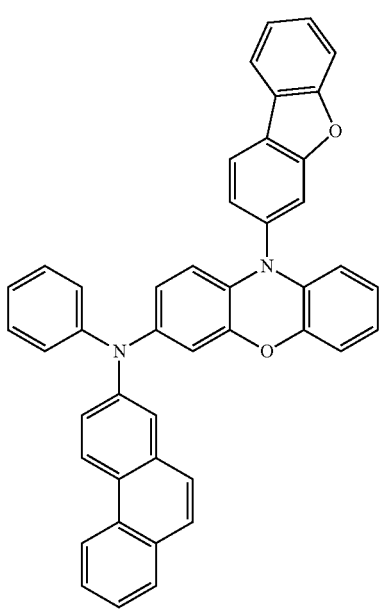

148
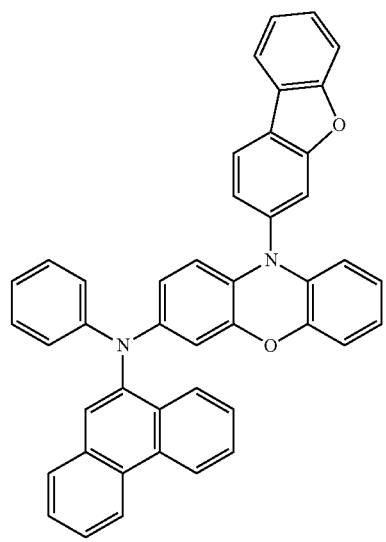
149
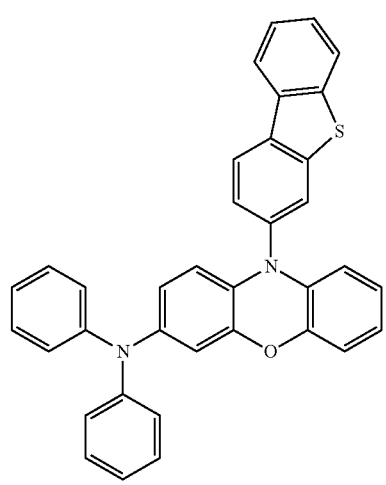
150
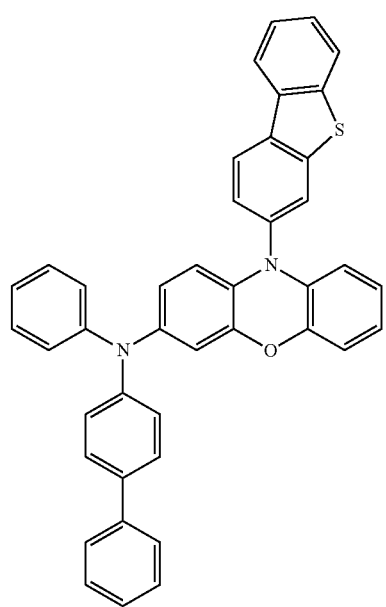
151
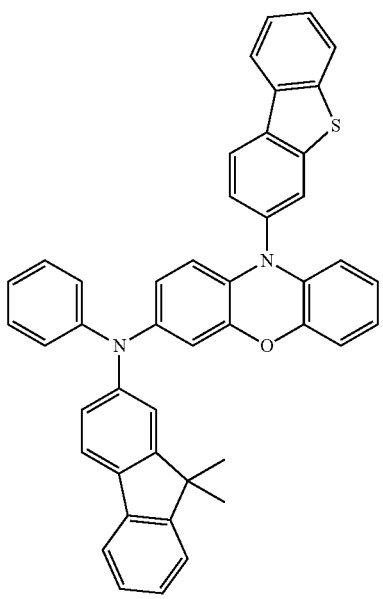
152
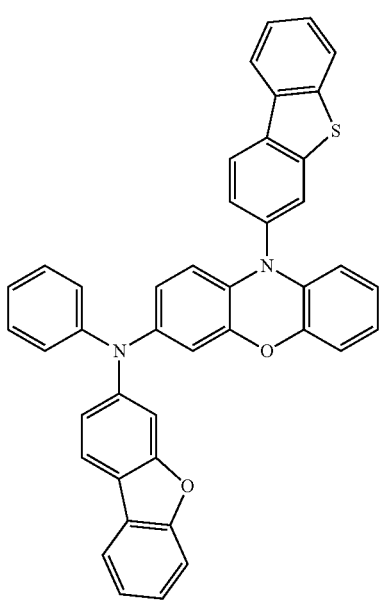

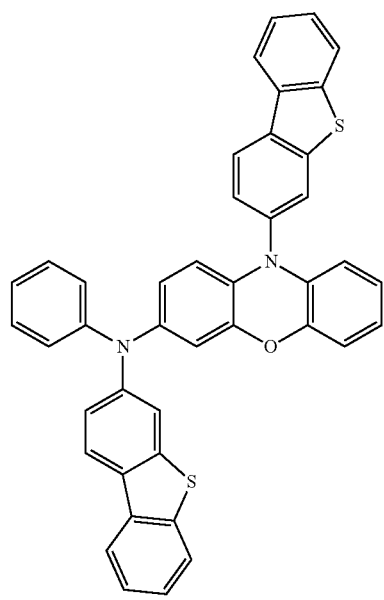
153
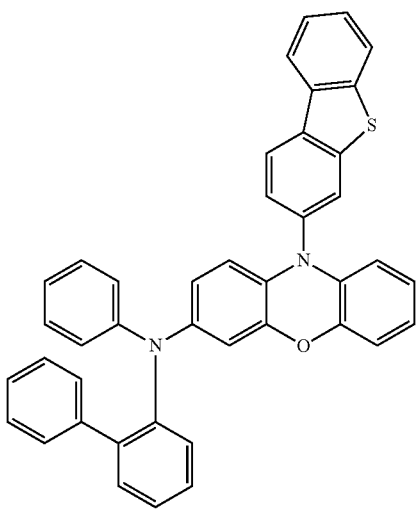
156
154
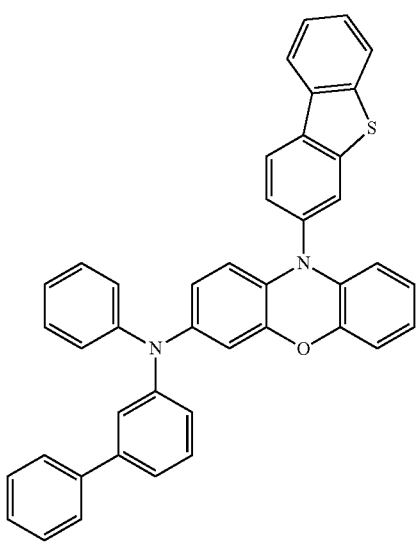
157
155
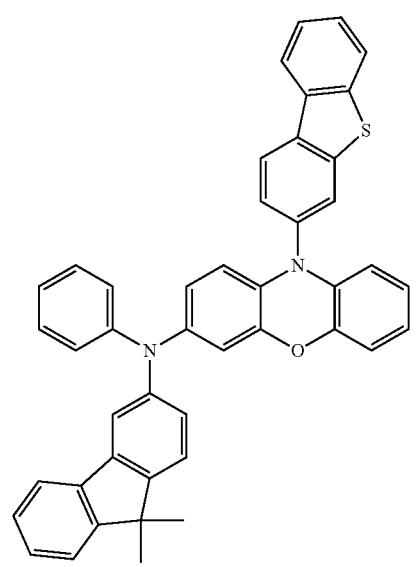
158

159
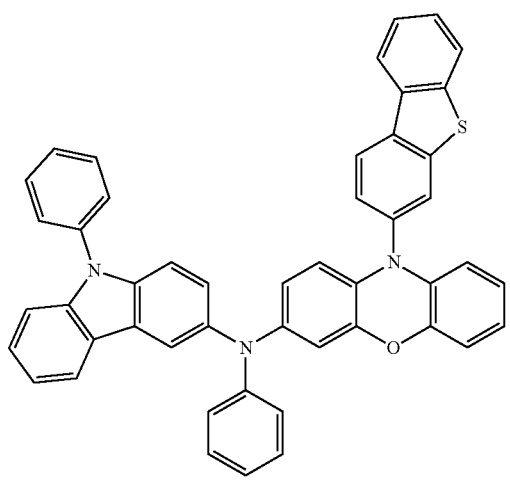
160
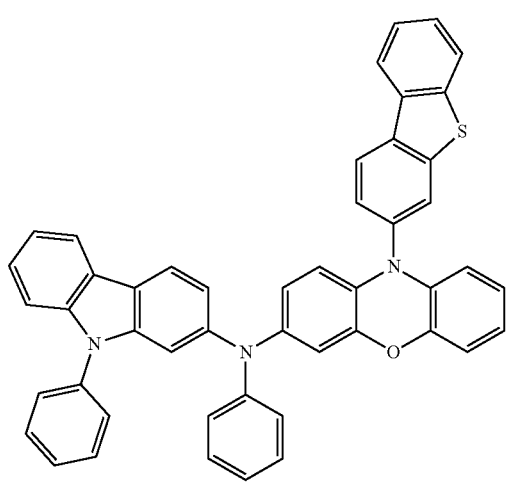
161
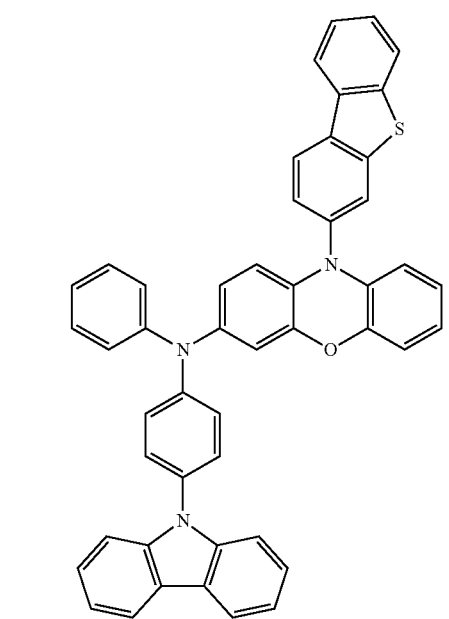
162
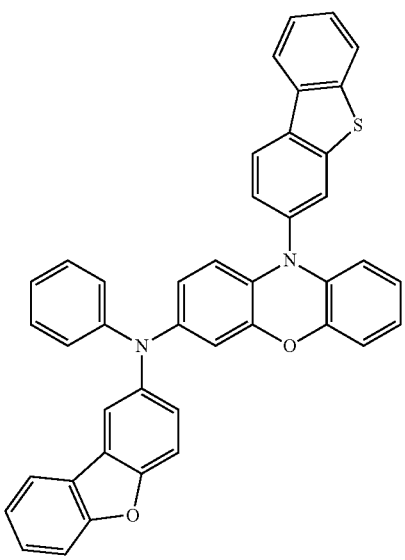
163
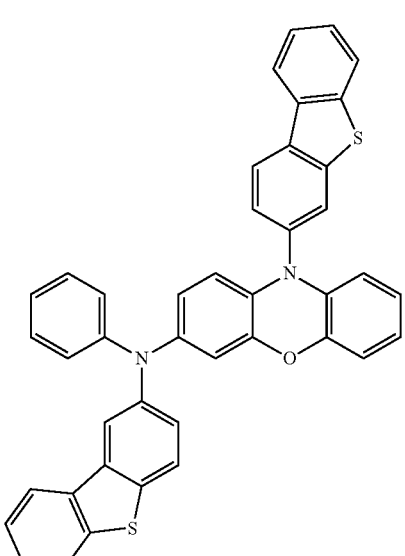
164
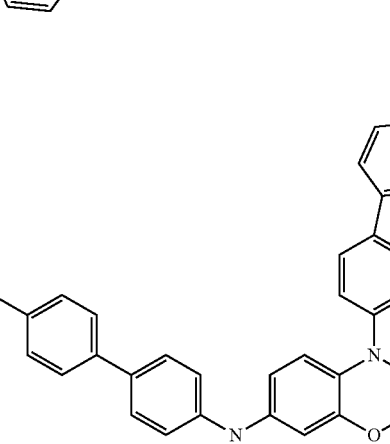

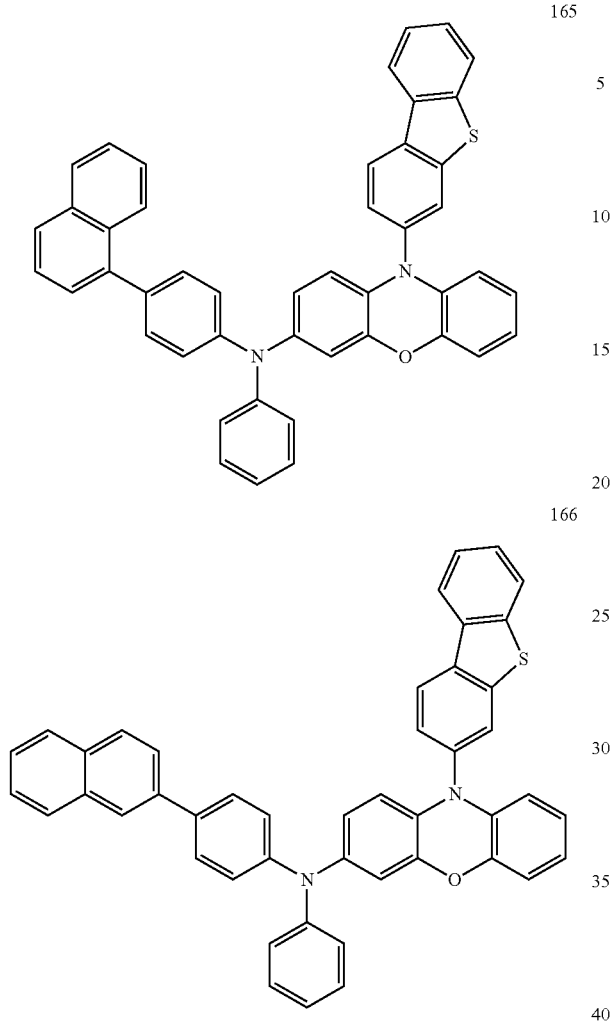
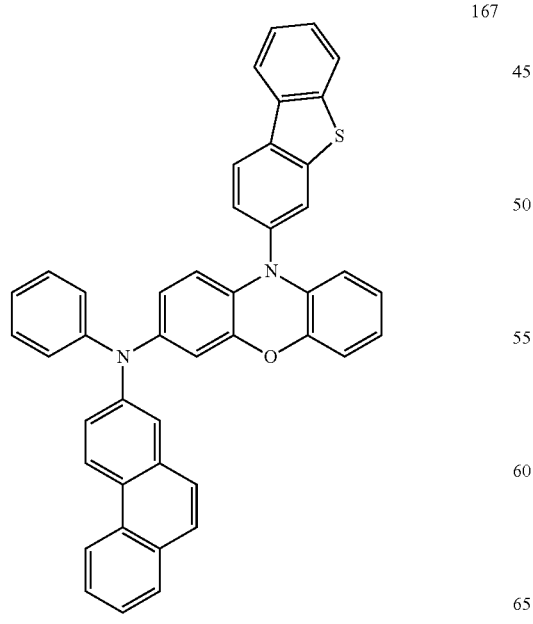
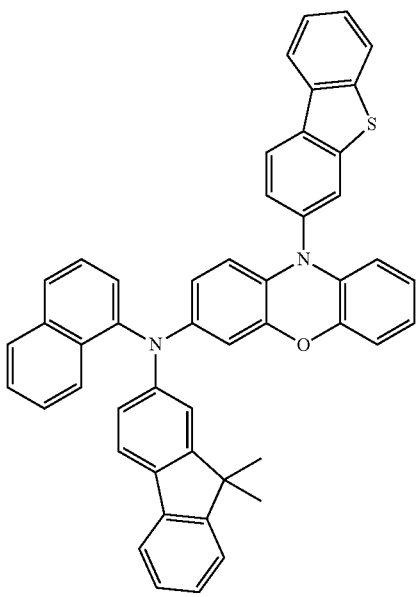
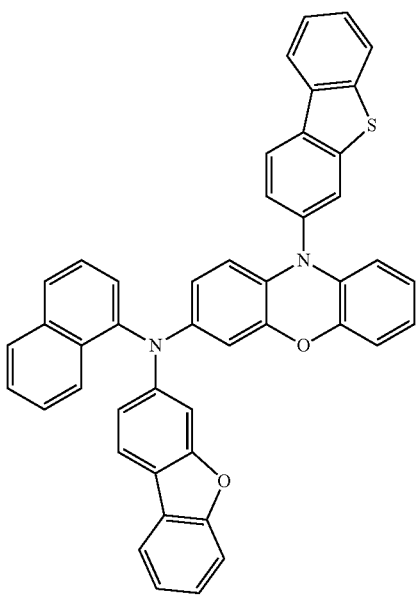

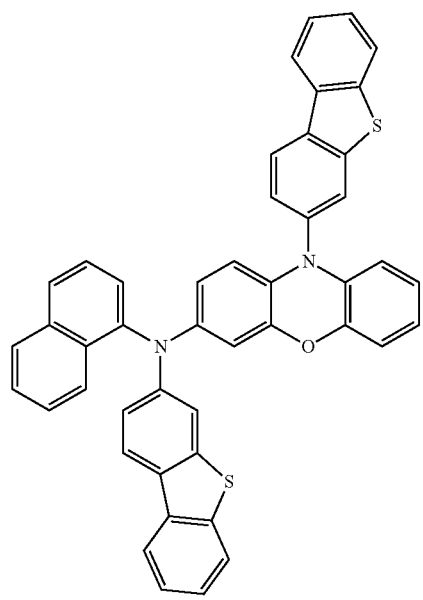
175
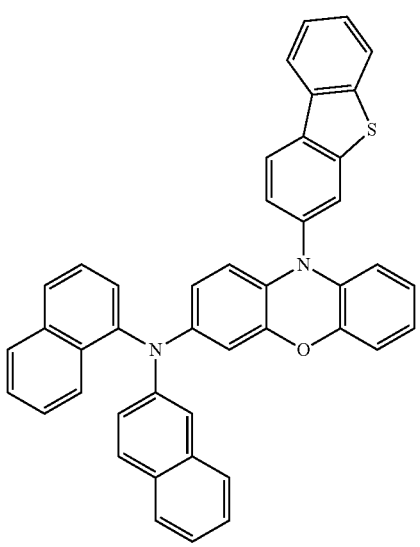
177
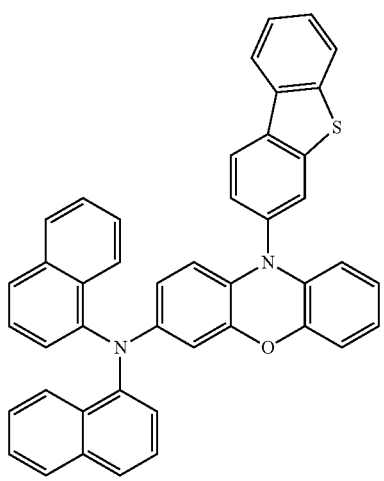
178
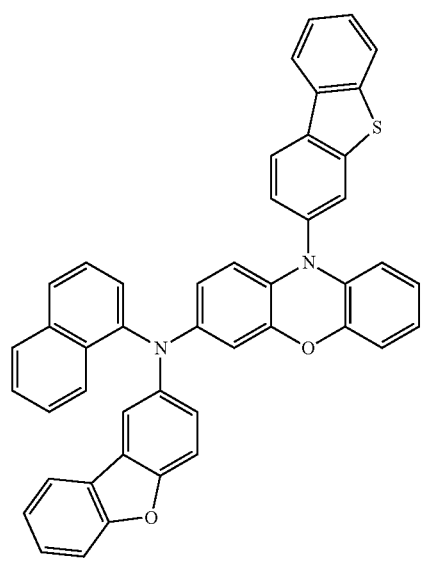
176
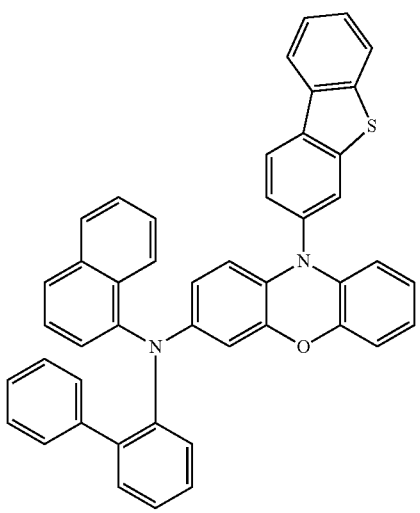
179

-continued
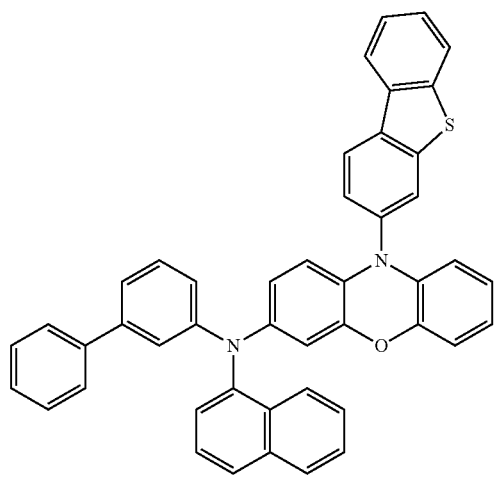
180
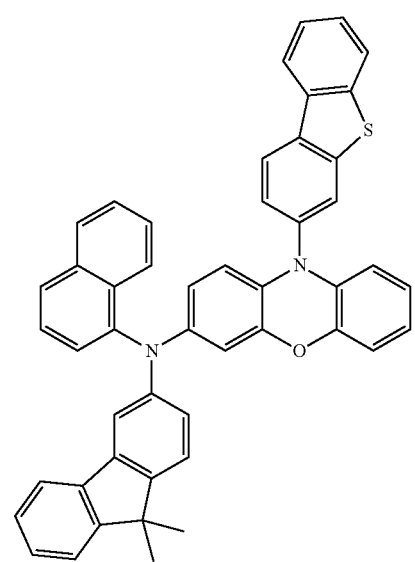
181
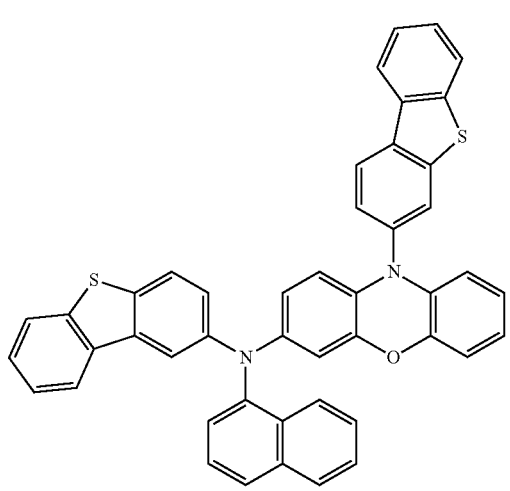
182
-continued
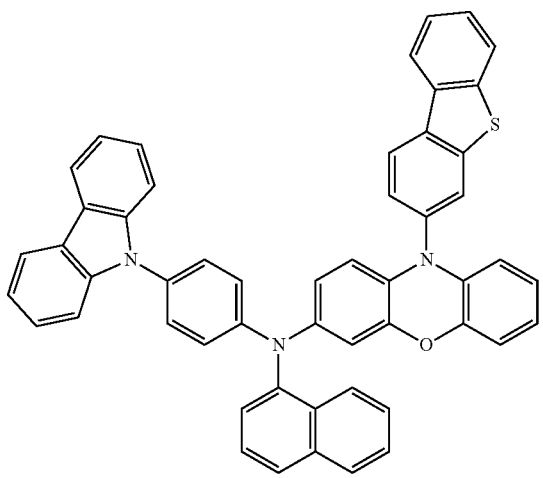
183
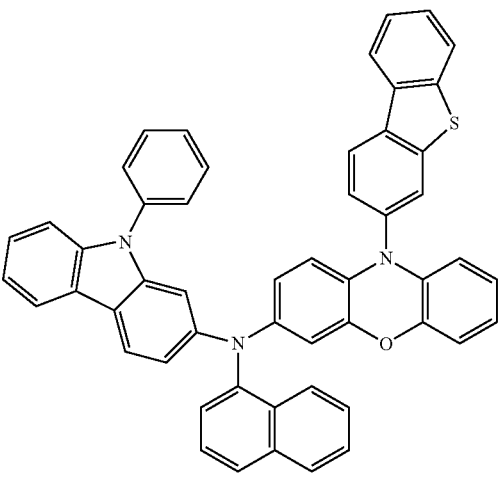
184
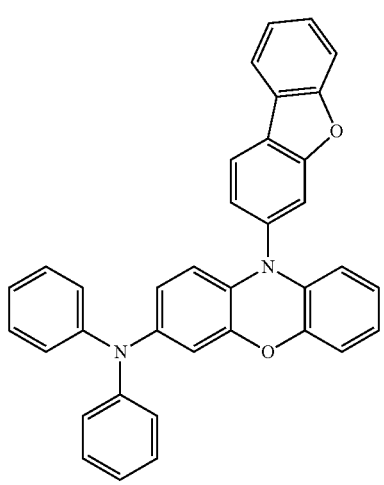
199

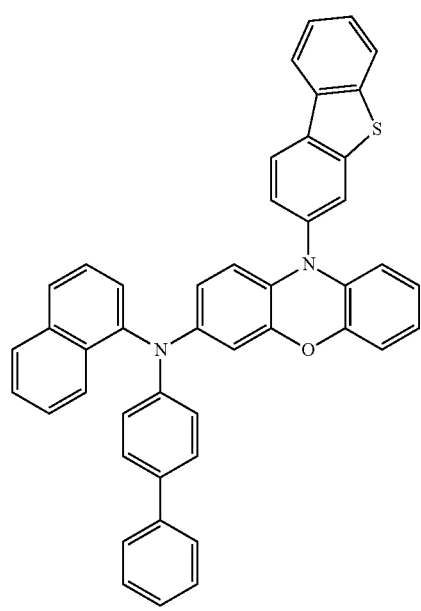
200
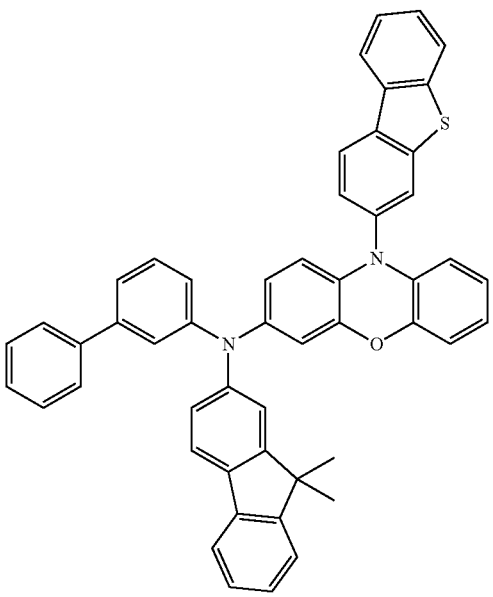
249
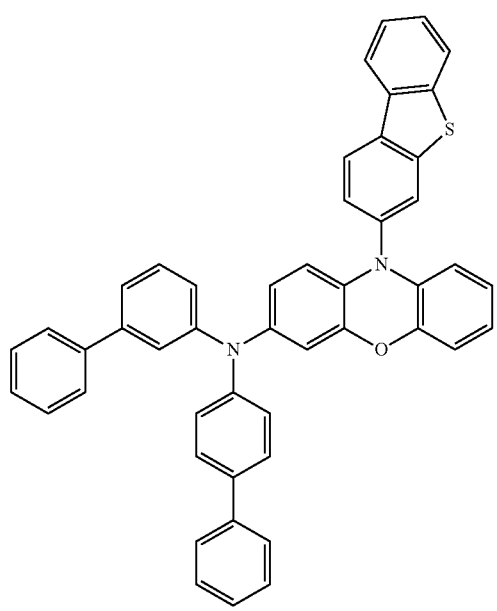
248
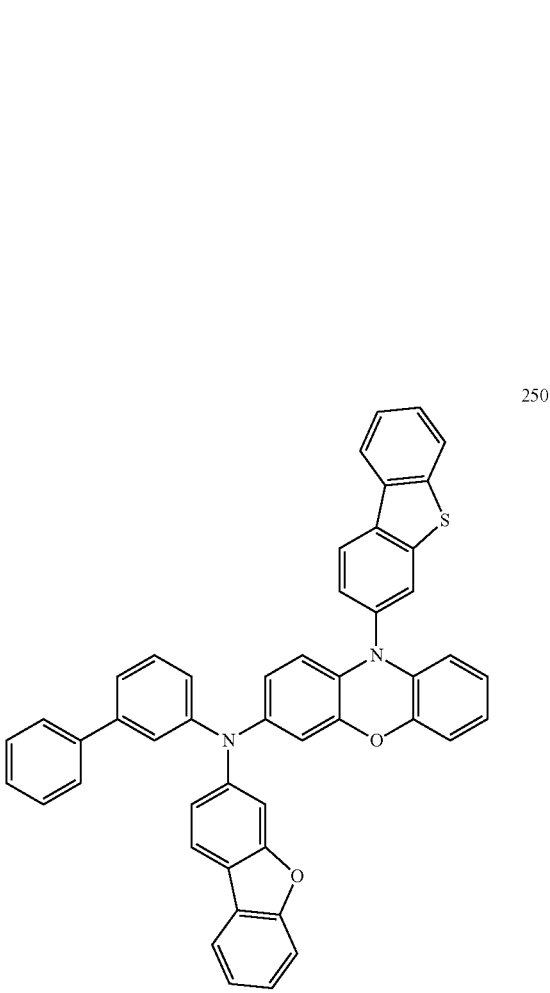
250

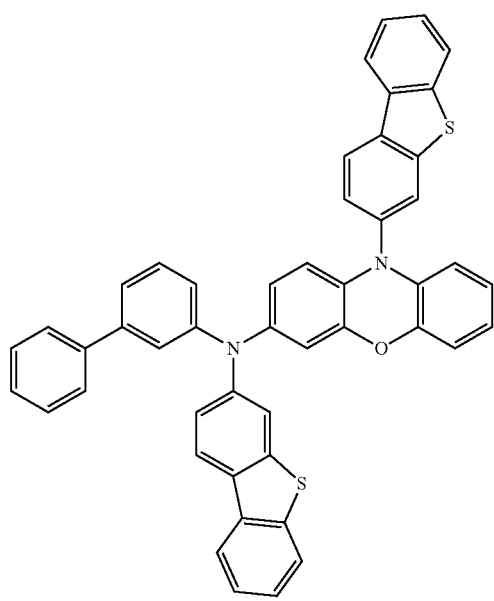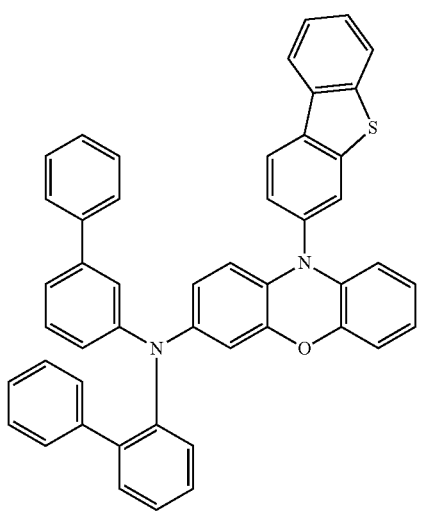

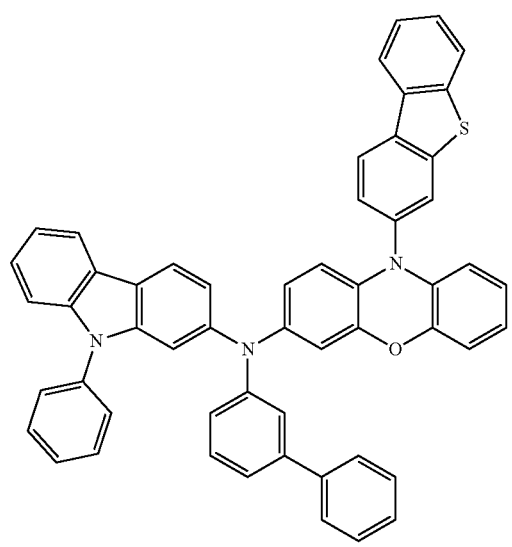 257
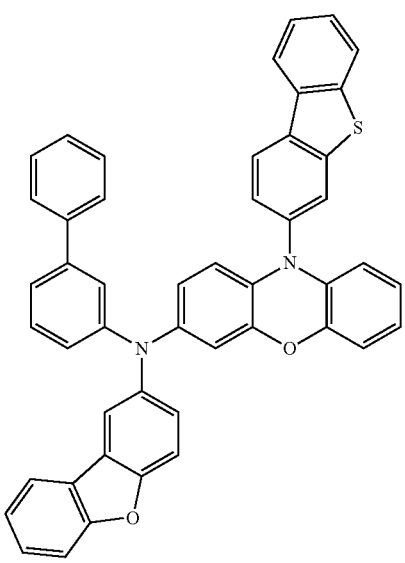 259
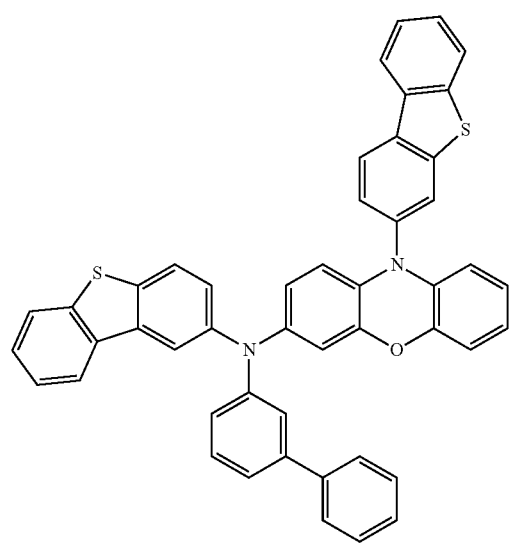 260
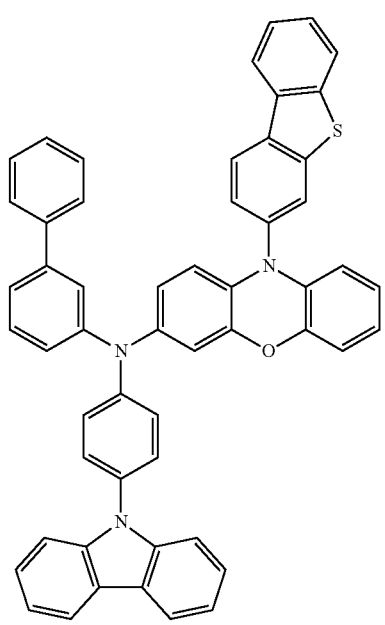 258
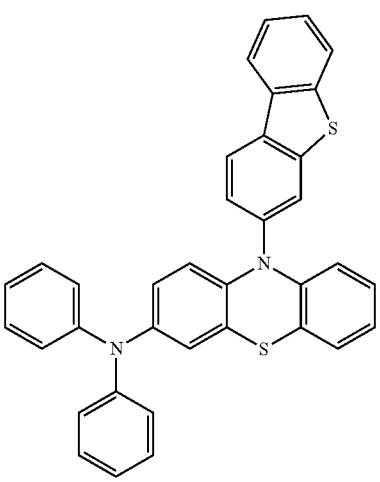 325

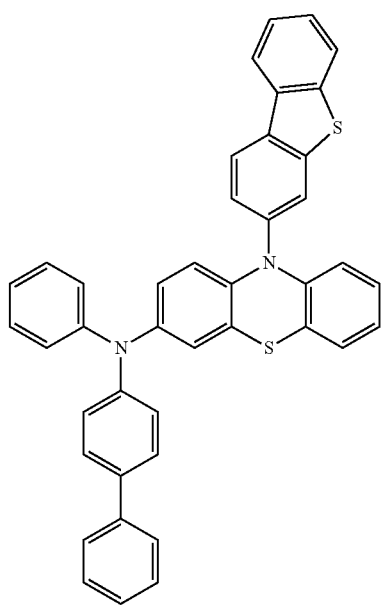
326
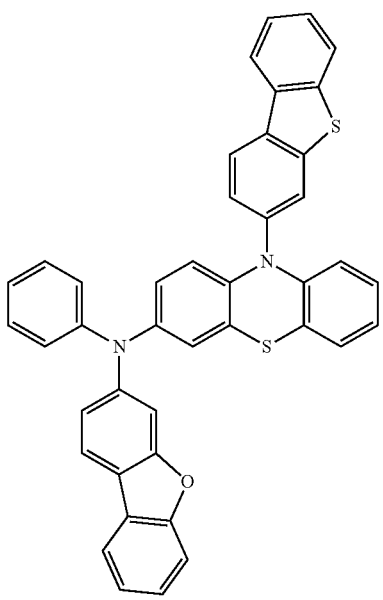
328
327
329

55
-continued
330
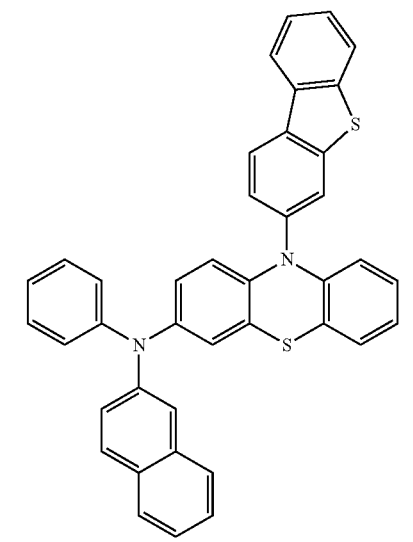
331
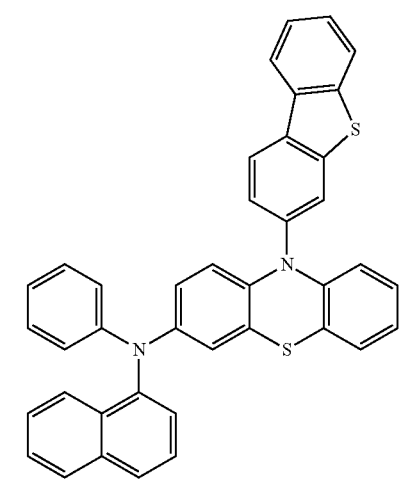
332
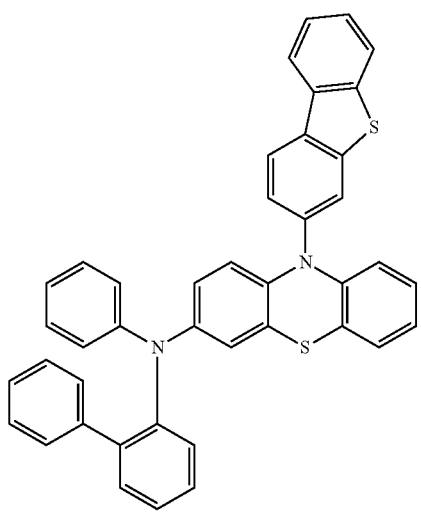
56
-continued
333
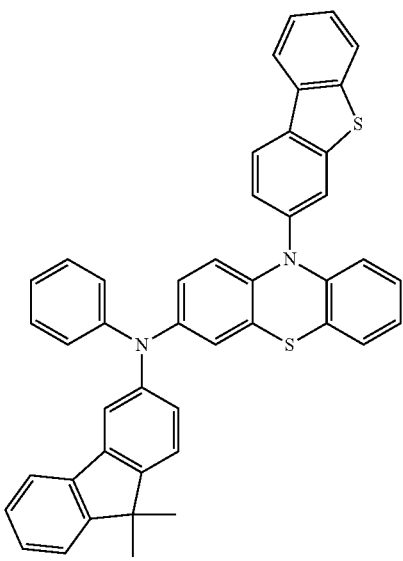
334
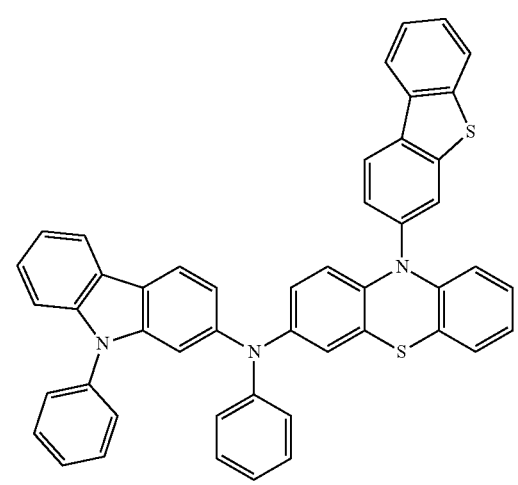
335
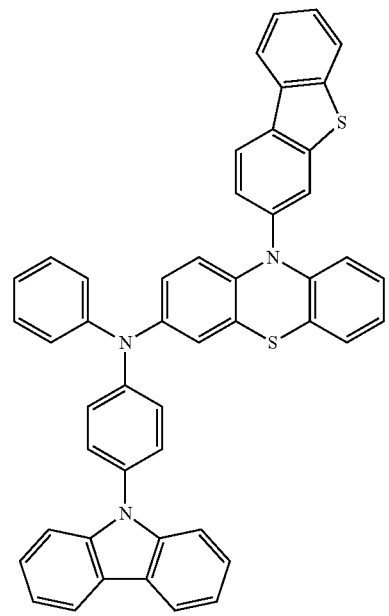

336
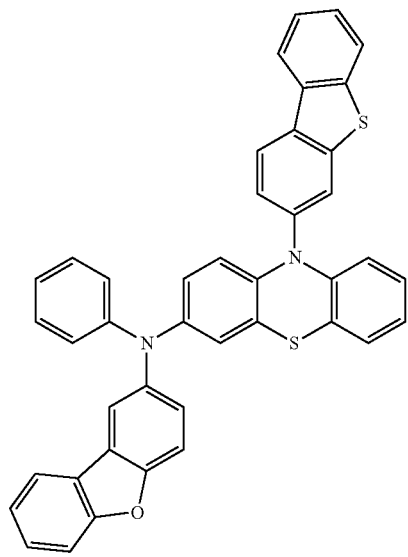
337
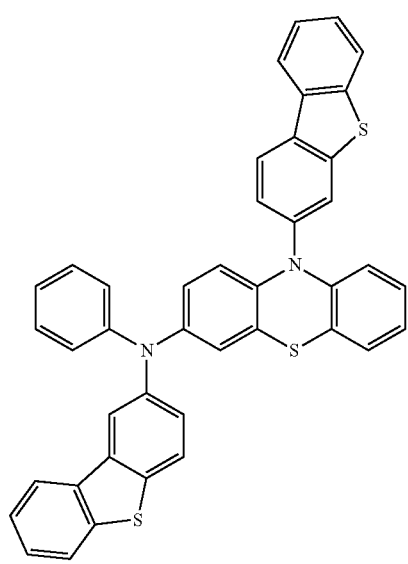
338
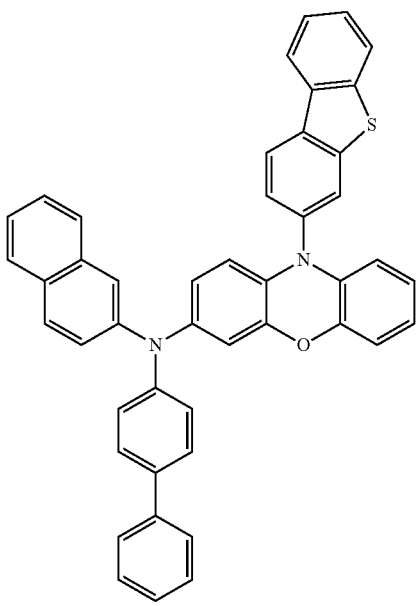
339
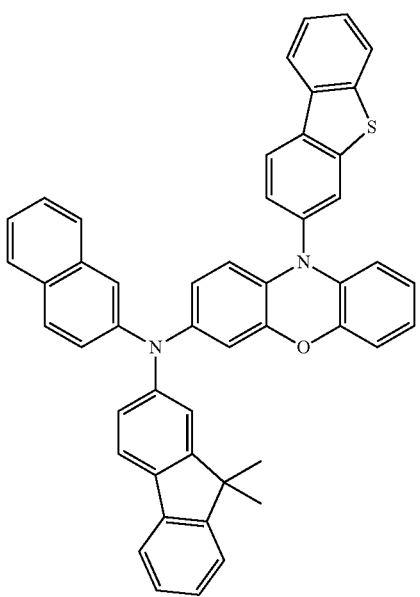

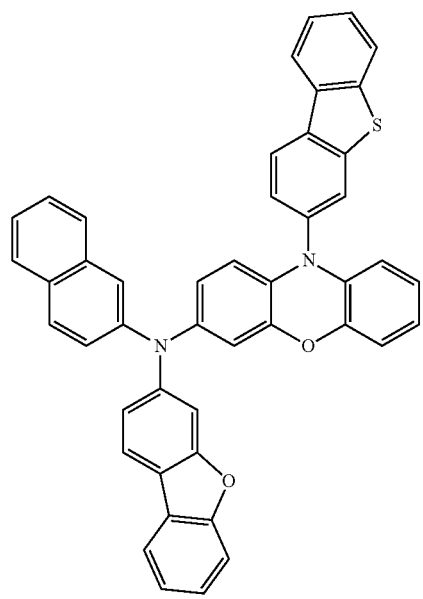
340
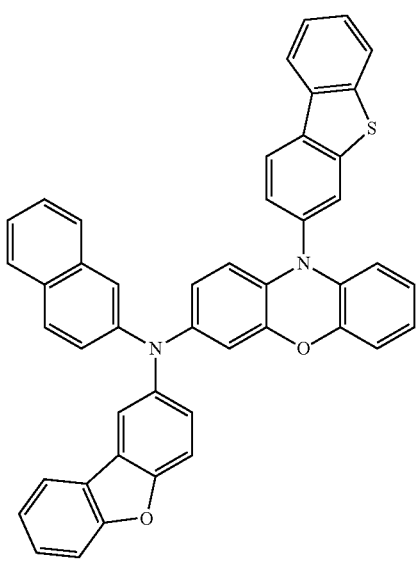
342
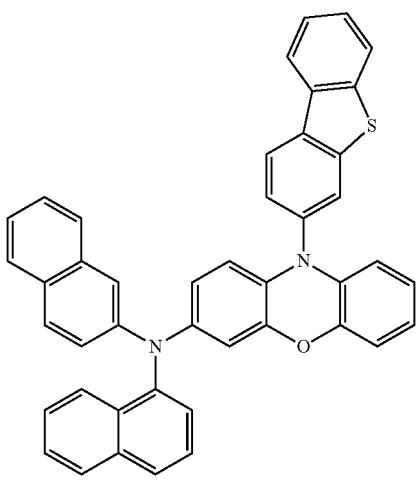
343
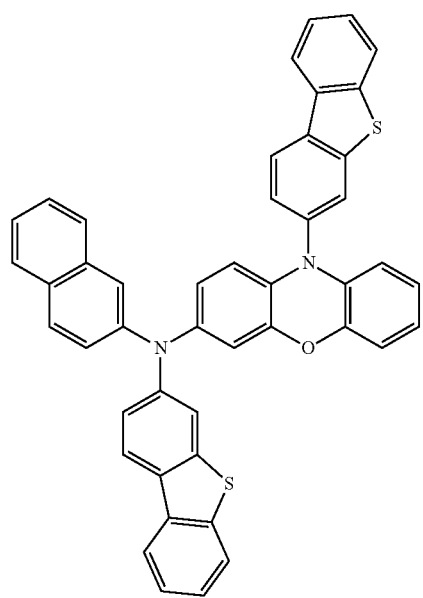
341
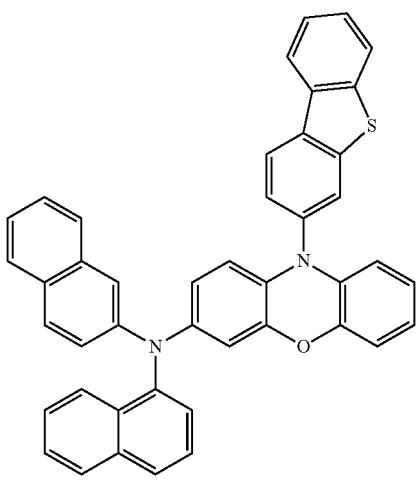
344

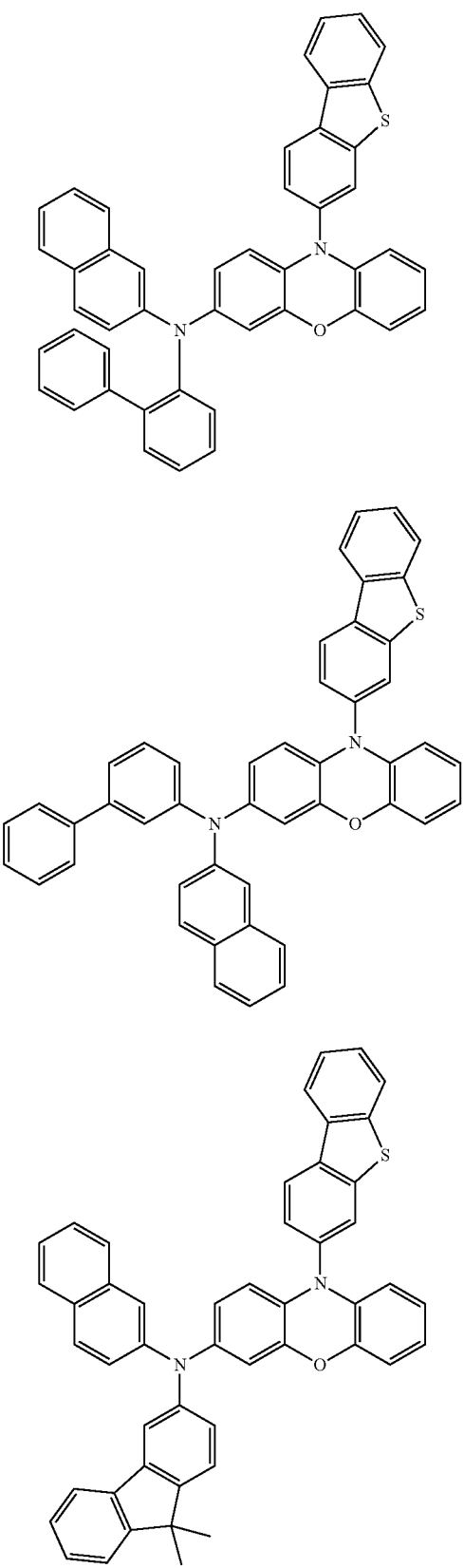
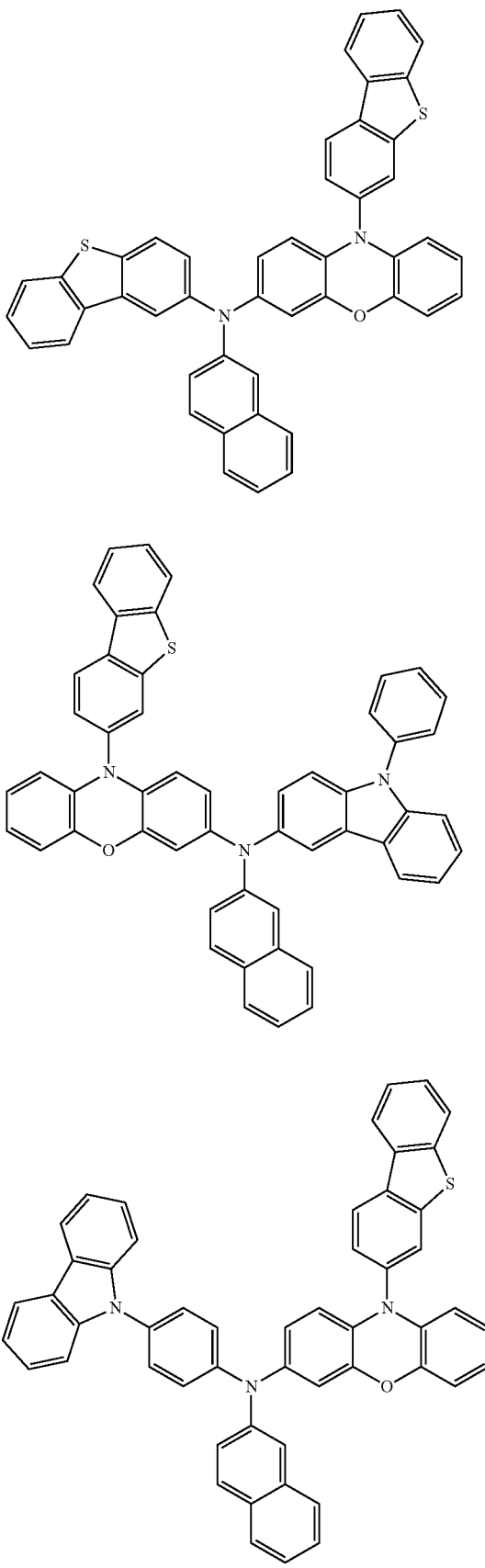

-continued
351
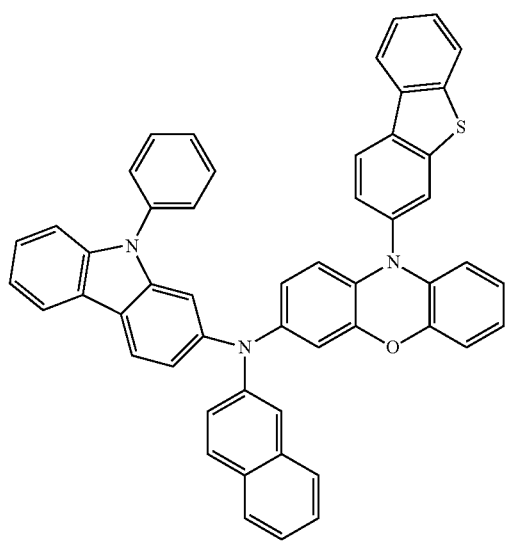
352
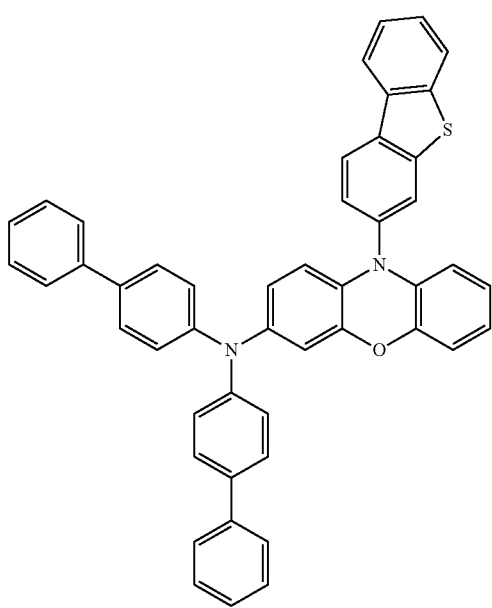
353
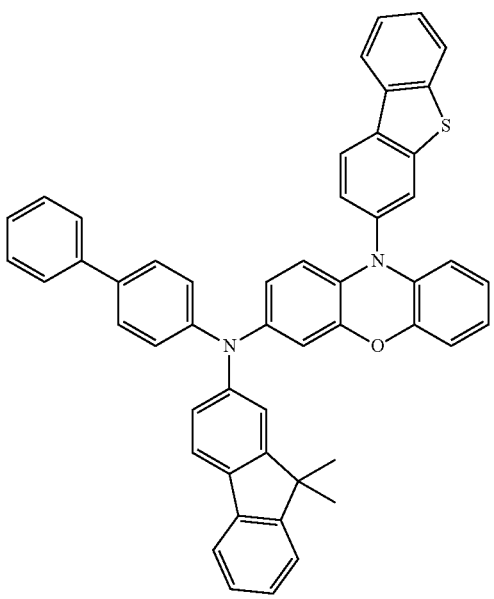
354
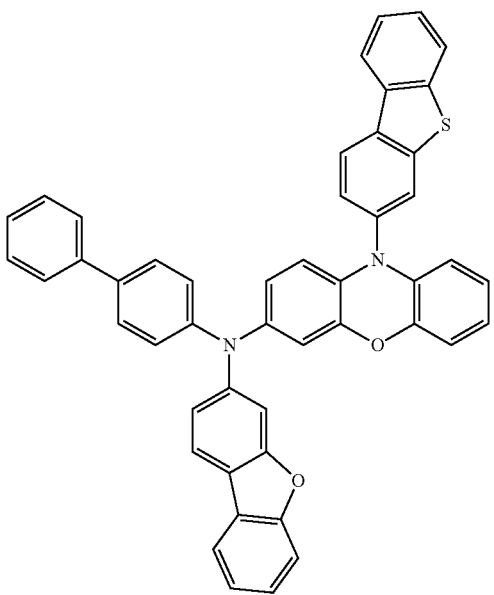

355
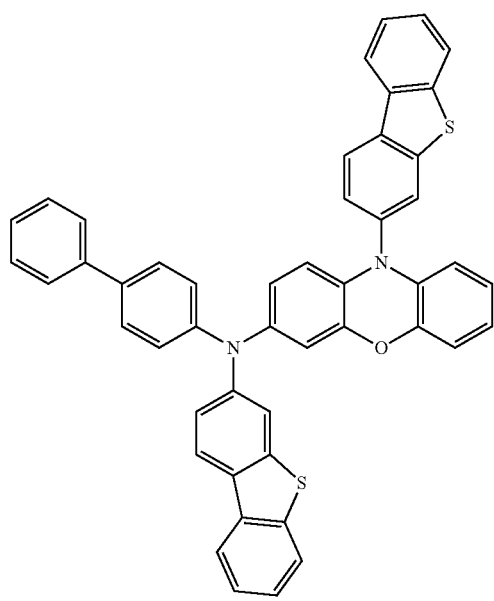
356
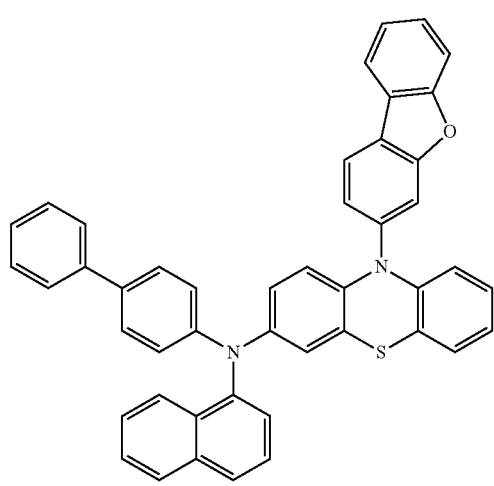
357
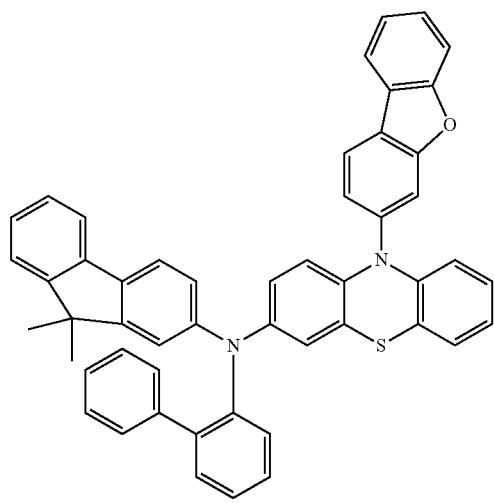
358
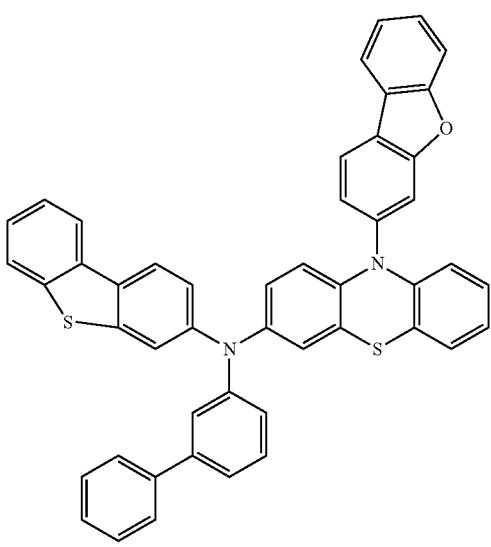
359
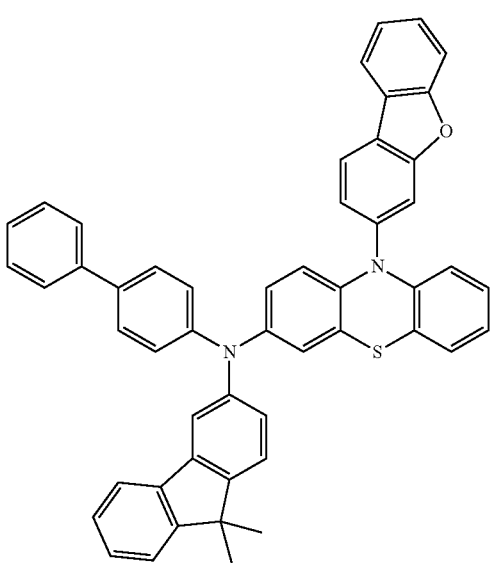

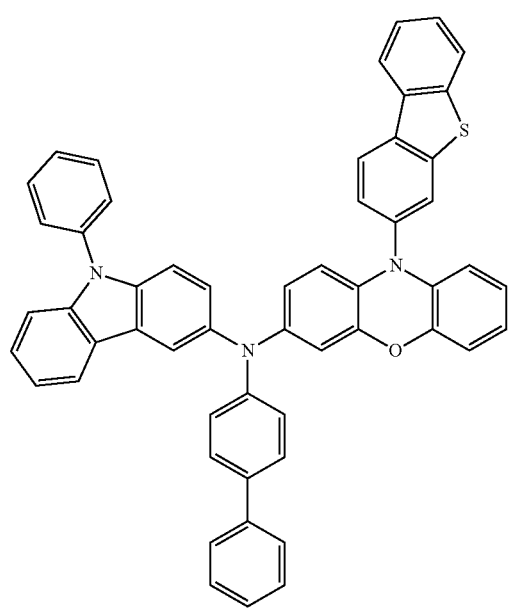
360
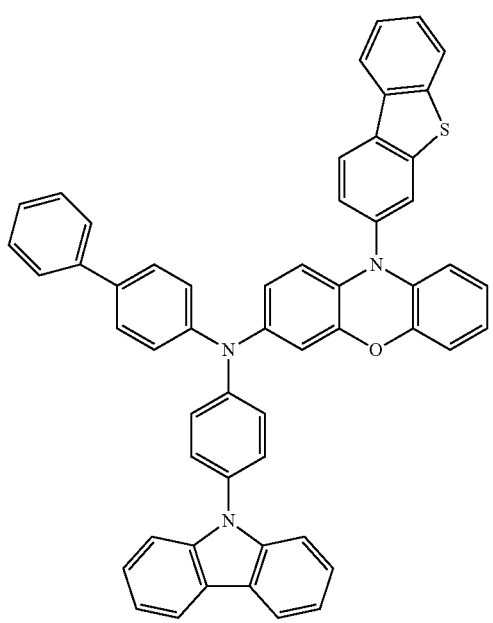
362
361
363

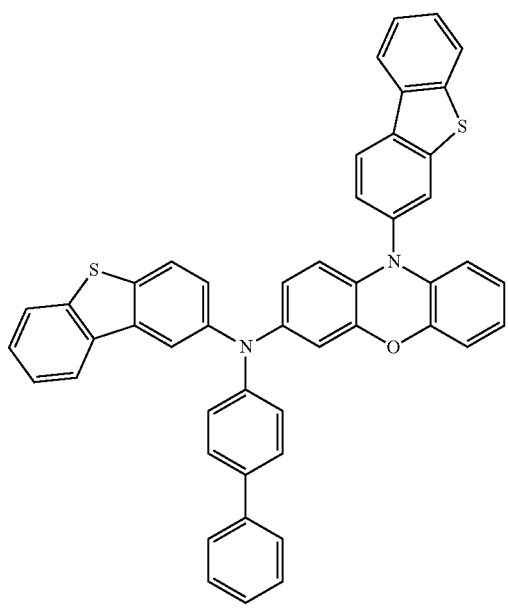
364
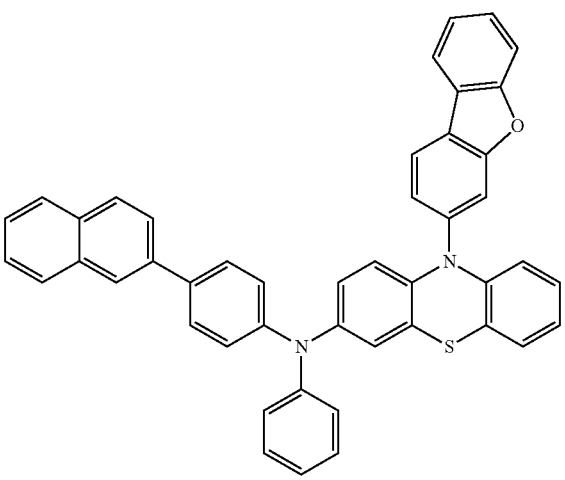
367
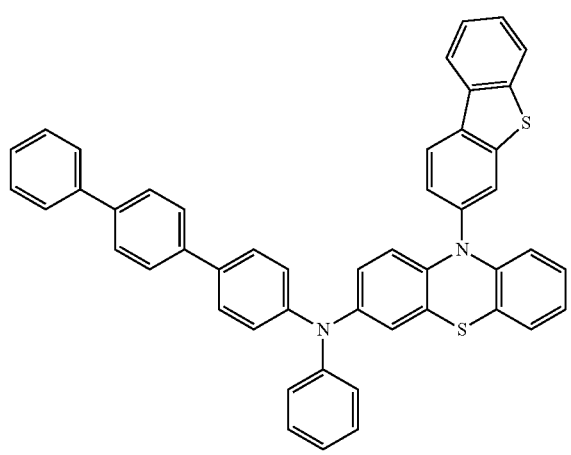
365
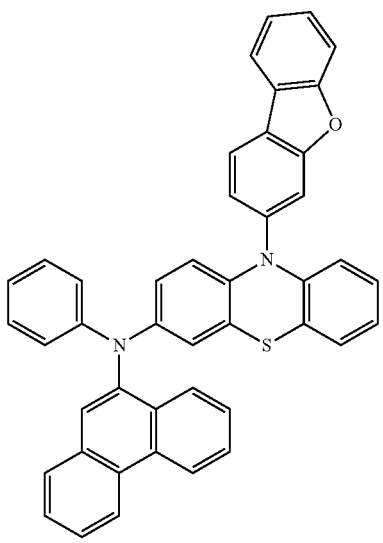
368
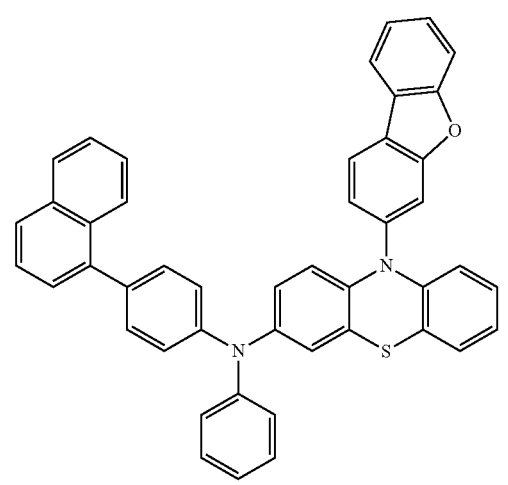
366
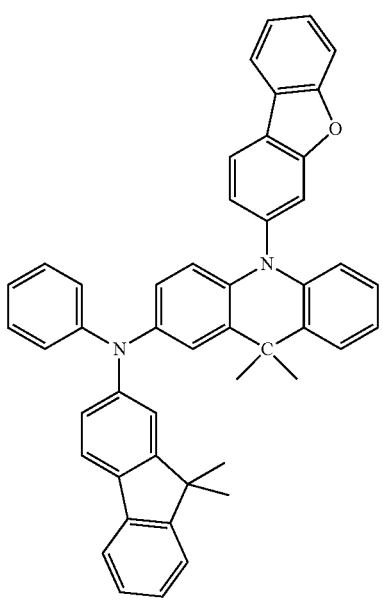
384

71
-continued
386
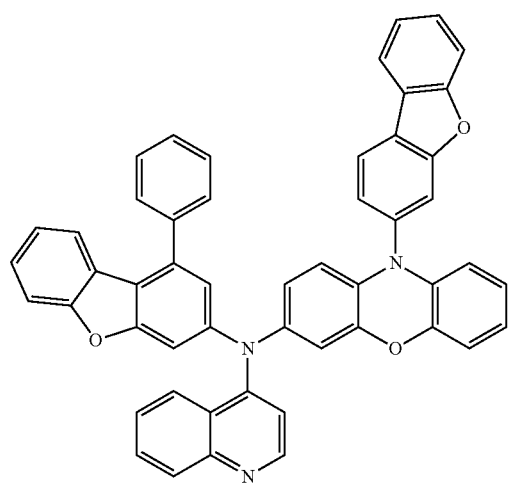
387
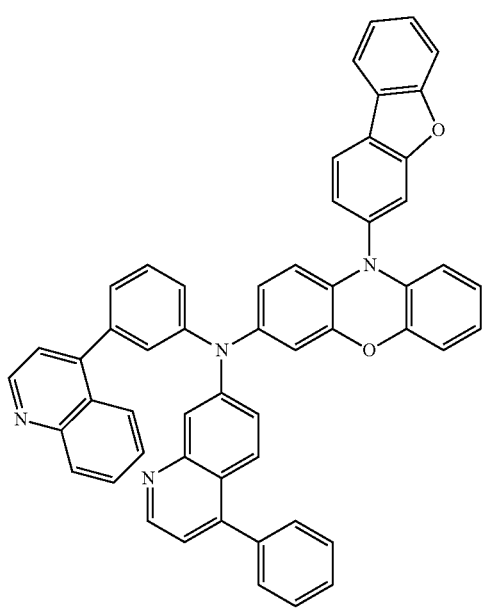
72
-continued
388
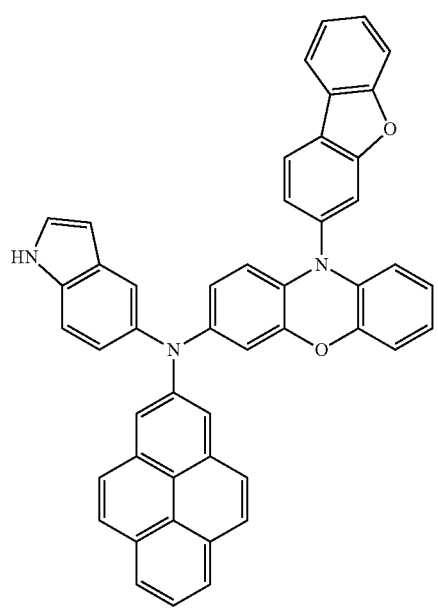
389
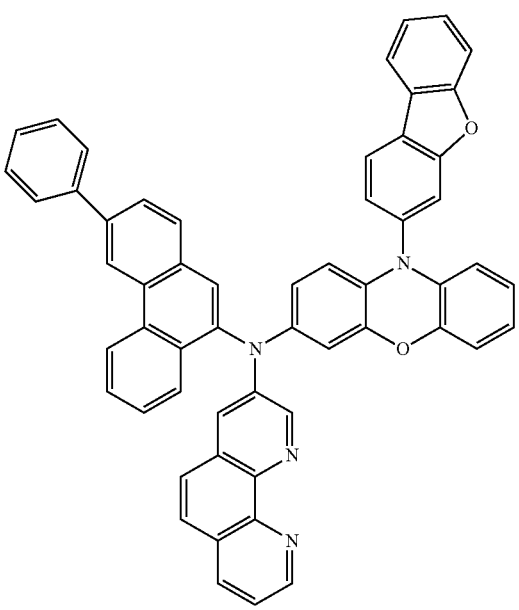

-continued

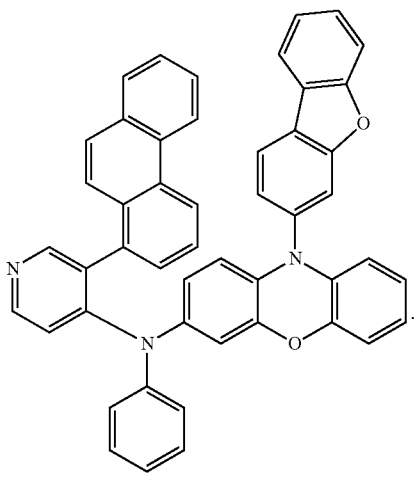

390

It should be noted that the above nitrogen-containing compounds are only exemplary nitrogen-containing compounds, and there may also be other nitrogen-containing compounds, which will not be listed here.

A synthesis process of the nitrogen-containing compound of the disclosure will be described in detail below through examples. However, the following examples are only illustrations of the disclosure, and do not limit the disclosure.

In the synthesis examples described below, unless otherwise stated, all temperatures are expressed in a unit of ° C. Some reagents are purchased from commodity suppliers such as Aldrich Chemical Company, Arco Chemical Company, and Alfa Chemical Company, which are used without further purification unless otherwise stated. Compounds of the synthesis method not mentioned in the disclosure are all raw material products obtained through commercial channels.

During purification, a chromatographic column is a silica gel column, and silica gel (100 to 200 mesh) is purchased from Qingdao Haiyang Chemical Co., Ltd.

In each synthesis example, low-resolution mass spectrometry (MS) data are obtained under the following conditions: Agilent 6120 quadrupole HPLC-M (column model: Zorbax SB-C18, 2.1×30 mm, 3.5 µm, 6 min, flow rate: 0.6 mL/min; and mobile phase: a proportion of (acetonitrile with 0.1% methanoic acid) in (water with 0.1% methanoic acid) is 5% to 95%), electrospray ionization (ESI), and ultraviolet (UV) detection at 210 nm/254 nm.

$^1$H nuclear magnetic resonance spectroscopy (HNMR): Through a Bruker 400 MHz NMR spectrometer, the HNMR is conducted at room temperature with CDCl$_3$ (in ppm) as a solvent and tetramethylsilane (TMS) (0 ppm) as a reference standard. When multiplets appear, the following abbreviations will be adopted: s: singlet, d: doublet, t: triplet, and m: multiplet.

A target compound is tested using Agilent 1260 pre-HPLC or Calesep pump 250 pre-HPLC (column model: NOVASEP 50/80 mm DAC): UV detection at 210 nm/254 nm.

The analysis and detection of intermediates and compounds in the disclosure is conducted using an ICP-7700 mass spectrometer and an M5000 elemental analyzer.

(1) COMPOUND SYNTHESIS EXAMPLES

In an embodiment, the compound of the disclosure can be prepared through the following synthesis scheme, wherein $X_1$ and $X_2$ can have the definitions described in the specification of the disclosure, and $R^1$ and $R^2$ are each independently selected from substituted or unsubstituted aryl with 6 to 30 carbon atoms and heteroaryl with 6 to 30 carbon atoms.

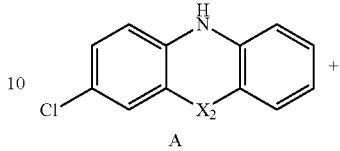

A

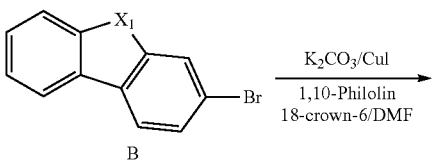

B

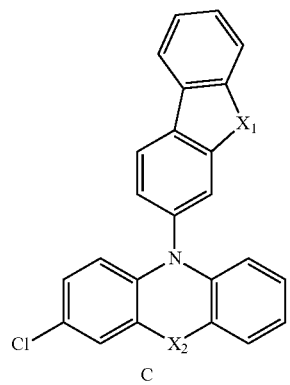

C

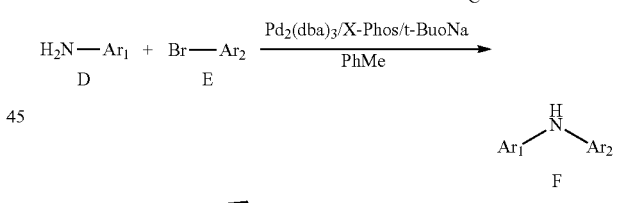

F

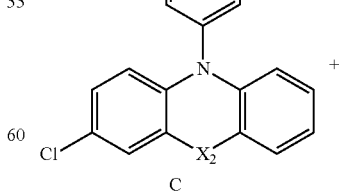

C

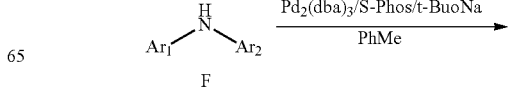

F

-continued

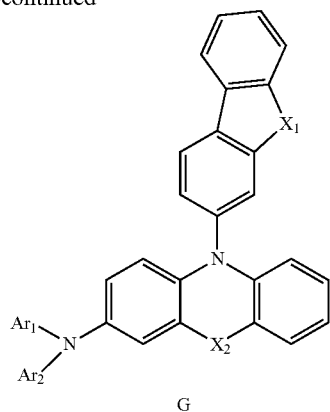

G

In the above synthesis scheme, the raw materials aryl halide A and the raw materials aryl halide B undergo a Ullmann coupling reaction to obtain a solid intermediate compound C, the raw material arylamine D and the raw material aryl halide E undergo a Buchwald-Hartwig coupling reaction to obtain an intermediate compound F, and then the intermediate C and the intermediate F undergo a Buchwald-Hartwig coupling reaction to obtain a compound with a structure shown in formula G.

The compounds of the disclosure can all be prepared through the above general synthesis scheme. In order to be understood easily, with a preparation process of a specific compound as an example, synthesis processes of some compounds of the disclosure are exemplarily illustrated below.

Synthesis of Compound 2:

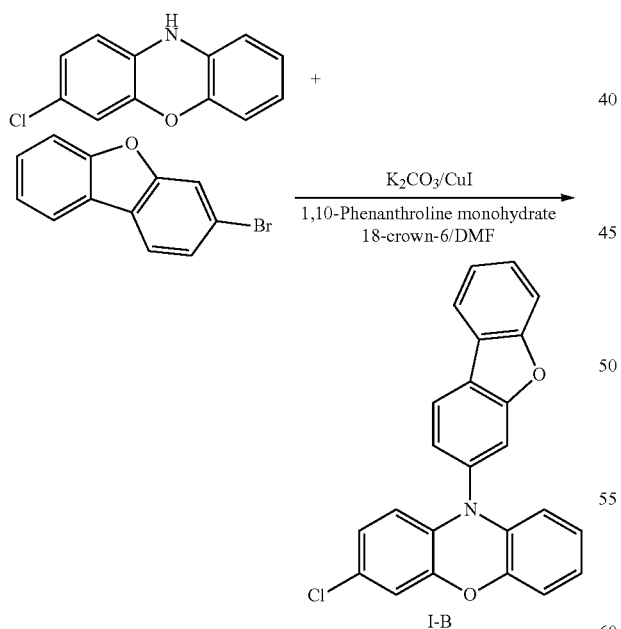

3-chloro-10H-phenoxazine (10 g, 45.95 mmol), 3-bromodibenzofuran (11.4 g, 46.5 mmol), potassium carbonate (15.87 g, 114.86 mmol), cuprous iodide (0.44 g, 2.30 mmol), o-phenanthroline (0.83 g, 4.60 mmol), and 18-crown ether-6 (0.61 g, 2.30 mmol) were added to N,N-dimethylformamide (DMF) (80 mL), and a resulting system was heated to 150° C. and stirred for 21 h under nitrogen atmosphere. A resulting reaction solution was cooled to room temperature, then extraction was conducted with ethyl acetate, and a separated organic phase was washed with water until neutral; magnesium sulfate was added to the organic phase for drying, a resulting mixture was filtered to obtain a filtrate, the filtrate was concentrated in a vacuuo to obtain a crude product. The obtained crude product was purified by recrystallization using a n-heptane to obtain a solid intermediate IB (13.1 g, yield: 74%).

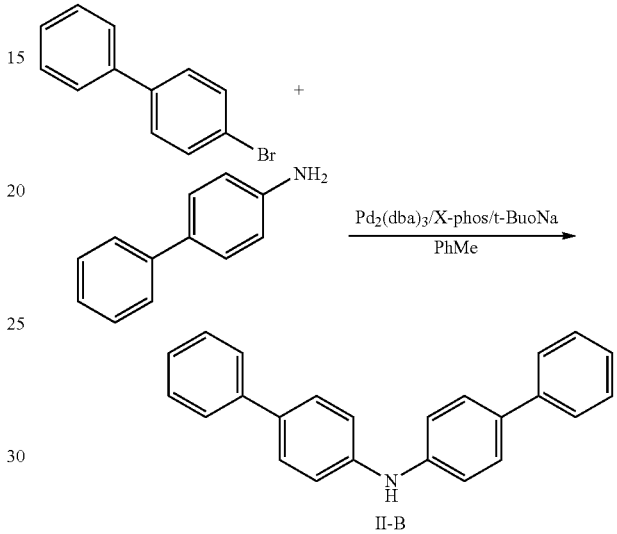

4-bromobiphenyl (4 g, 17.16 mmol), 4-aminobiphenyl (2.96 g, 17.50 mmol), tris(dibenzylideneacetone)dipalladium (0.16 g, 0.17 mmol), 2-dicyclohexylphosphino-2',4',6'-triisopropylbiphenyl (0.16 g, 0.34 mmol), and sodium tert-butoxide (2.47 g, 25.74 mmol) were added to methylbenzene (30 mL), and a resulting system was heated to 108° C. and stirred for 2 h under nitrogen atmosphere. A resulting reaction solution was cooled to room temperature and then washed with water until neutral. The separated organic phase was dried with anhydrous magnesium sulfate and filtered to obtain filtrate, the filtrate was concentrated in a vacuuo to obtain a crude product. The crude product was purified by silica gel column chromatography and eluted with a mixture of dichloromethane (DCM)/n-heptane (v/v=1:5) to obtain a solid intermediate II-B (3.1 g, yield: 56.3%).

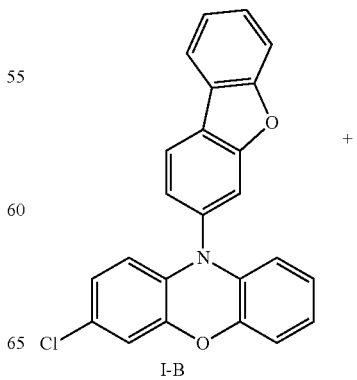

-continued

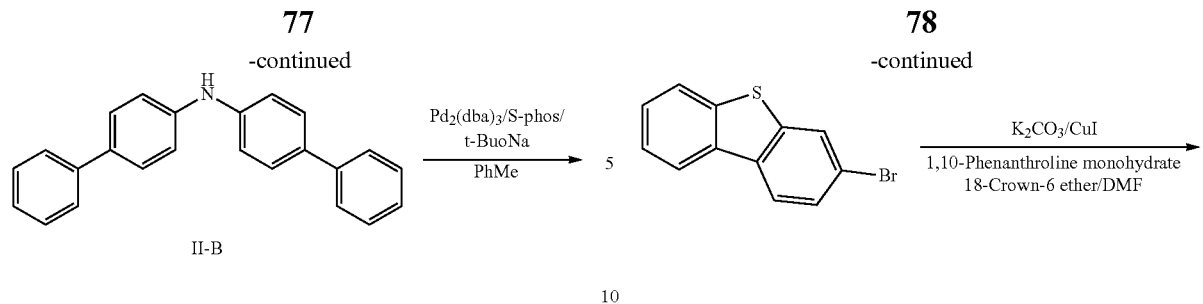

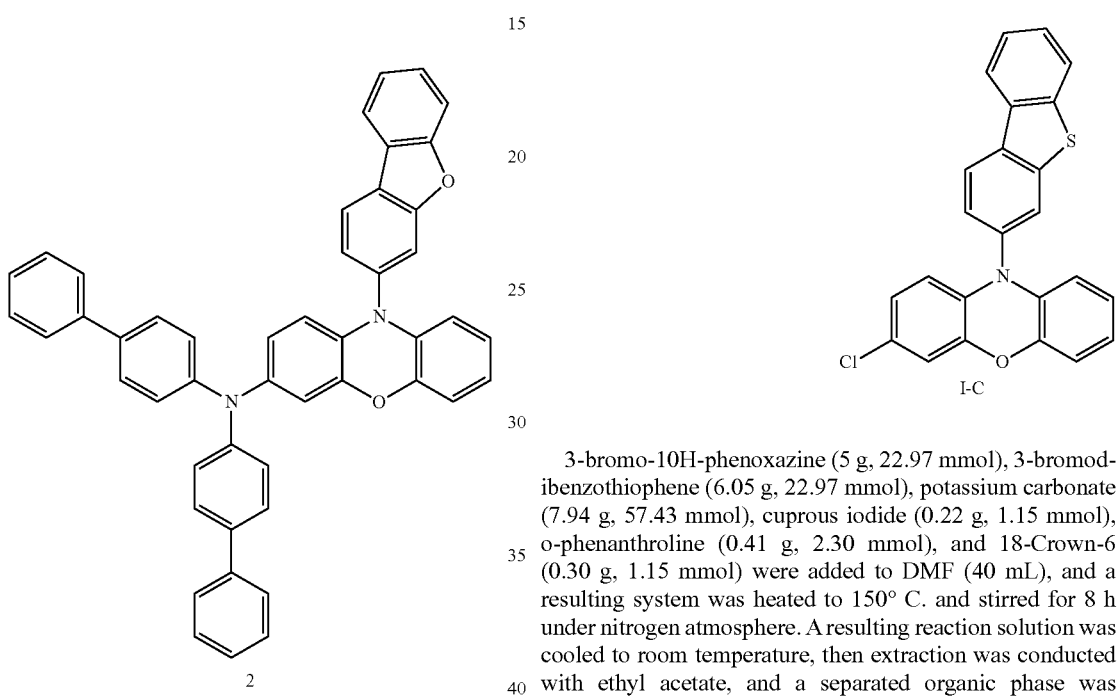

The intermediate I-B (3.5 g, 9.12 mmol), the intermediate II-B (2.99 g, 9.30 mmol), tris(dibenzylideneacetone)dipalladium (0.08 g, 0.09 mmol), 2-dicyclohexylphosphino-2',6'-dimethoxybiphenyl (0.07 g, 0.18 mmol), and sodium tert-butoxide (1.31 g, 13.68 mmol) were added to methylbenzene (30 mL), and a resulting system was heated to 108° C. and stirred for 1 h under nitrogen atmosphere. A resulting reaction solution was cooled to room temperature and then washed with water. The separated organic phase was dried with anhydrous magnesium sulfate and filtered to obtain filtrate, the filtrate was concentrated in a vacuuo to obtain a residue. The residue was purified by flash silica gel column chromatography and the eluent concentrated in a vacuuo to obtain a crude product; and a crude product was purified by recrystallization using a mixture of methylbenzene and n-heptane to obtain a solid compound 2 (4.31 g, yield: 71%). LC-MS (ESI, pos. ion): m/z=669.2 [M+H]+.
Synthesis of Compound 3:

3-bromo-10H-phenoxazine (5 g, 22.97 mmol), 3-bromodibenzothiophene (6.05 g, 22.97 mmol), potassium carbonate (7.94 g, 57.43 mmol), cuprous iodide (0.22 g, 1.15 mmol), o-phenanthroline (0.41 g, 2.30 mmol), and 18-Crown-6 (0.30 g, 1.15 mmol) were added to DMF (40 mL), and a resulting system was heated to 150° C. and stirred for 8 h under nitrogen atmosphere. A resulting reaction solution was cooled to room temperature, then extraction was conducted with ethyl acetate, and a separated organic phase was washed with water until neutral. The separated organic phase was dried over anhydrous magnesium sulfate and filtered to obtain filtrate, the filtrate was concentrated in a vacuuo to obtain a crude product. The crude product was purified by recrystallization using n-heptane to obtain a solid intermediate I-C (7.6 g, yield: 82%).

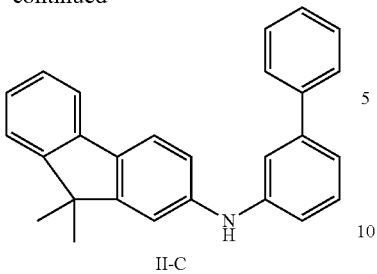

II-C 2-amino-9,9-dimethylfluorene (4 g, 17.31 mmol), 3-bromobiphenyl (3.70 g, 17.65 mmol), tris(dibenzylideneacetone)dipalladium (0.16 g, 0.17 mmol), 2-dicyclohexylphosphino-2',4',6'-triisopropylbiphenyl (0.17 g, 0.35 mmol), and sodium tert-butoxide (2.49 g, 25.96 mmol) were added to methylbenzene (30 mL), and a resulting system was heated to 108° C. and stirred for 4 h under nitrogen atmosphere. A resulting reaction solution was cooled to room temperature and then washed with water until neutral. The separated organic layer was dried over anhydrous magnesium sulfate and filtered to obtain filtrate, the filtrate was concentrated in a vacuuo to obtain a residue. The residue was purified by silica gel column chromatography, and eluted with a mixture of DCM and n-heptane (v/v=1/5) to obtain a solid intermediate II-C (5.7 g, yield: 90%).

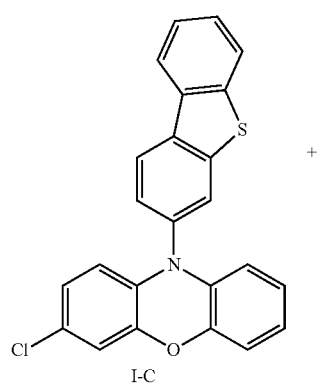

I-C

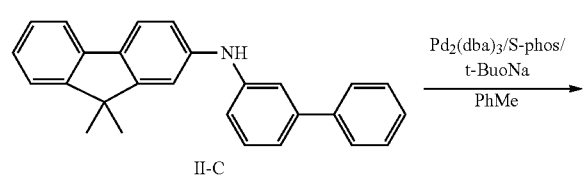

II-C

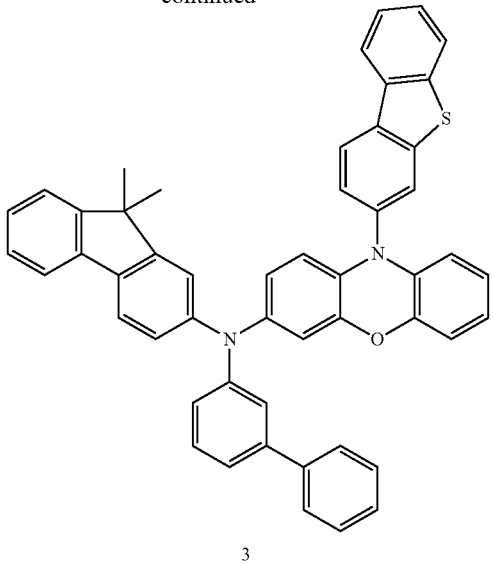

3

The intermediate I-C (3.5 g, 8.75 mmol), the intermediate II-C (3.23 g, 8.93 mmol), tris(dibenzylideneacetone)dipalladium (0.08 g, 0.09 mmol), 2-dicyclohexylphosphino-2',6'-dimethoxybiphenyl (0.07 g, 0.18 mmol), and sodium tert-butoxide (1.26 g, 13.13 mmol) were added to methylbenzene (30 mL), and a resulting system was heated to 108° C. and stirred for 1 h under nitrogen atmosphere. A resulting reaction solution was cooled to room temperature and then washed with water. The separated organic layer was dried over anhydrous magnesium sulfate, and filtered to obtain a filtrate, and the filtrate was passed through a short silica gel column, and eluent is concentrated in a vacuuo to obtain a residue. The residue was purified by recrystallization using a mixture of methylbenzene and n-heptane system to obtain a solid compound 3 (4.9 g, yield: 77%). LC-MS (ESI, pos. ion): m/z=725.3 [M+H]$^+$.

H$^1$NMR data of compound 3: $^1$HNMR (400 MHz, CDCl$_3$): 8.23 (d, 1H), 8.05 (d, 1H), 7.95 (d, 1H), 7.82-7.85 (m, 2H), 6.84-7.55 (m, 20H), 6.67 (d, 1H), 6.59 (s, 1H), 6.45 (t, 3H), 6.42-6.56 (m, 5H), 6.24 (d, 1H).

The compounds of the disclosure can all be prepared according to the process described in the general synthesis scheme. Detailed synthesis processes of some compounds are exemplarily given below.

Synthesis of Compounds 9 and 10:

The compounds 9 and 10 each were synthesized by the same synthesis process as compound 2 in the synthesis example except that 3-chloro-10H-phenothiazine was used instead of 3-chloro-10H-phenoxazine, the raw material 1 in the table below was used instead of 4-bromobiphenyl, and the raw material 2 in the table below was used instead of 4-aminobiphenyl.

| Compound | Raw material 1 | Raw material 2 | Compound | Yield/% | MS (m/z) [M + H]+ |
|---|---|---|---|---|---|
| Compound 9 | 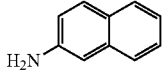 | 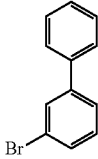 | 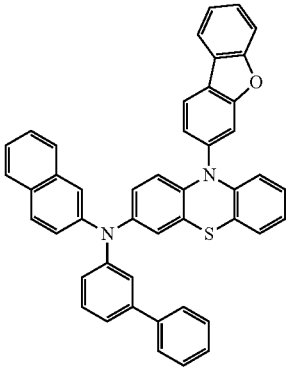 | 54 | 659.2 |
| Compound 10 | 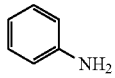 | 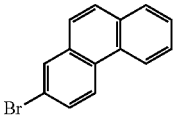 | 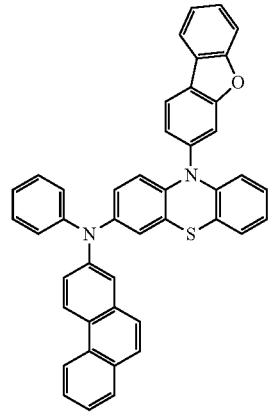 | 46 | 633.2 |

Synthesis of Compound 11:

The compound 11 was synthesized by the same synthesis process as compound 3 in the synthesis example except that 3-chloro-10H-phenothiazine was used instead of 3-chloro-10H-phenoxazine, the raw material 1 in the table below was used instead of 2-amino-9,9-dimethylfluorene, and the raw material 2 in the table below was used instead of 3-bromo-biphenyl.

| Compound | Raw material 1 | Raw material 2 | Compound | Yield/% | MS (m/z) [M + H]+ |
|---|---|---|---|---|---|
| Compound 11 | | | 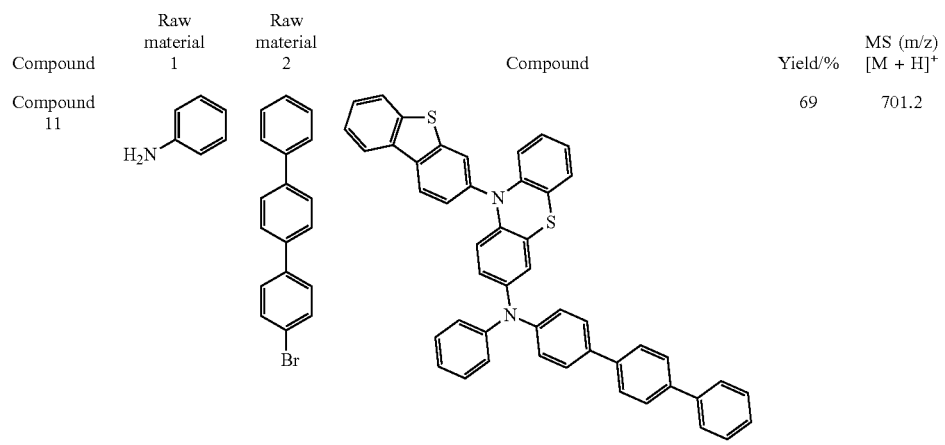 | 69 | 701.2 |

Synthesis of Compound 14:
The compound 14 was synthesized by the same synthesis process as compound 9 in the synthesis example except that 3-bromo-9-phenylcarbazole was used instead of 2-bromo-9,9-dimethylfluorene

| Compound | Raw material 1 | Compound | Yield/% | MS (m/z) [M + H]+ |
|---|---|---|---|---|
| Compound 14 | | 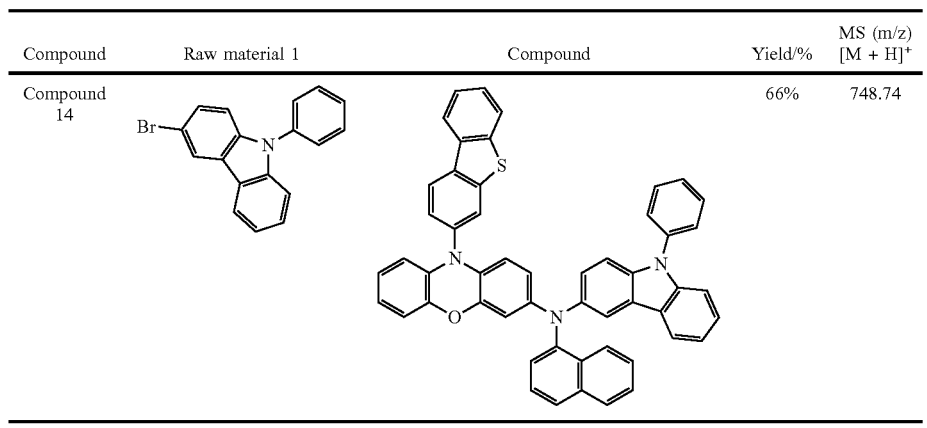 | 66% | 748.74 |

Synthesis of Compound 16:
The compound 16 was synthesized by the same synthesis process as compound 2 in the synthesis example except that 2-naphthylamine was used instead of 4-aminobiphenyl, and 3-bromodibenzofuran was used instead of 4-bromobiphenyl

| Compound | Raw material 1 | Raw material 2 | Compound | Yield/% | MS (m/z) [M + H]+ |
|---|---|---|---|---|---|
| Compound 16 | | | 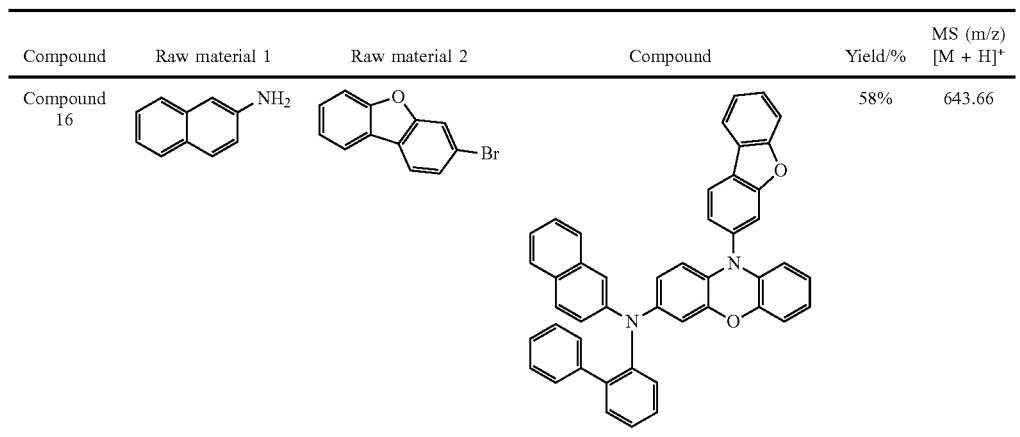 | 58% | 643.66 |

Synthesis of Compound 17:

The compound 17 was synthesized by the same synthesis process as compound 3 in the synthesis example except that 3-bromobiphenyl was used instead of 2-bromo-9,9-dimethylfluorene.

| Compound | Raw material 1 | Raw material 2 | Compound | Yield/% | MS (m/z) [M + H]+ |
|---|---|---|---|---|---|
| Compound 17 | 3-bromobiphenyl | 3-aminobiphenyl | (structure) | 70% | 685.90 |

Synthesis of Compound 18:

The compound 18 was synthesized by the same synthesis process as compound 3 in the synthesis example except that 3-chloro-10H-phenothiazine was used instead of 3-chloro-10H-phenoxazine, and bromobenzene was used instead of 2-bromo-9,9-dimethylfluorene

| Compound | Raw material 1 | Raw material 2 | Compound | Yield/% | MS (m/z) [M + H]+ |
|---|---|---|---|---|---|
| Compound 18 | 3-chloro-10H-phenothiazine | bromobenzene | (structure) | 68% | 625.24 |

Synthesis of Compound 19:

The compound 19 was synthesized by the same synthesis process as compound 2 in the synthesis example except that 2-chloro-9,9-dimethyl-9,10-dihydroacridine was used instead of 3-chloro-10H-phenoxazine

| Compound | Raw material 1 | Compound | Yield/% | MS (m/z) [M + H]⁺ |
|---|---|---|---|---|
| Compound 19 | | | 60% | 695.80 |

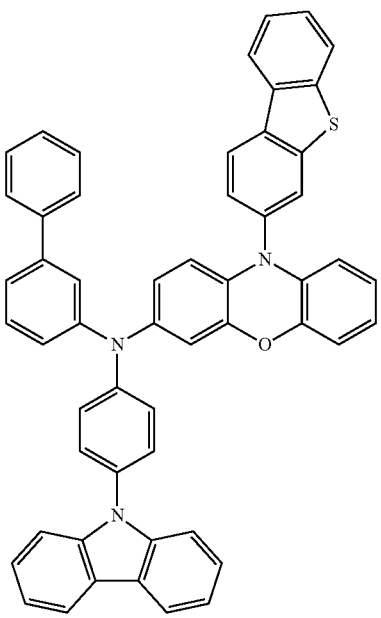

Synthesis of Compound 154:

The compound 154 was synthesized by the same synthesis process as compound 3 except that phenylamine was used instead of 2-amino-9,9-dimethylfluorene, and 2-bromonaphthalene was used instead of 3-bromobiphenyl, with a total yield of 42%. LC-MS (ESI, pos. ion): m/z=583.2 [M+H]⁺.

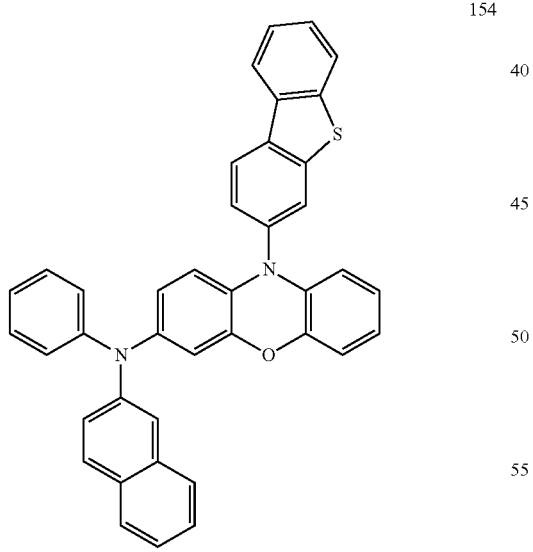

Synthesis of Compound 258:

The compound 258 was synthesized by the same synthesis process as compound 14 except that 3-aminobiphenyl was used instead of 1-aminonaphthalene, and 4-carbazolylphenyl was used instead of 3-bromo-9-phenylcarbazole, with a total yield of 38%. LC-MS (ESI, pos. ion): m/z=774.2 [M+H]⁺.

Synthesis of Compound 327:

The compound 327 was synthesized by the same synthesis process as compound 3 except that bromobenzene was used instead of 3-bromobiphenyl, with a total yield of 49%. LC-MS (ESI, pos. ion): m/z=665.2 [M+H]⁺.

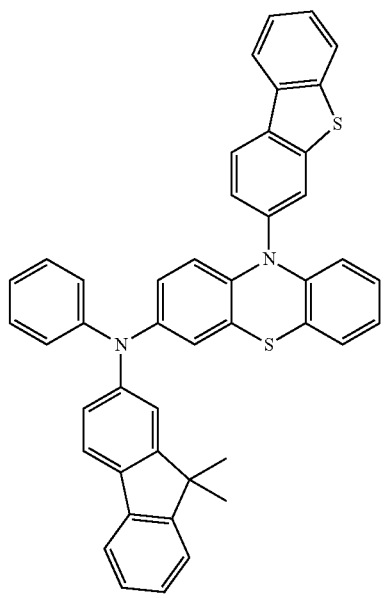

327

Synthesis of Compound 329:

The compound 329 was synthesized by the same synthesis process as compound 327 except that 2-aminodibenzothiophene was used instead of 2-amino-9,9-dimethylfluorene, with a total yield of 56%. LC-MS (ESI, pos. ion): m/z=655.1 [M+H]$^+$.

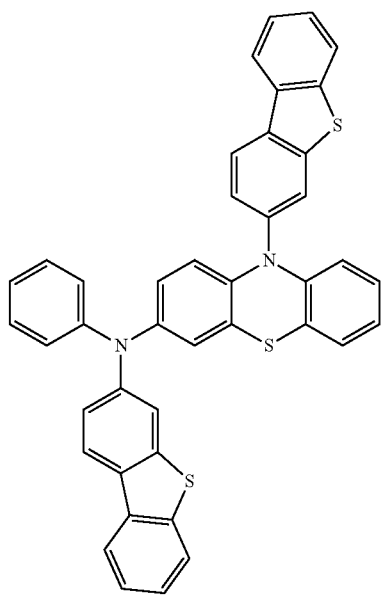

329

Synthesis of Compound 352:

The compound 352 was synthesized by the same synthesis process as compound 17 except that 4-aminobiphenyl was used instead of 2-amino-9,9-dimethylfluorene, and 4-bromobiphenyl was used instead of 3-bromobiphenyl, with a total yield of 63%. LC-MS (ESI, pos. ion): m/z=685.1 [M+H]$^+$.

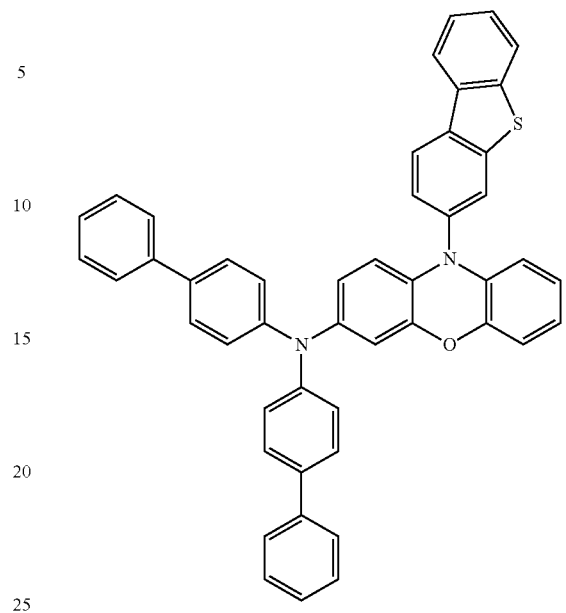

352

365

Synthesis of Compound 365:

The compound 365 was synthesized by the same synthesis process as compound 2 except that phenylamine was used instead of 4-aminobiphenyl, and 4-bromoterphenyl was used instead of 4-bromobiphenyl, with a total yield of 43%. LC-MS (ESI, pos. ion): m/z=685.2 [M+H]$^+$.

Synthesis of Compound 386:

The compound 386 was synthesized by the same synthesis process as compound 2 except that 4-aminoquinoline was used instead of 4-aminobiphenyl, and 2-bromo-4-phenyldibenzofuran was used instead of 4-bromobiphenyl, with a total yield of 35%. LC-MS (ESI, pos. ion): m/z=734.2 [M+H]$^+$.

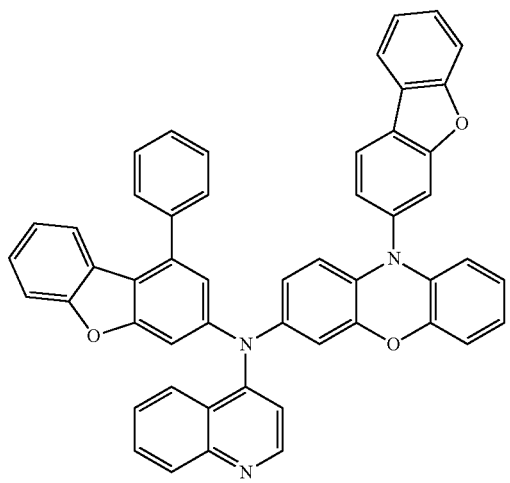

Other compounds in the disclosure can all be prepared according to the above synthesis methods, and all required raw materials can be purchased.

(2) EXAMPLES OF THE ELECTRONIC ELEMENT, AND ELECTRONIC DEVICE

In the disclosure, organic electroluminescent devices (OLEDs) is one kind of electronic elements. The disclosure also provides an electronic element. As shown in FIG. 1, a photoelectric conversion device, which belongs to the electronic element, can include an anode 1 and a cathode 5 arranged oppositely, and a functional layer 3 arranged between the anode 1 and the cathode 5, wherein the functional layer 3 can include the nitrogen-containing compound according to any one of the above embodiments.

A material of the anode 1 can be a metal, an alloy, or a metal oxide, such as nickel, platinum, vanadium, chromium, copper, zinc, gold, or an alloy thereof, and zinc oxide, indium oxide, indium tin oxide (ITO), or indium zinc oxide (IZO). The material of the anode 1 may also be a composition, such as ZnO:Al, $SnO_2$:Sb, and conductive polymers (poly(3-methylthiophene), poly[3,4-(ethylene-1,2-dioxy) thiophene] (PEDT), polypyrrole (PPy), and polyaniline (PANI)). Of course, The material of the anode 1 is not limited to the above materials, and can be other materials, which will not be listed here. Preferably, the material of the anode 1 is ITO.

A material of the cathode 5 may be a metal or an alloy, such as magnesium, calcium, sodium, potassium, titanium, aluminum, silver, or an alloy thereof, and may also be a multi-layer material, such as LiF/Al, Liq/Al, $LiO_2$/Al, LiF/Ca, LiF/Al, and $BaF_2$/Ca. Of course, the material of the cathode 5 is not limited to the above materials, which will not be listed here. Preferably, the material of the cathode 5 is aluminum.

The functional layer 3 can be used for the transport of electrons and holes and can provide a area for recombination or separation of electrons and holes, which can include the nitrogen-containing compound according to any one of the embodiments of the disclosure. In an embodiment, the electronic element of the disclosure is an OLED, and the nitrogen-containing compound is used to form one or more layers in the functional layer 3 of the OLED to improve the luminous efficiency of the electronic element and extend the service life of the electronic element. For example, the functional layer 3 includes an hole transport layer (HTL) 31, and the HTL 31 includes the nitrogen-containing compound according to any one of the embodiments of the disclosure. The nitrogen-containing compound can be used to increase mobility of holes, such that the number of holes matches the number of electrons in the functional layer, thereby increasing the recombination probability of holes and electrons and improving the luminous efficiency of the electronic element.

In an embodiment, the functional layer 3 further include a electroluminescent layer (EML) 33 and an electron transport layer (ETL) 35, wherein the EML 33 is arranged at a side of the HTL 31 away from the anode 1, and the ETL 35 is arranged between the EML 33 and the cathode 5. The electronic element includes an anode 1, an HTL 31, an EML 33, an ETL 35, and a cathode 5 that are arranged in a stack.

The organic EML 33 of the photoelectric conversion device is composed of a single light-emitting material, or includes a host material and a guest material. Optionally, the organic EML 33 is composed of a host material and a guest material, wherein holes injected into the organic EML 33 and electrons injected into the organic EML 33 can recombine in the organic EML 33 to form excitons, the excitons transfer energy to the host material, and then the host material transfers energy to the guest material, such that the guest material can emit light.

The host material of the organic EML 33 is a metal chelate compound, a bisstyryl derivative, an aromatic amine derivative, a dibenzofuran derivative, or the like, which is not particularly limited in the disclosure. In an embodiment of the disclosure, the host material of the organic EML 33 is 4,4'-N,N'-dicarbazole-biphenyl (CBP). In another embodiment of the disclosure, the host material of the organic EML 33 is 9-(1-naphthyl)-10-(2-naphthyl)anthracene ($\alpha$, $\beta$-ADN).

The guest material of the organic EML 33 is a compound with a condensed aryl ring or a derivative thereof, a compound with a heteroaryl ring or a derivative thereof, an aromatic amine derivative, or the like, which is not particularly limited in the disclosure. In an embodiment of the disclosure, the guest material of the organic EML 33 is $Ir(piq)_2$ (acac). In another embodiment of the disclosure, the guest material of the organic EML 33 is BD-1.

The ETL 35 of the photoelectric conversion device has a single-layer structure or a multi-layer structure, which includes one or more electron transport materials. The electron transport materials may be benzimidazole derivatives, oxadiazole derivatives, quinoxaline derivatives, or other electron transport materials, which is not particularly limited in the disclosure. For example, in an embodiment of the disclosure, the ETL 35 is composed of 4,7-diphenyl-2,9-bis(4-(1-phenyl-1H-benzo[d]imidazol-2-yl)phenyl)-1,10-phenanthroline (DBimiBphen) and 8-hydroxyquinolinolato-lithium (LiQ).

Moreover, the electronic element of the embodiment in the disclosure may further include an electron blocking layer (EBL) 32, an hole injection layer (HIL) 2, and an electron injection layer (EIL) 4, wherein the EBL 32 can be arranged at the side of the EML 33 away from the cathode 5; the HIL 2 can be arranged between the anode 1 and the HTL 31; and the EIL 4 can be arranged between the cathode 5 and the ETL 35. For example, the electronic element is an OLED.

Figure 2:
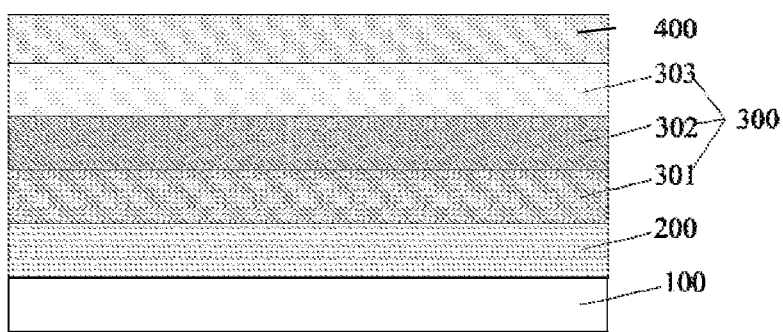
FIG. 2 is a schematic structure diagram of a solar cell according to an embodiment of the disclosure.

In other embodiments, as shown in FIG. 2, the electronic element is a solar cell, such as an organic solar cell, including a cathode 400, an anode 200, and a functional layer 300, wherein the functional layer 300 can be arranged between the cathode 400 and the anode 200. The functional layer 300 can include the nitrogen-containing compound according to any one of the embodiments of the disclosure, which can increase mobility of excitons. In an embodiment, the functional layer 300 includes an electron transport layer (ETL) 303, a hole transport layer (HTL) 301, and a photosensitive active layer 302. An anode 200 is formed on a substrate 100, and the anode 200 is a thin film attached to the substrate 100. The HTL 301 can be formed on a surface of the anode 200 away from the substrate 100; the photosensitive active layer 302 can be formed on a surface of the HTL 301 away from the anode 200; an ETL 303 can be formed on a surface of the photosensitive active layer 302 away from the HTL 301, and the ETL 303 may include the nitrogen-containing compound according to any one of the embodiments of the disclosure; and a cathode 400 may be formed on a surface of the ETL 303 away from the photosensitive active layer 302. When the solar cell is irradiated by sunlight, electrons in the photosensitive active layer 302 gain energy and jump to produce excitons. With the assistance of the ETL 303 and the HTL 301, electrons move towards the cathode 400 and holes move towards the anode 200, such that a potential difference can be generated between the cathode 400 and the anode 200 of the solar cell, thereby realizing the power generation function. In this process, the compound of the disclosure can enhance mobility of electrons in the ETL 303 to avoid recombination of electrons and holes, thereby increasing the number of electrons transported towards the cathode 400, increasing an open-circuit voltage of the solar cell, and improving the photoelectric conversion efficiency.

Figure 3:
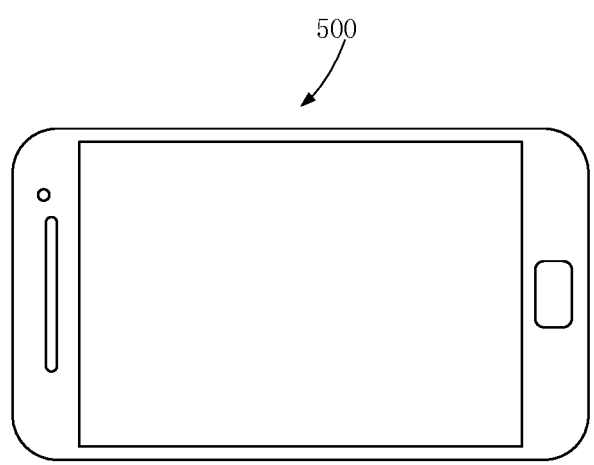
FIG. 3 is a schematic diagram of the electronic device according to an embodiment of the disclosure.

The disclosure also provides an electronic device 500. As shown in FIG. 3, the electronic device 500 may include the electronic element according to any one of the above embodiments, and its beneficial effects and specific details can refer to the above electronic element, which will not be repeated here. For example, the electronic device 500 can be a display, an array substrate, a photovoltaic (PV) module, or can be another device, which will not be listed here. For example, the electronic device can be a screen of a mobile phone, a screen of a camera, or a screen of a computer, or can be another device or equipment, which is not specifically limited here.

With an OLED as an example, the OLED of the disclosure will be described in detail below through examples. However, the following examples are only illustrations of the disclosure, and do not limit the disclosure.

(3) PRODUCTION AND EVALUATION EXAMPLES OF OLED

Example 1

A substrate including a Ag alloy light-reflecting layer and an ITO anode (with a thickness of 15 nm) of the OLED was cut into a size of 40 mm (length)×40 mm (width)×0.7 mm (thickness), then the substrate was processed through photolithography into an experimental substrate with a cathode 5, an anode 1, and an insulating layer pattern, and then the experimental substrate was subjected to surface treatment with UV-ozone and $O_2:N_2$ plasma to increase a work function of the anode 1, and then cleaned with an organic solvent to remove scum and oil stains on the surface of the experimental substrate. The organic solvent can be ethanol, acetone, or isopropanol. Of course, the organic solvent can also be other organic solvents, which will not be listed here. It should be noted that the ITO substrate can also be cut into another size according to actual needs, and the disclosure has no specific limitations on the size of the ITO substrate.

A compound hexaazatriphenylene hexacarbonitrile (HAT-CN) (with a structural formula shown below) was vacuum-deposited on the experimental substrate (anode 1) to form an HIL 2 with a thickness of 100 Å; and then a compound 2 was vacuum-deposited on the HIL 2 to form an HTL 31 with a thickness of 1,000 Å.

A compound 4,4',4"-tris(carbazol-9-yl)-triphenylamine (TCTA) (with a structural formula shown below) was vapor-deposited on the HTL 31 to form an EBL 32 with a thickness of 100 Å.

A compound 4,4'-N,N'-dicarbazole-biphenyl (CBP) (with a structural formula shown below, as a host material) and Ir(piq)$_2$(acac) (with a structural formula shown below, in a weight ratio of 3%) were vapor-deposited on the EBL 32 to form an EML 33 with a thickness of 330 Å.

1,3,5-tris(1-phenyl-1H-benzimidazol-2-yl)benzene (TPBi) (with a structural formula shown below) and LiQ (with a structural formula shown below) were vapor-deposited on the EML 33 in a weight ratio of 1:1 to form an ETL with a thickness of 350 Å.

Silver (Ag) and magnesium (Mg) were vapor-deposited on the ETL in a weight ratio of 10:1 to form a cathode 5 with a thickness of 120 Å.

A compound CP-1 (with a structural formula shown below) was vapor-deposited on the cathode 5 to form an organic capping layer (CPL) with a thickness of 650 Å.

An electronic element obtained after the vapor deposition was completed was encapsulated with UV curing resin in a nitrogen glove box (with strictly-controlled water and oxygen contents) to prevent the electronic element from being corroded by external moisture or other substances.

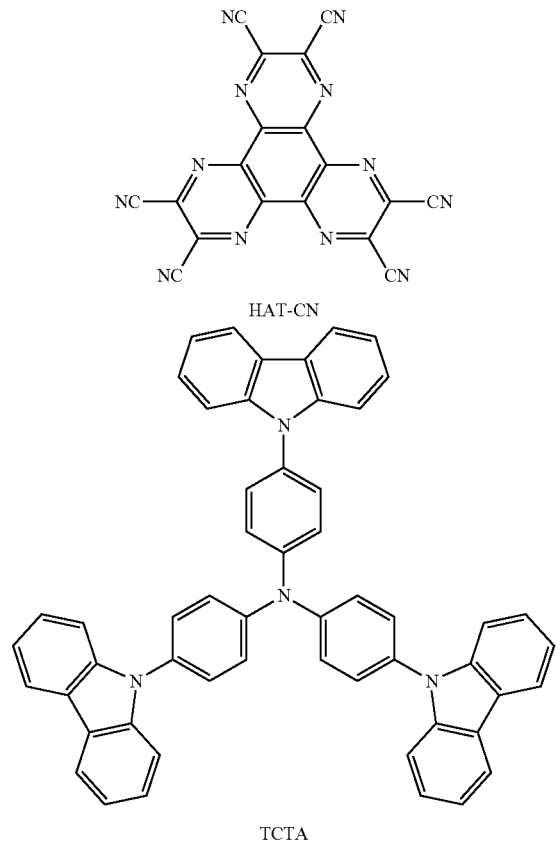

-continued

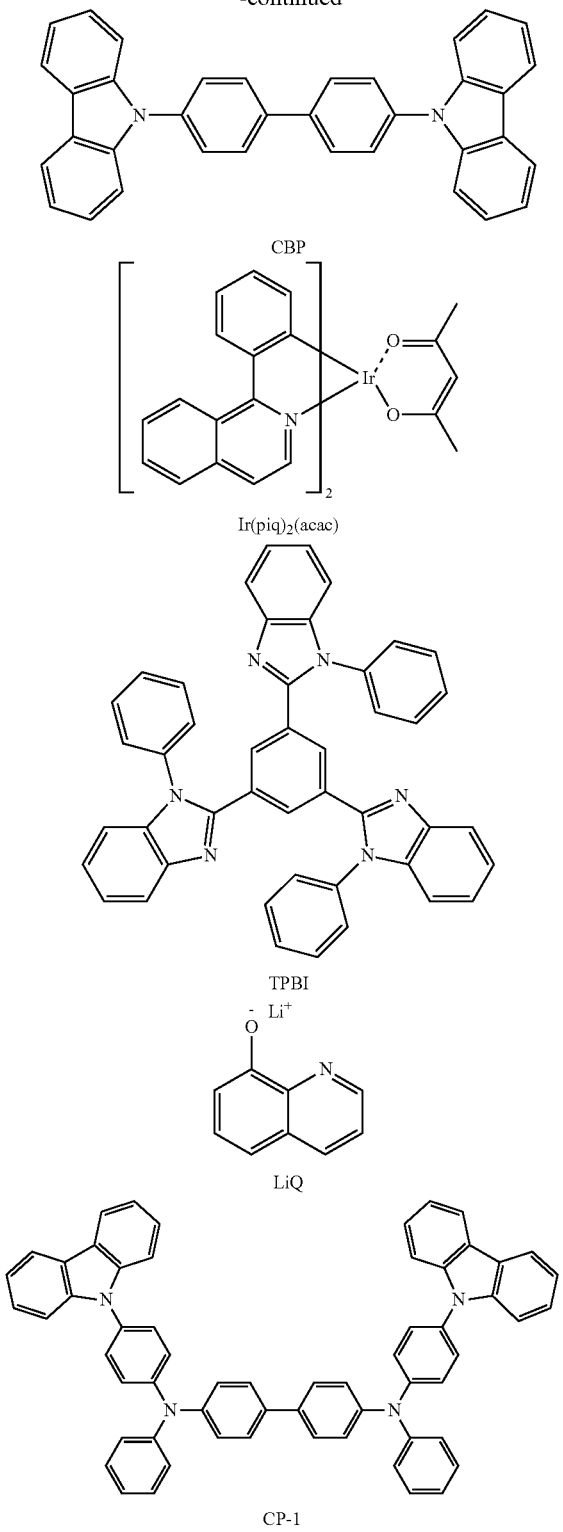

CBP

Ir(piq)₂(acac)

TPBI

LiQ

CP-1

Examples 2 to 17

OLEDs were produced in the same method as in Example 1, except that the compounds shown in Table 1 were used respectively when the HTL 31 was formed.

Comparative Examples 1 to 3

In Comparative Examples 1 to 3, OLEDs were produced in the same method as in Example 1, except that compounds A, B, and C were respectively used instead of compound 1 to form the HTL 31. Structures of compounds A, B, and C were as follows:

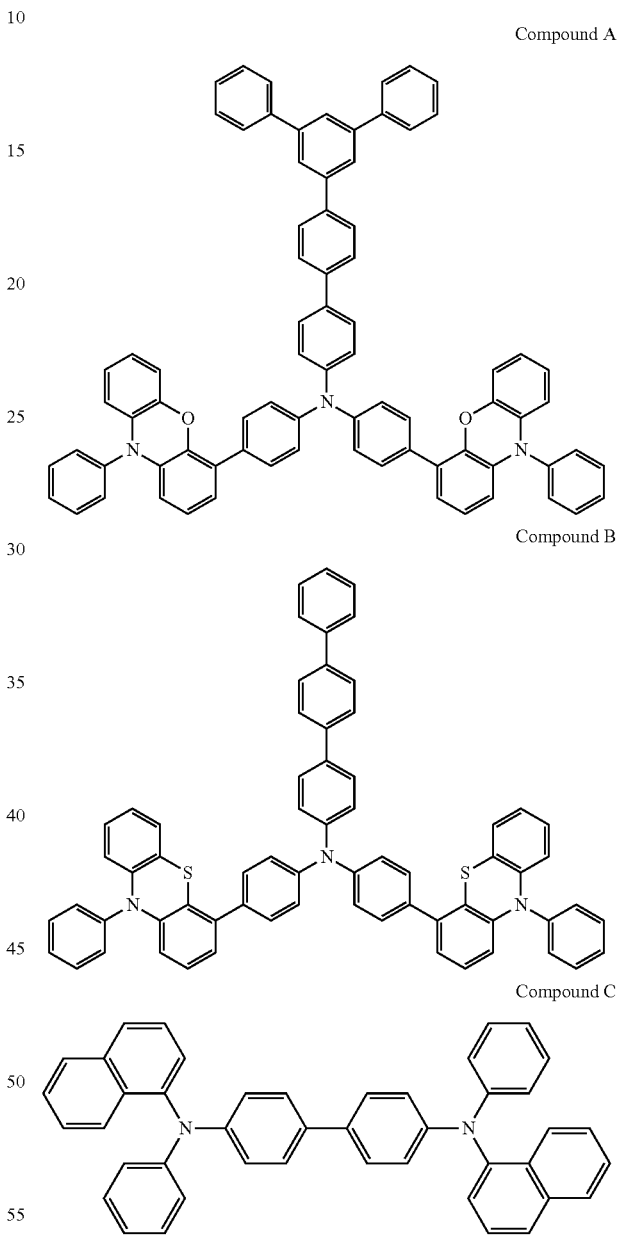

That is, in Comparative Example 1, compound A was used to produce an OLED; in Comparative Example 2, compound B was used to produce an OLED; and in Comparative Example 3, compound C was used to produce an OLED. The performance of the OLEDs was shown in Table 1.

The IVL (current, voltage, and luminance) data were test results at 10 mA/cm², and the T95 service life was also a test result at a current density of 10 mA/cm².

TABLE 1

Performance of the OLEDs in Examples 1 to 20 and Comparative Examples 1 to 3

| Example | HTL | Cd/A 10 mA/cm² | Chromaticity coordinate CIEx | Chromaticity coordinate CIEy | T95 (hr) 10 mA/cm² |
|---|---|---|---|---|---|
| Example 1 | Compound 2 | 21.3 | 0.673 | 0.325 | 738 |
| Example 2 | Compound 3 | 22.4 | 0.672 | 0.323 | 734 |
| Example 3 | Compound 9 | 22.2 | 0.674 | 0.328 | 698 |
| Example 4 | Compound 10 | 22.5 | 0.672 | 0.324 | 665 |
| Example 5 | Compound 11 | 22.0 | 0.673 | 0.333 | 705 |
| Example 6 | Compound 14 | 22.6 | 0.679 | 0.330 | 728 |
| Example 7 | Compound 16 | 24.1 | 0.671 | 0.327 | 712 |
| Example 8 | Compound 17 | 23.9 | 0.675 | 0.329 | 731 |
| Example 9 | Compound 18 | 22.8 | 0.674 | 0.323 | 709 |
| Example 10 | Compound 19 | 23.3 | 0.673 | 0.324 | 660 |
| Example 11 | Compound 154 | 21.6 | 0.671 | 0.326 | 675 |
| Example 12 | Compound 258 | 22.5 | 0.675 | 0.322 | 736 |
| Example 13 | Compound 327 | 22.1 | 0.670 | 0.321 | 738 |
| Example 14 | Compound 329 | 23.5 | 0.674 | 0.324 | 658 |
| Example 15 | Compound 352 | 21.2 | 0.672 | 0.332 | 722 |
| Example 16 | Compound 365 | 21.8 | 0.671 | 0.330 | 695 |
| Example 17 | Compound 386 | 21.5 | 0.671 | 0.328 | 689 |
| Comparative Example 1 | Compound A | 16.8 | 0.674 | 0.325 | 420 |
| Comparative Example 2 | Compound B | 17.5 | 0.673 | 0.326 | 534 |
| Comparative Example 3 | Compound C | 17.3 | 0.671 | 0.325 | 472 |

It can be seen from the results in Table 1 that, compared with Comparative Examples 1, 2, and 3 respectively using compounds A, B, and C as HTL, the examples using the compound of the disclosure as HTL show significantly-improved luminous efficiency and service life, wherein the luminous efficiency can reach 21.2 cd/A to 23.9 cd/A, which is 26.1% to 42.3% higher than the luminous efficiency of Comparative Example 1 (16.8 cd/A), 21.1% to 36.6% higher than the luminous efficiency of Comparative Example 2 (17.5 cd/A), and 22.5% to 38.1% higher than the luminous efficiency of Comparative Example 3 (17.3 cd/A). The compound of the disclosure, when used as HTL, can increase the luminous efficiency of the OLED by more than 20% (up to 42%).

Moreover, OLEDs using the compound of the disclosure as HTL also show a significantly-improved T95 service life, wherein the T95 service life can reach 658 h to 738 h, which is 56.7% to 75.7% higher than the T95 service life of Comparative Example 1 (420 h), 23.3% to 38.2% higher than the T95 service life of Comparative Example 2 (534 h), and 39.4% to 56.3% higher than the T95 service life of Comparative Example 3 (472 h). The compound of the disclosure, when used as HTL, can increase the T95 service life of the OLED by more than 20% (up to 80%).

Therefore, in the nitrogen-containing compound of the disclosure, a dibenzo-five-membered ring is connected with a naphthazinyl to serve as a core structure. Because a naphthazinyl has strong electron-donating ability and a large conjugated system and can increase an electron density of the entire conjugated system, taking the naphthazinyl as a part of the core structure can enhance the electronic tolerance of the material and can also improve the efficiency and service life of the OLED. The combination of the electron-rich naphthazinyl and the dibenzo-five-membered ring enables a large planar structure for the conjugated system, and can effectively increase the hole mobility of the material to promote the hole transport, such that the number of holes and the number of electrons are balanced and the electrons and holes are effectively combined. The nitrogen-containing compound of the disclosure, when used in an HTL of an OLED, can increase the hole mobility in the HTL to promote the hole transport, which helps to improve the efficiency and service life of the OLED.

Those skilled in the art may easily think of other embodiments of the disclosure after considering the specification and practicing the content disclosed herein. The disclosure is intended to cover any variation, use, or adaptive change of the disclosure. The variation, use, or adaptive change follows the general principles of the disclosure and includes common knowledge or conventional technical means in the technical field that are not disclosed by the disclosure. The specification and examples are merely considered as exemplary only, and the real scope and spirit of the disclosure are pointed out by the claims.

What is claimed is:

1. A nitrogen-containing compound, with a general structural formula shown in formula I:

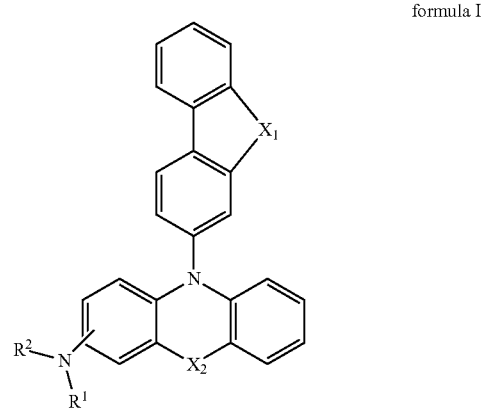

formula I wherein R¹ and R² are the same or different, and are each independently selected from the group consisting of substituted or unsubstituted aryl with 6 to 14 ring-forming carbon atoms, substituted or unsubstituted heteroaryl with 5 to 12 ring-forming carbon atoms; the substituents of R¹ and the substituents of R² are each independently selected from: deuterium, alkyl with 1 to 4 carbon atoms, aryl with 6 to 14 carbon atoms, and heteroaryl with 5 to 12 carbon atoms;

$X_1$ is independently selected from: O and S; and
$X_2$ is independently selected from: O and S.

2. An electronic element, comprising an anode and a cathode that are arranged oppositely, and a functional layer arranged between the anode and the cathode, wherein the functional layer comprises the nitrogen-containing compound according to claim 1.

3. The electronic element according to claim 2, wherein the functional layer comprises a hole transport layer, and the hole transport layer comprises the nitrogen-containing compound.

4. The electronic element according to claim 3, wherein the electronic element is an organic electroluminescent device or a solar cell.

5. An electronic device, comprising the electronic element according to claim 2.

6. A nitrogen-containing compound, with a general structural formula shown in formula I:

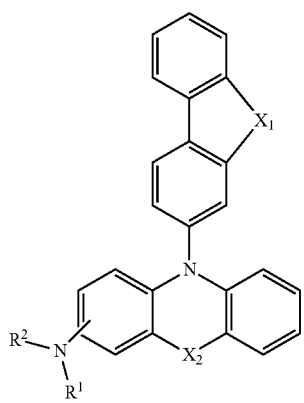

formula I wherein $X_1$ is independently selected from: O and S;
$X_2$ is independently selected from: O and S;
each of R¹ and R² is independently selected from the group consisting of the following groups:

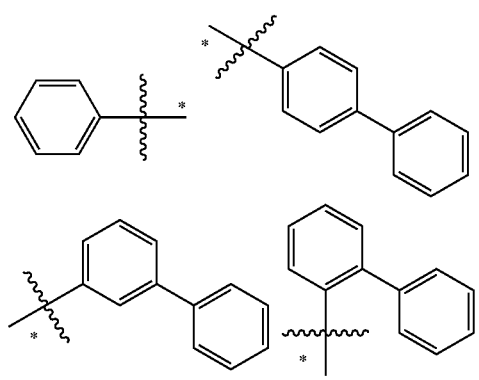

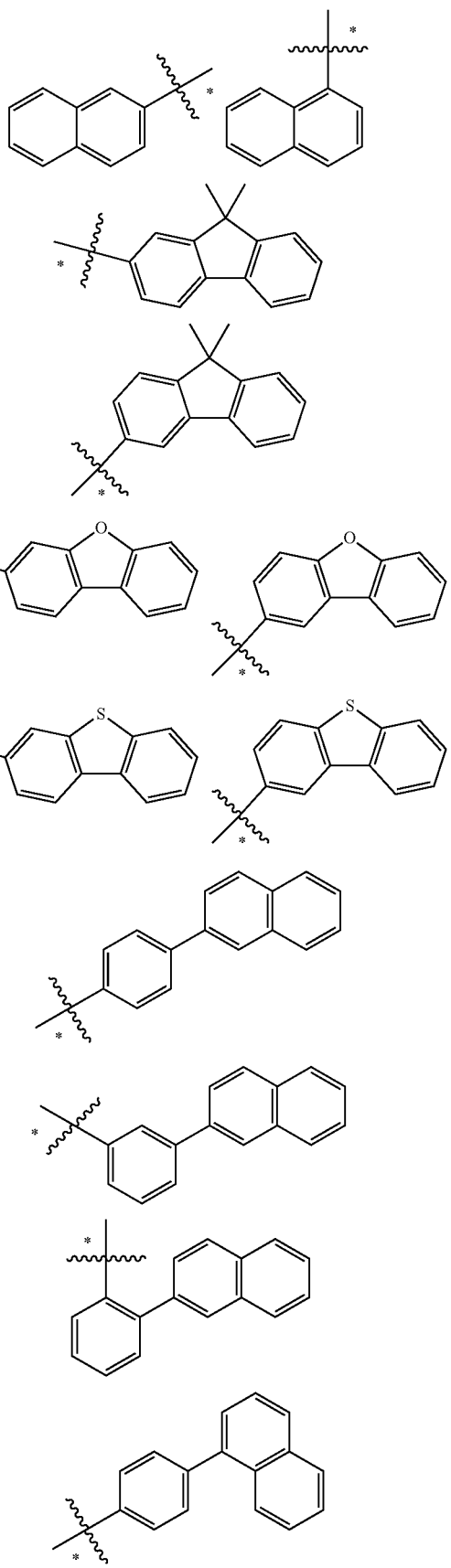

101
-continued
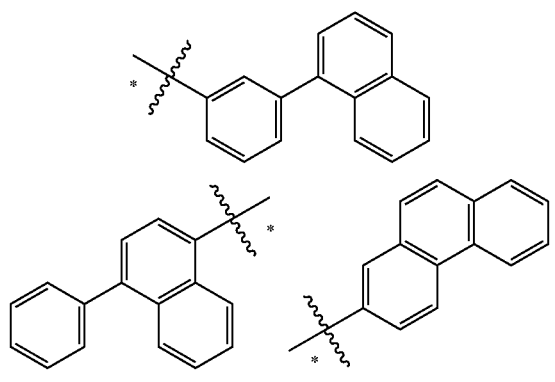
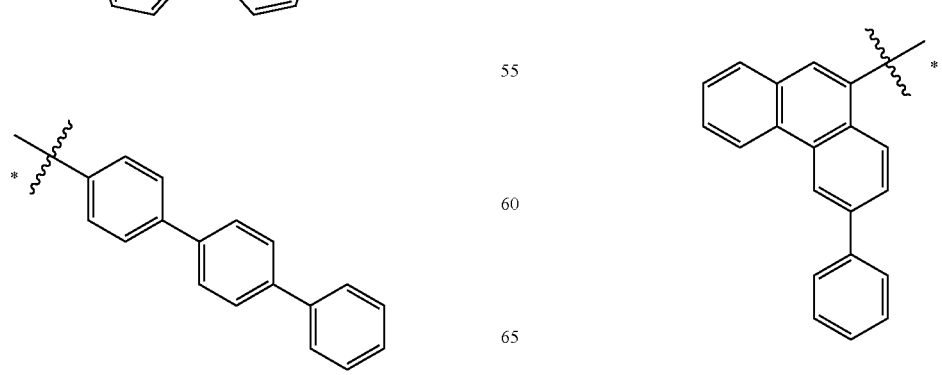
102
-continued
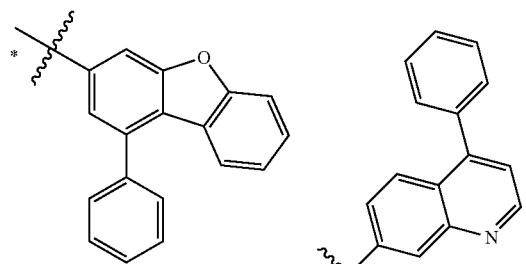
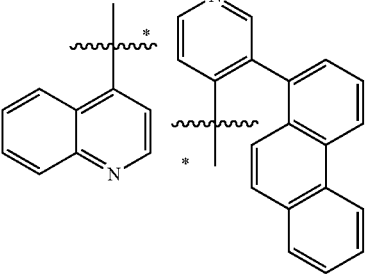
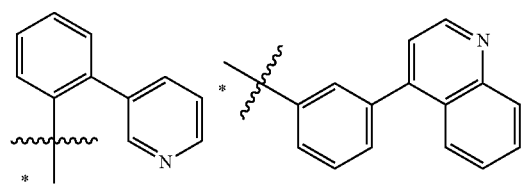
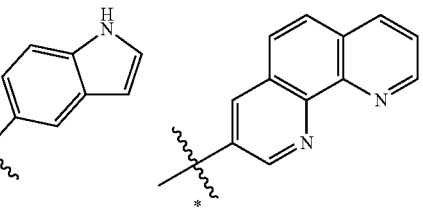
wherein * means a position where the above group is intended to link to

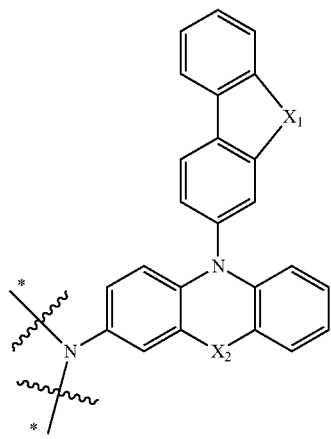

in formula I.

7. An electronic element, comprising an anode and a cathode that are arranged oppositely, and a functional layer arranged between the anode and the cathode,
   wherein the functional layer comprises the nitrogen-containing compound according to claim 6.

8. The electronic element according to claim 7, wherein the functional layer comprises a hole transport layer, and the hole transport layer comprises the nitrogen-containing compound.

9. The electronic element according to claim 8, wherein the electronic element is an organic electroluminescent device or a solar cell.

10. An electronic device, comprising the electronic element according to claim 7.

11. A nitrogen-containing compound, wherein the nitrogen-containing compound is selected from the group consisting of the following nitrogen-containing compounds:

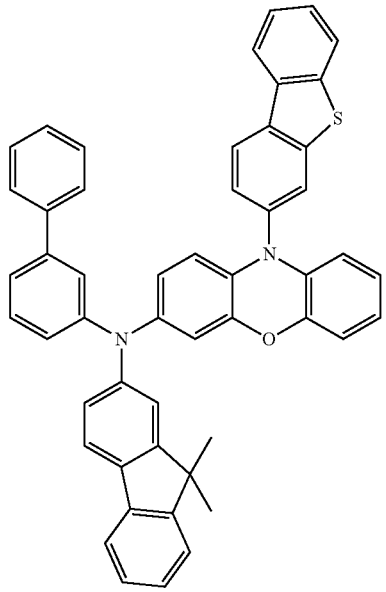

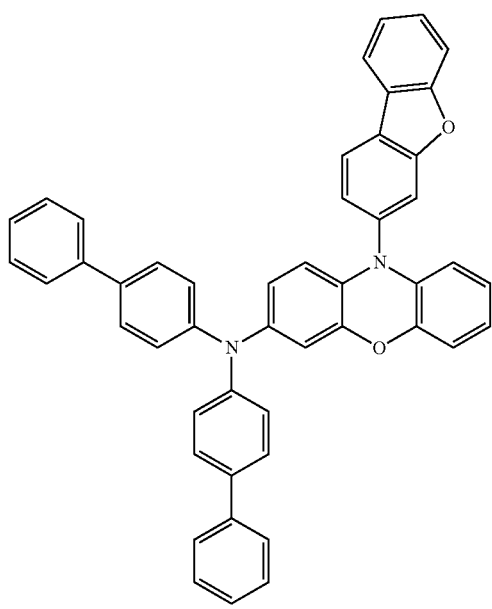 [SMILES: CC1(C)c2ccccc2N(c2ccc3c(c2)oc2ccccc23)c2ccc(N(c3ccc(-c4ccccc4)cc3)c3ccc(-c4ccccc4)cc3)cc21]

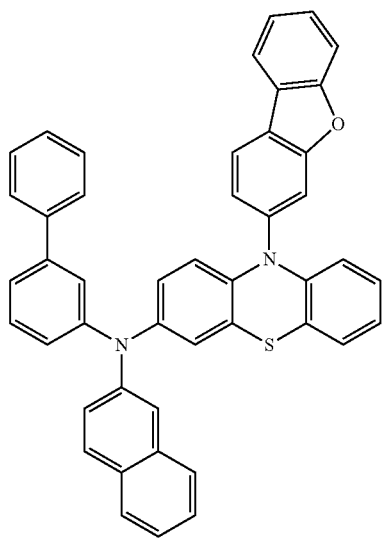

105 -continued
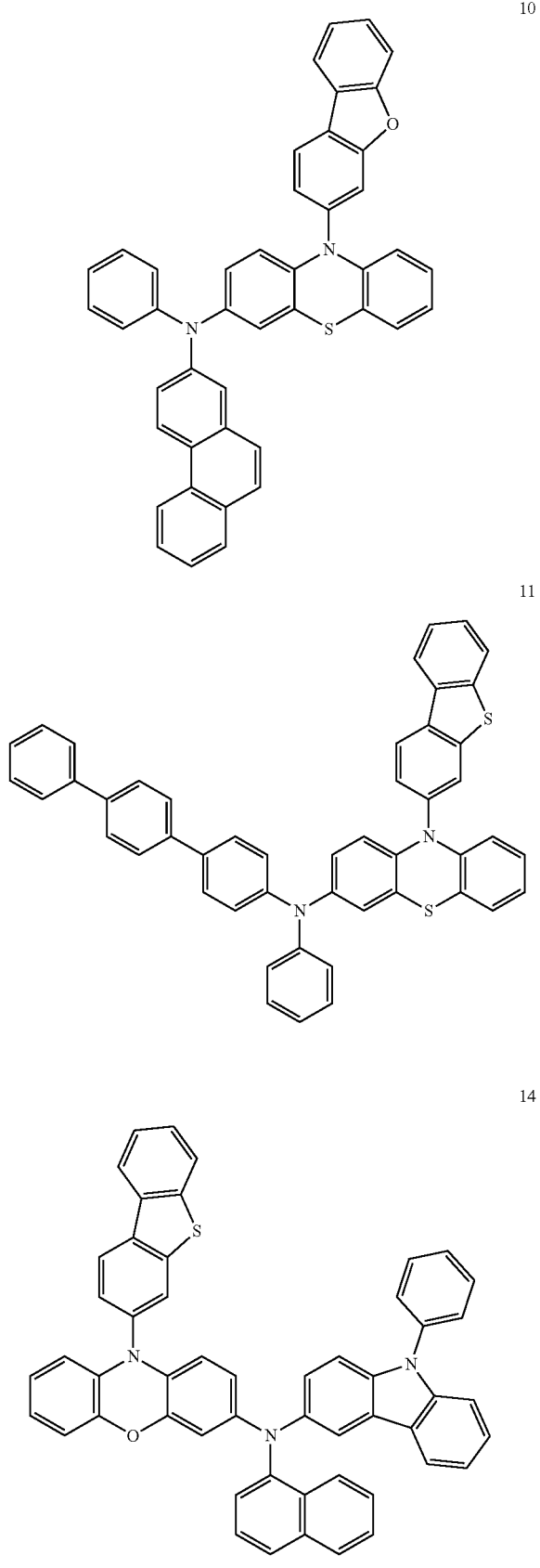 [SMILES: c1ccc(N(c2ccc3c(c2)Sc2ccccc2N3c2ccc3c(c2)oc2ccccc23)c2ccc3c(ccc4ccccc43)c2)cc1 ; c1ccc(-c2ccc(-c3ccc(N(c4ccccc4)c4ccc5c(c4)Sc4ccccc4N5c4ccc5c(c4)sc4ccccc45)cc3)cc2)cc1 ; c1ccc(-n2c3ccccc3c3cc(N(c4ccc5c(c4)Oc4ccccc4N5c4ccc5c(c4)sc4ccccc45)c4cccc5ccccc45)ccc32)cc1]
106 -continued
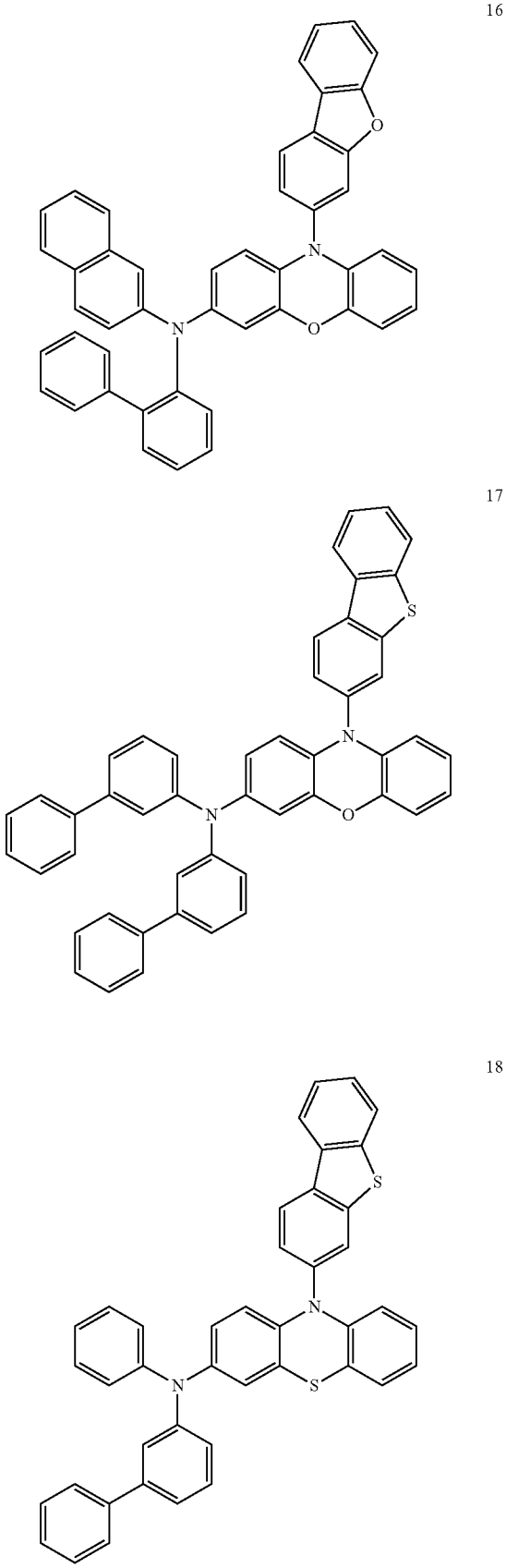 [SMILES: c1ccc(-c2ccccc2N(c2ccc3c(c2)Oc2ccccc2N3c2ccc3c(c2)oc2ccccc23)c2ccc3ccccc3c2)cc1 ; c1ccc(-c2cccc(N(c3cccc(-c4ccccc4)c3)c3ccc4c(c3)Oc3ccccc3N4c3ccc4c(c3)sc3ccccc34)c2)cc1 ; c1ccc(-c2cccc(N(c3ccccc3)c3ccc4c(c3)Sc3ccccc3N4c3ccc4c(c3)sc3ccccc34)c2)cc1]

107
-continued
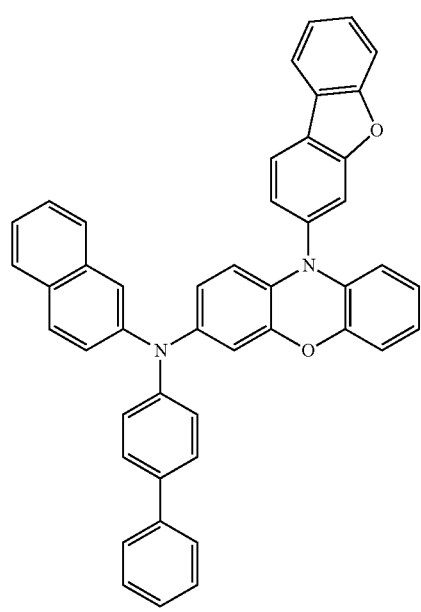
104
108
-continued
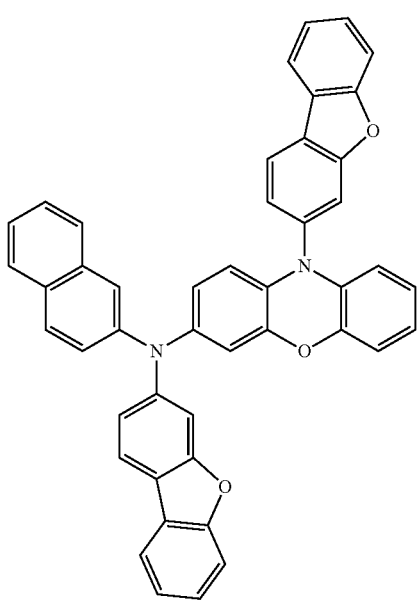
106
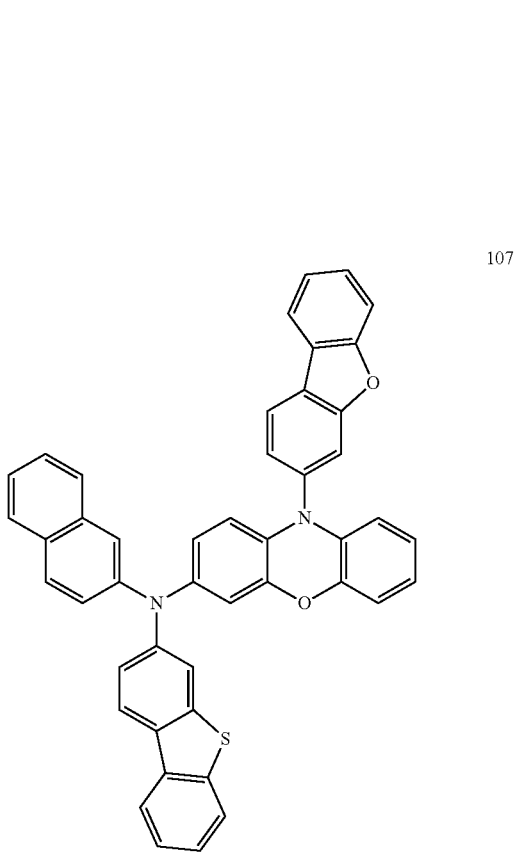
107

108
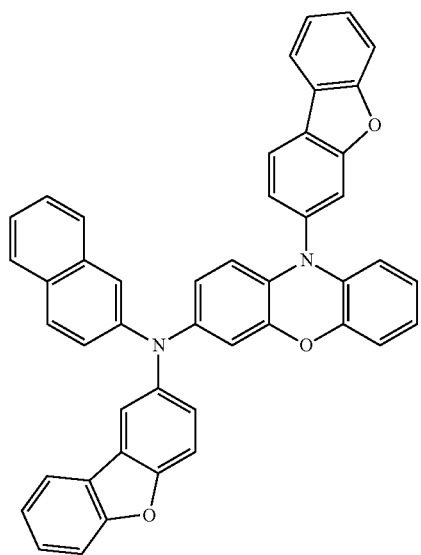
109
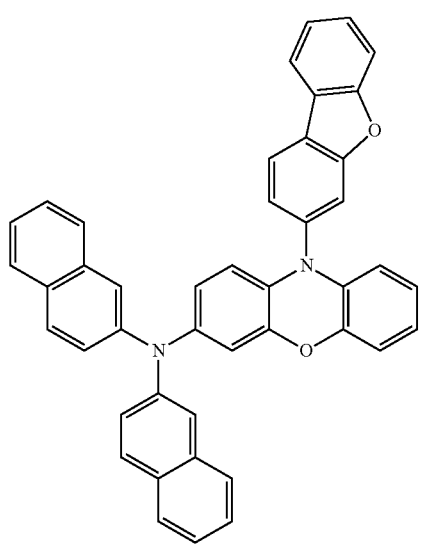
110
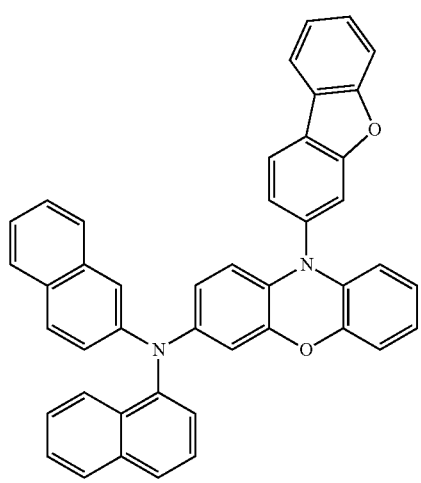
111
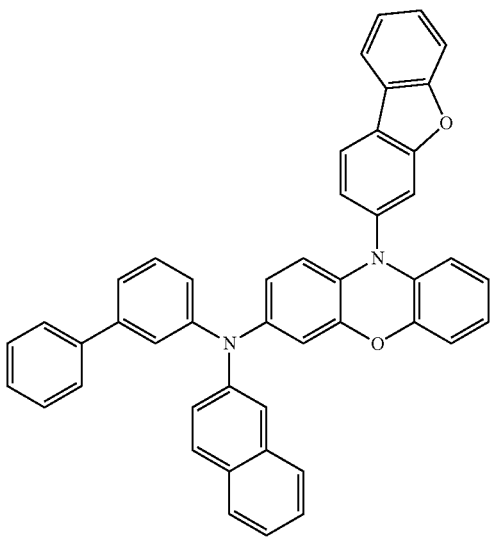
112
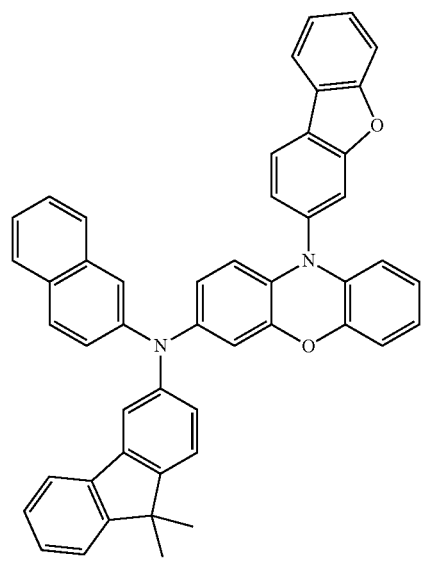
113
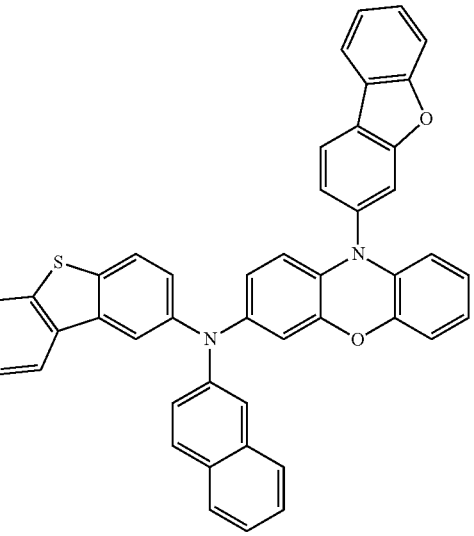

111
-continued
114
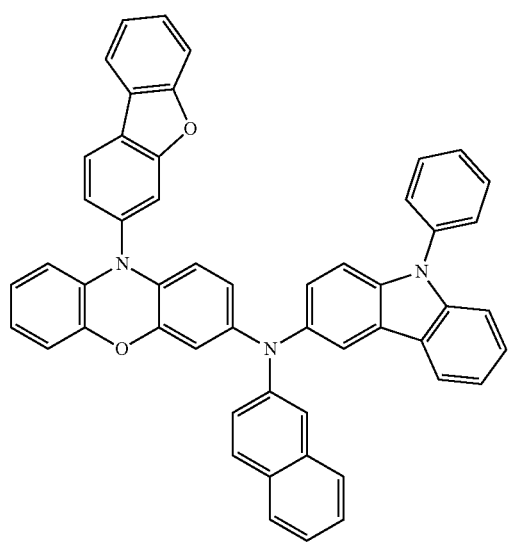
115
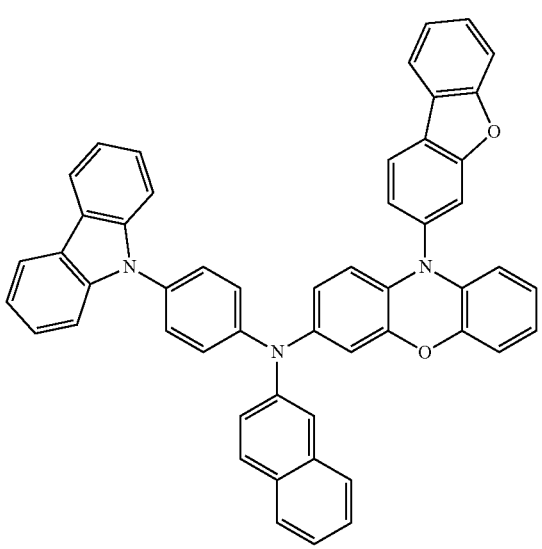
116
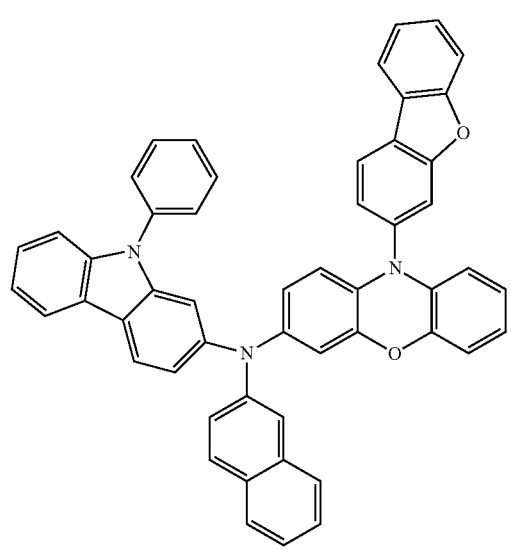
112
-continued
117
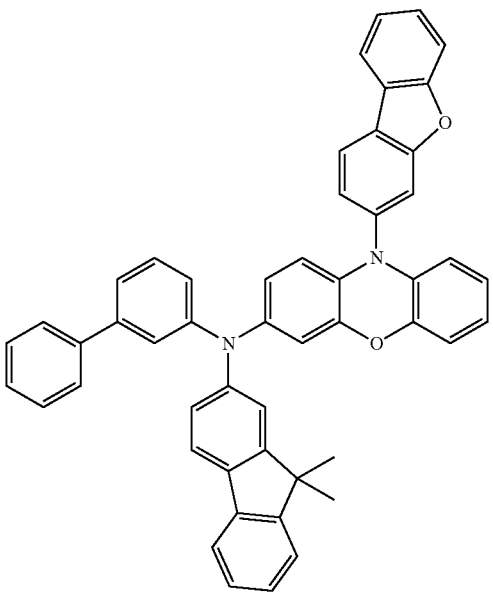
118
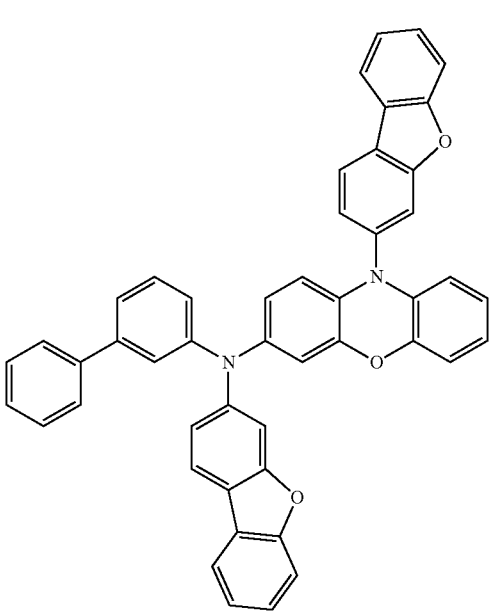

119
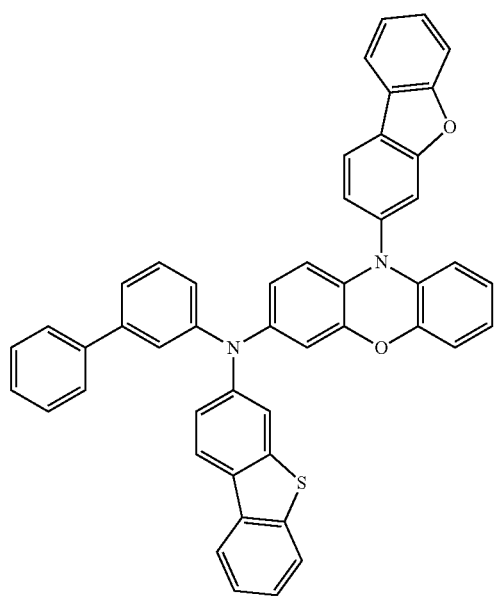
120
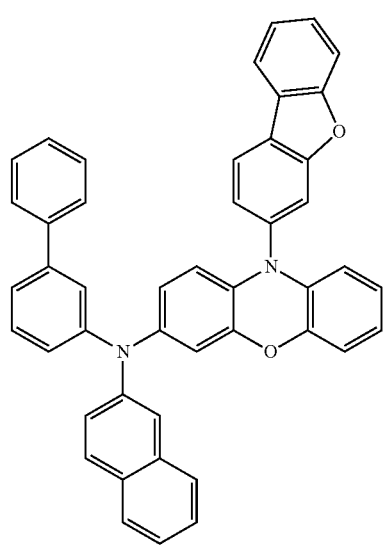
121
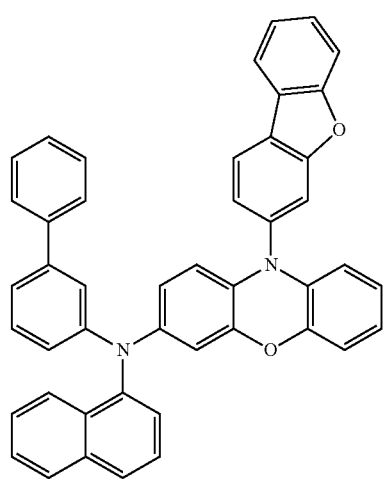
122
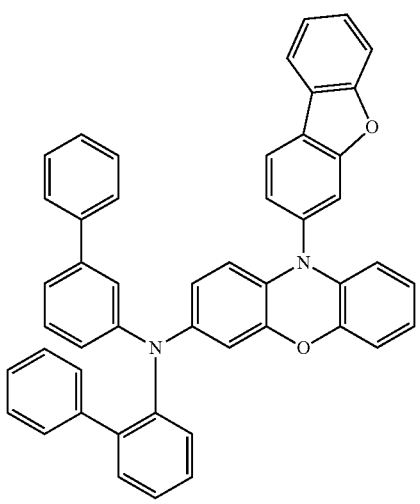
123
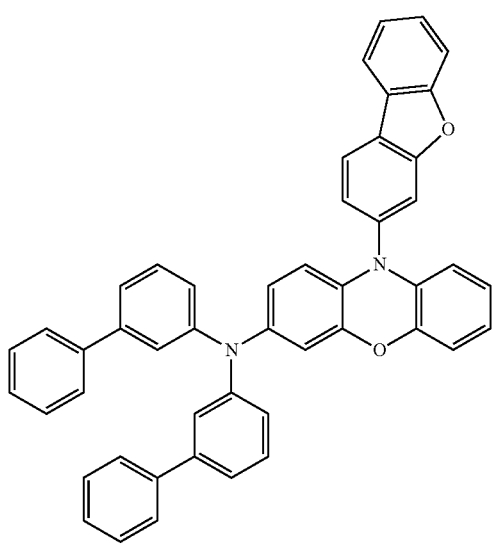
124
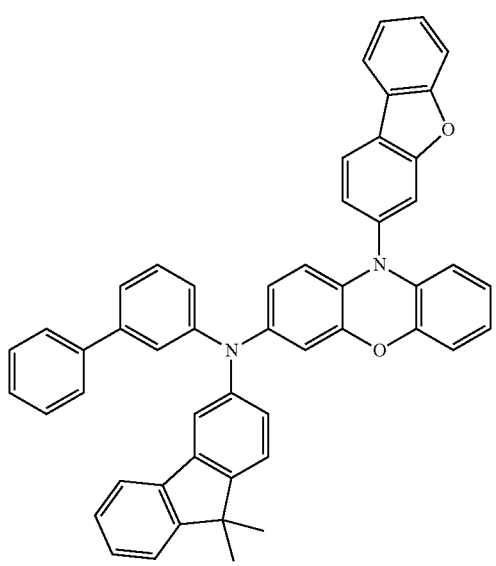

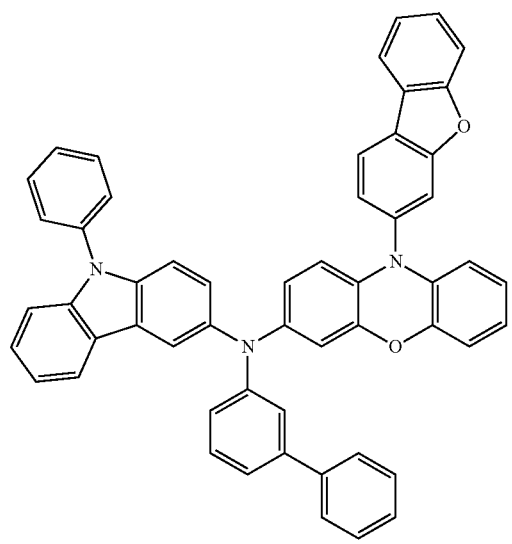
125
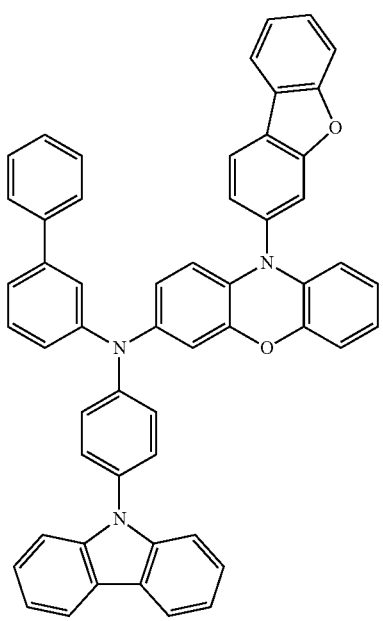
127
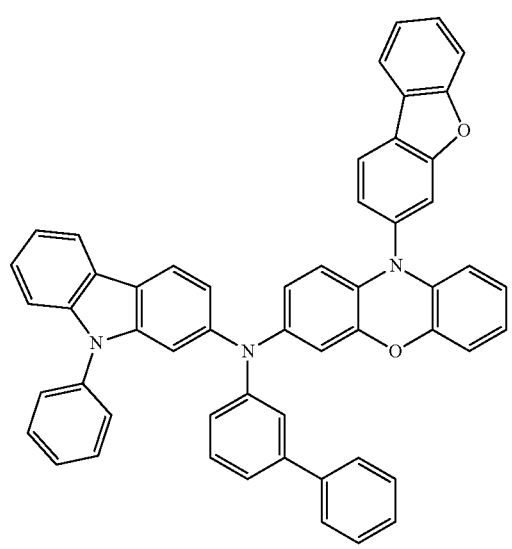
126
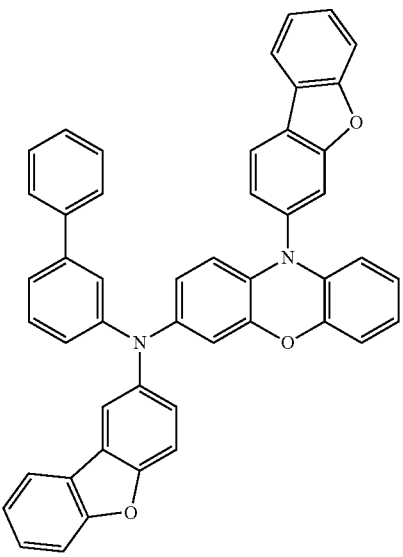
128

129
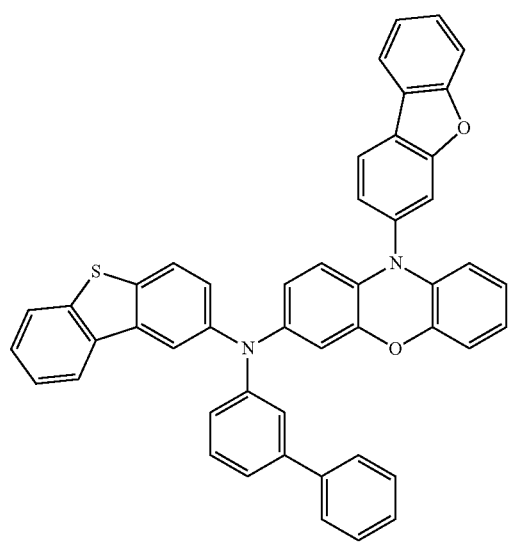
130
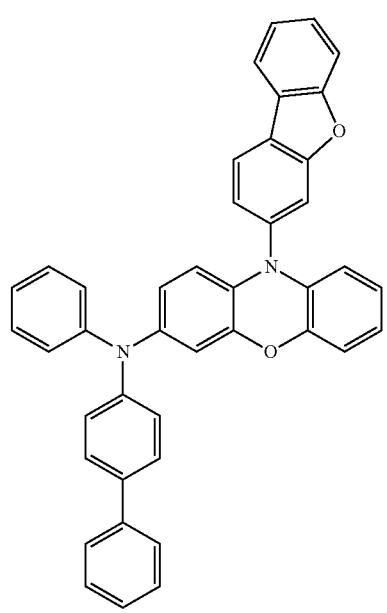
131
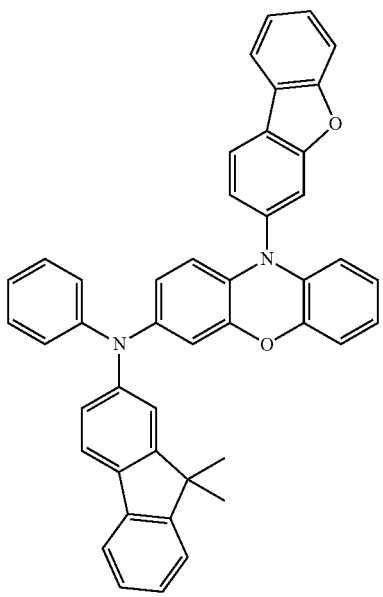
132
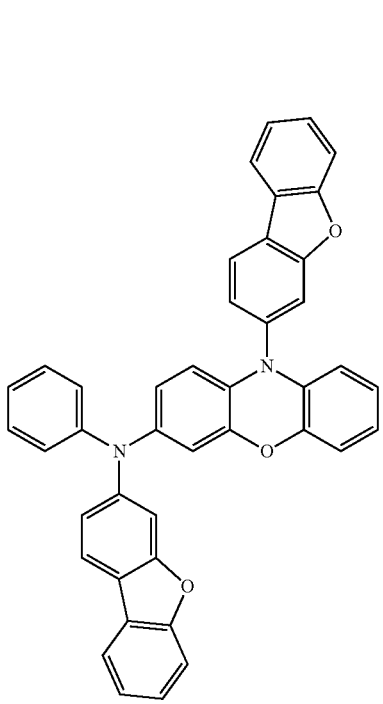

133 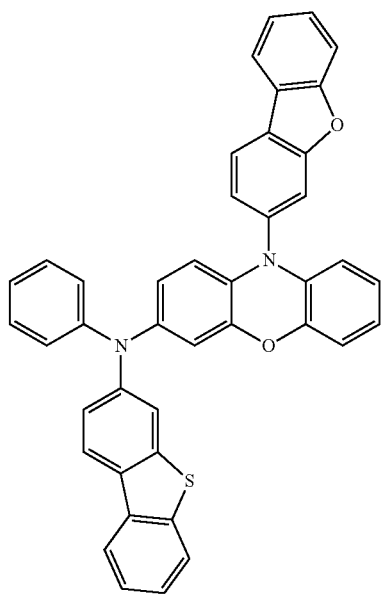
134 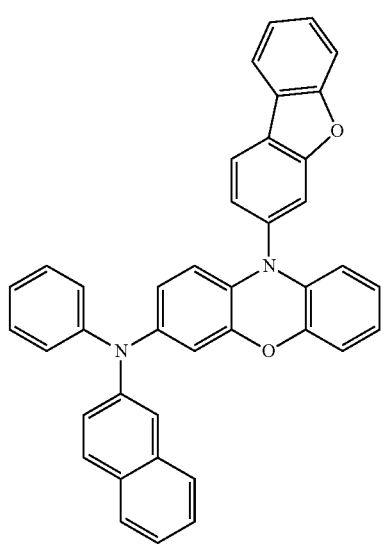
135 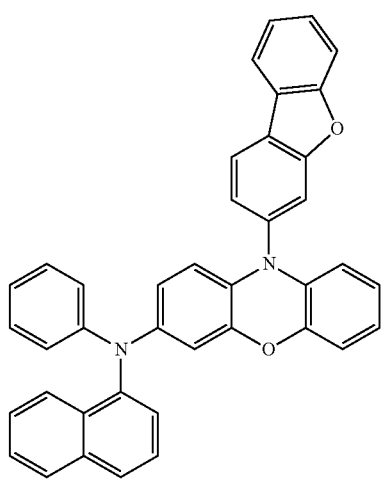
136 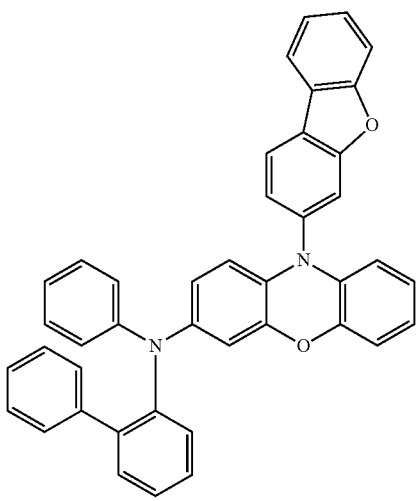
137 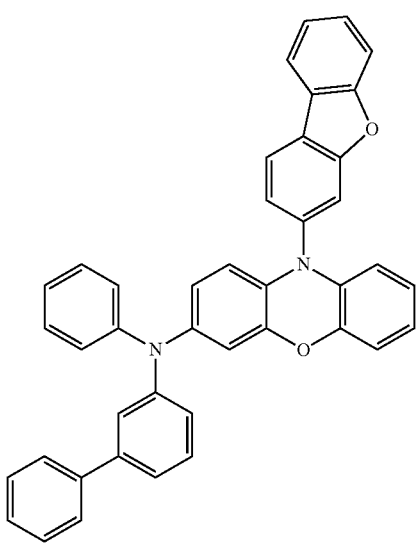
138 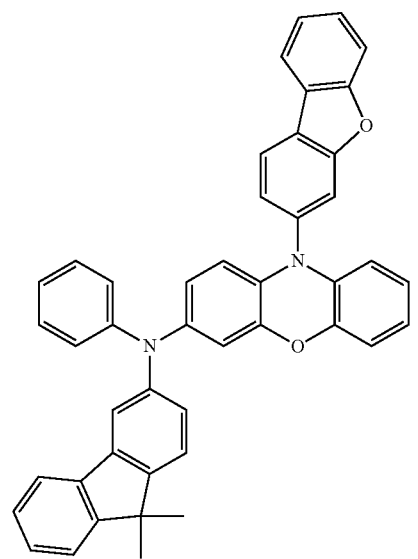

139
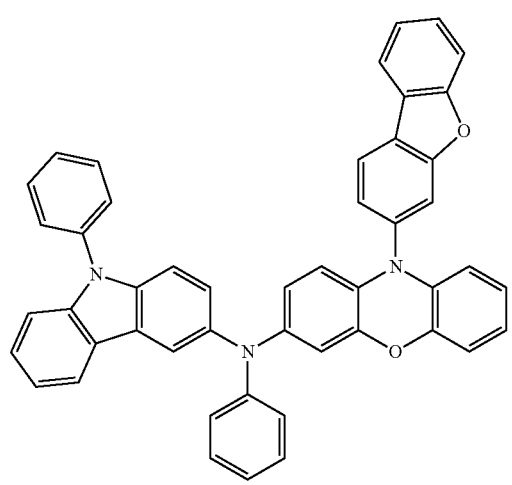
140
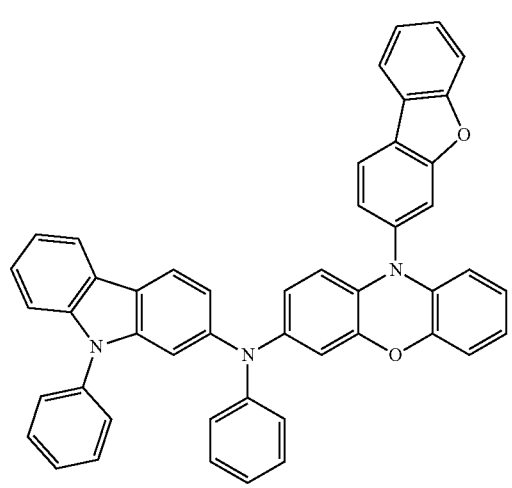
141
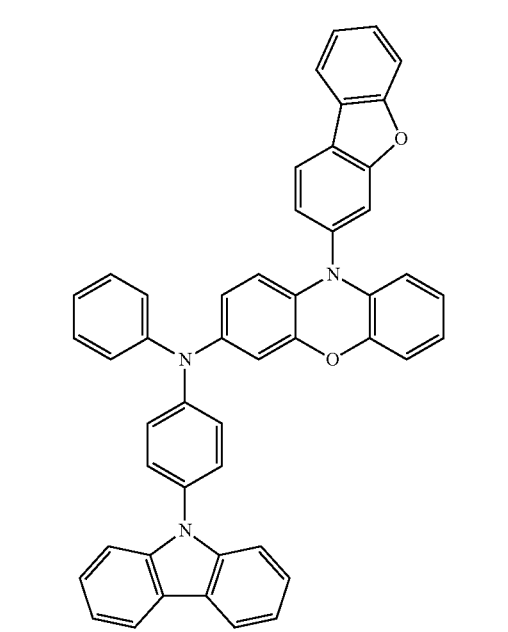
142
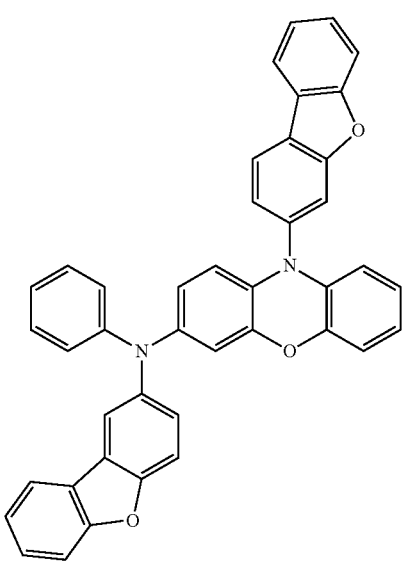
143
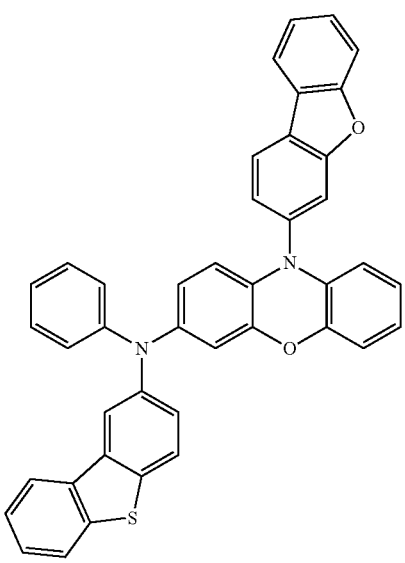
144
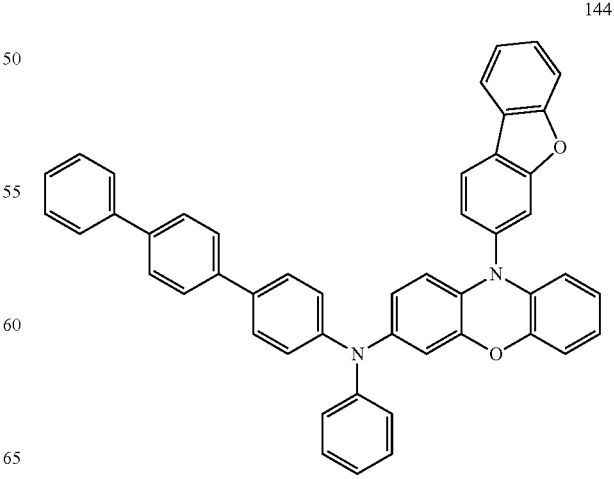

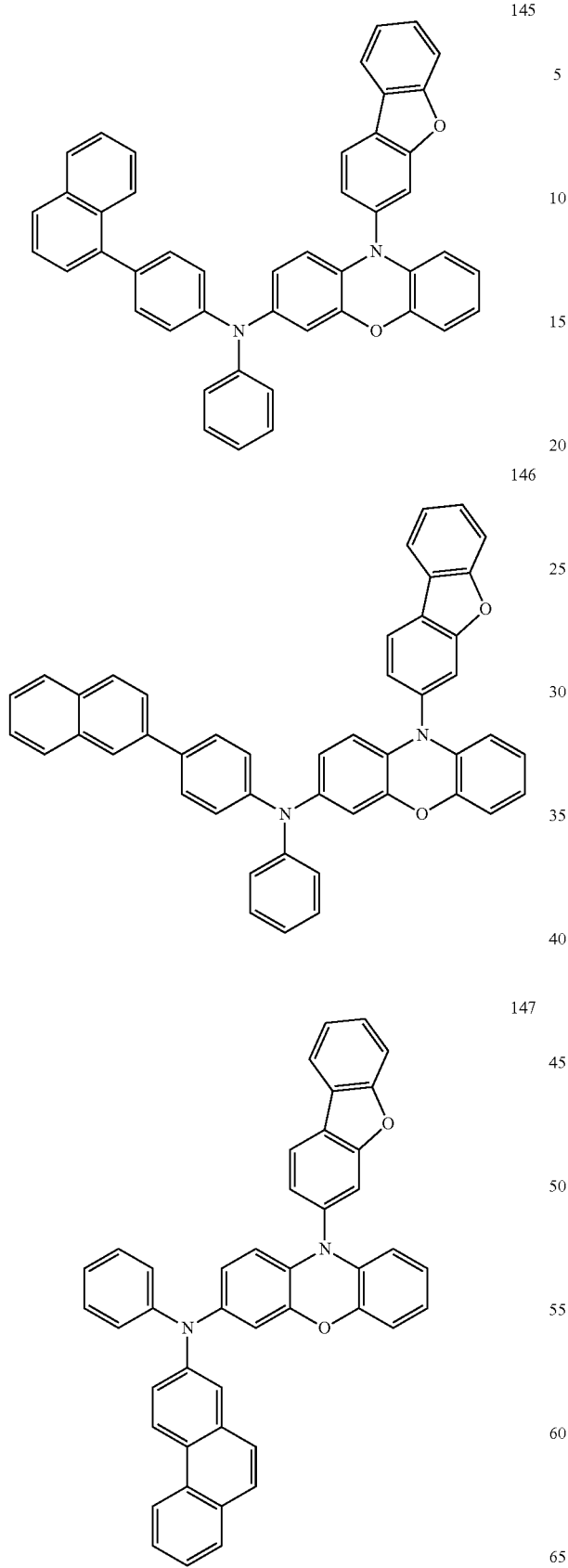
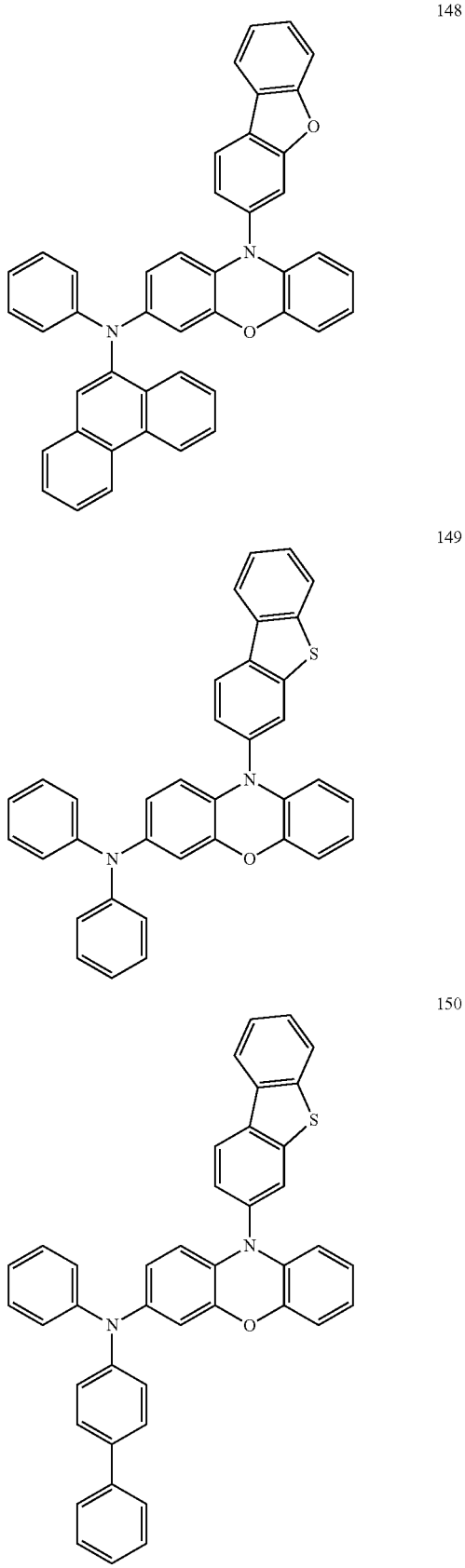 [SMILES: c1ccc(N(c2ccc3c(c2)Oc2ccccc2N3c2ccc3c(c2)oc2ccccc23)c2cc3ccccc3c3ccccc23)cc1 ; c1ccc(N(c2ccccc2)c2ccc3c(c2)Oc2ccccc2N3c2ccc3c(c2)sc2ccccc23)cc1 ; c1ccc(-c2ccc(N(c3ccccc3)c3ccc4c(c3)Oc3ccccc3N4c3ccc4c(c3)sc3ccccc34)cc2)cc1]

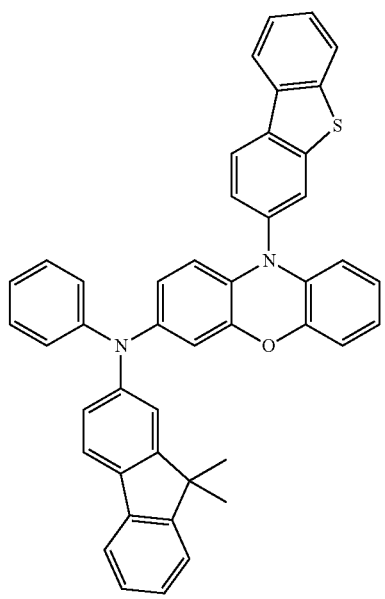
151
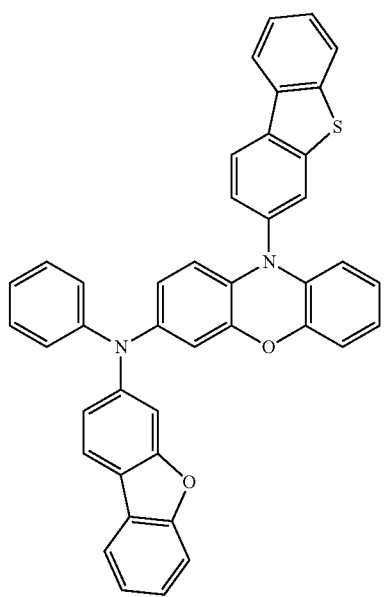
152
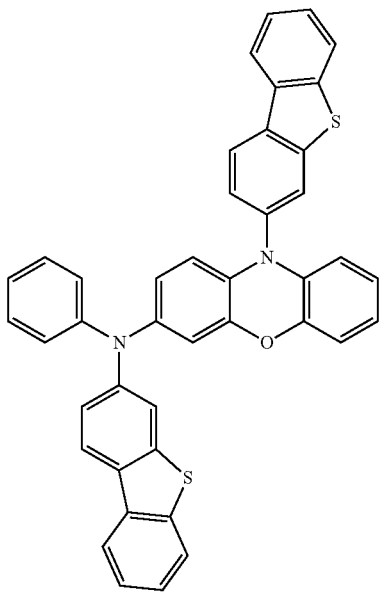
153
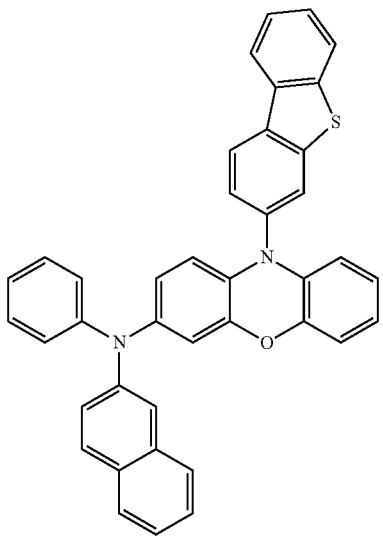
154
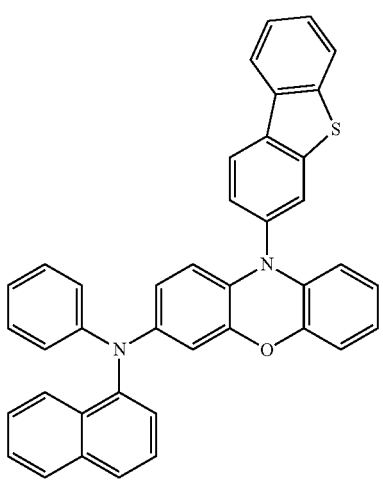
155

127
-continued
156
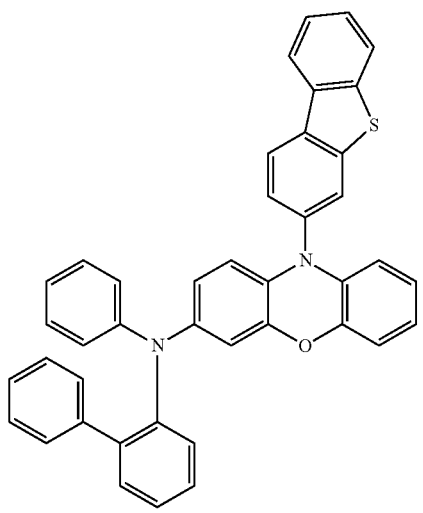
157
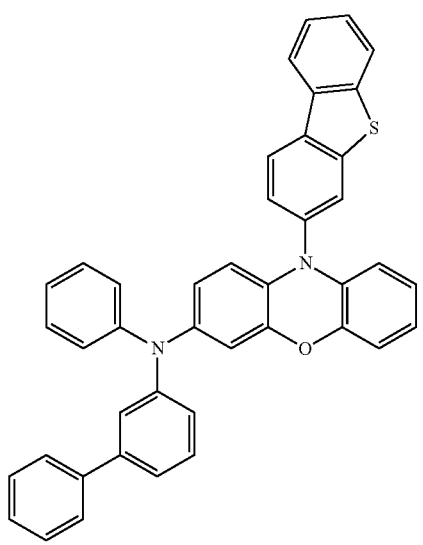
158
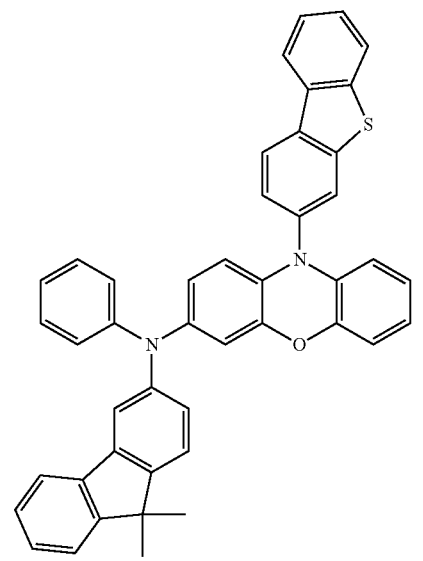
128
-continued
159
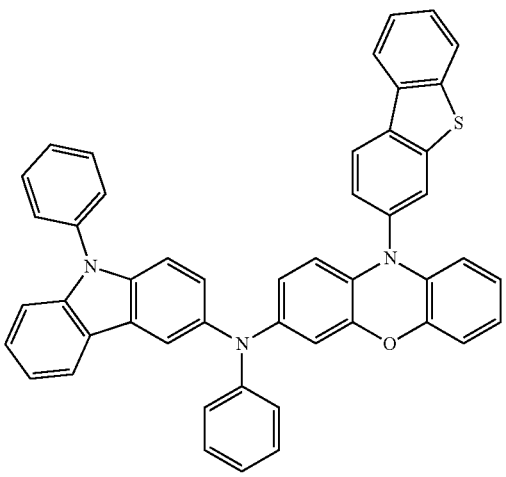
160
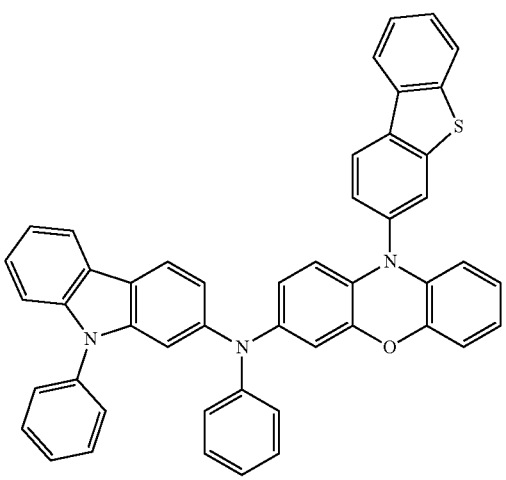
161
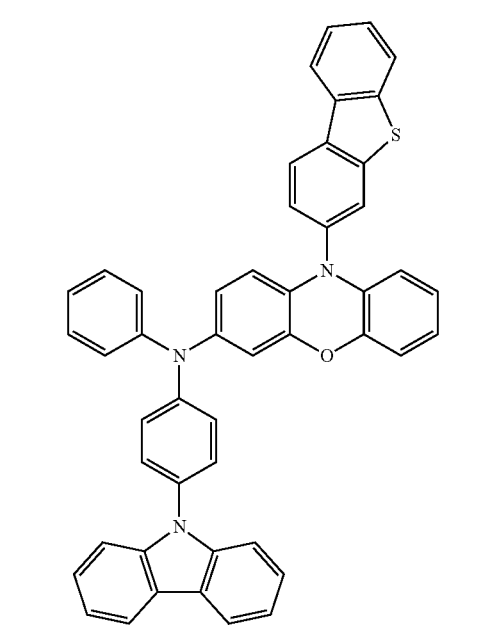

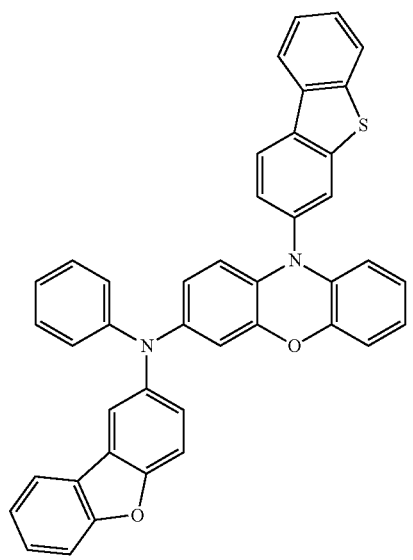
162
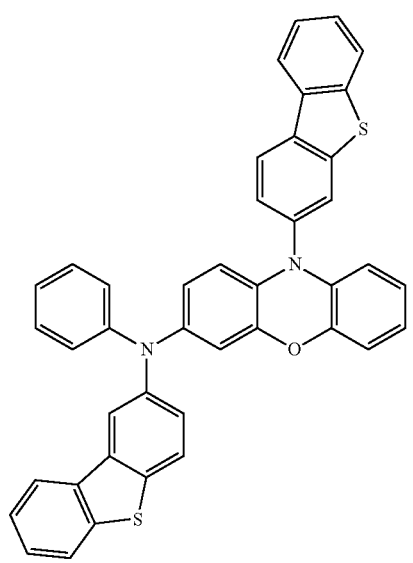
163
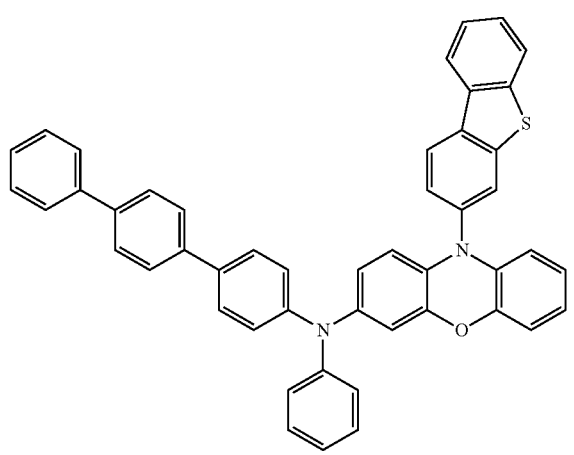
164
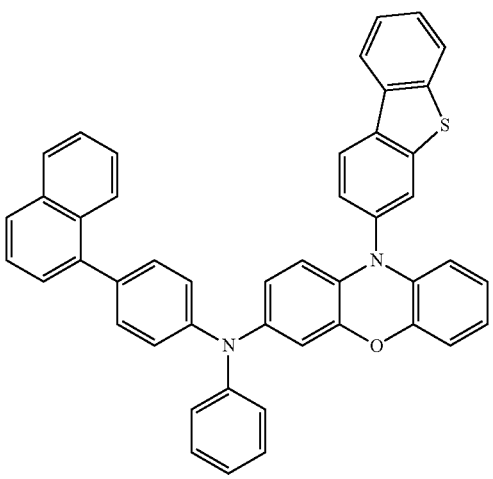
165
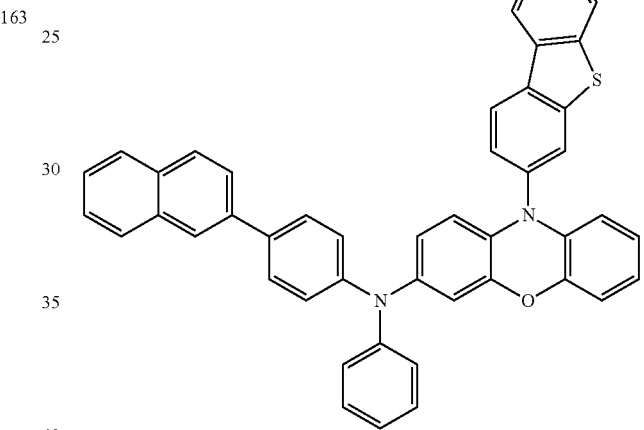
166
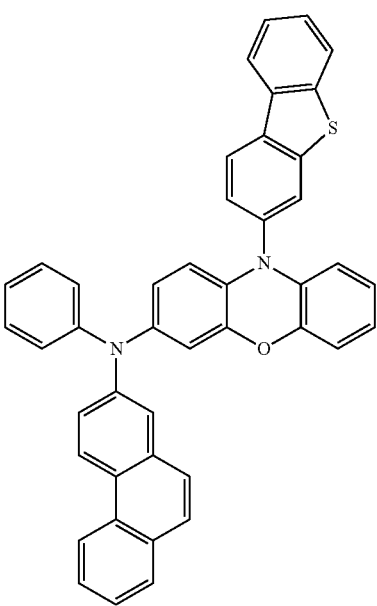
167

173
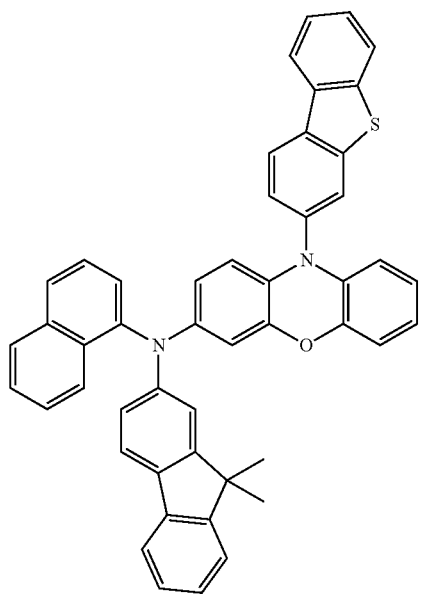
174
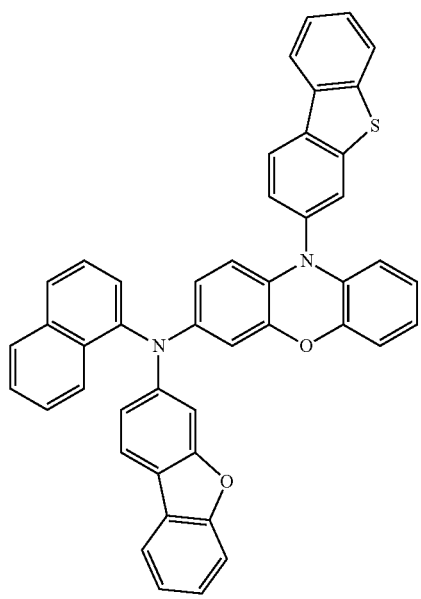
175
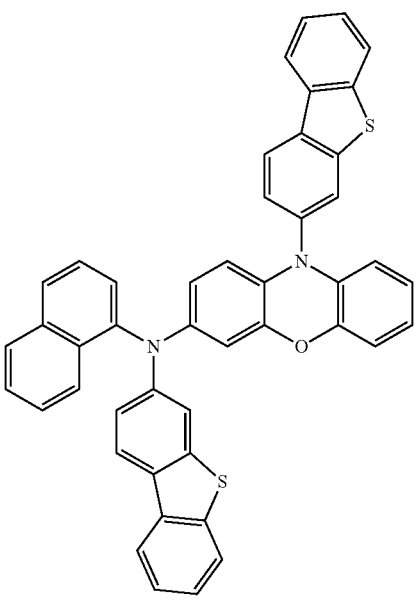
176
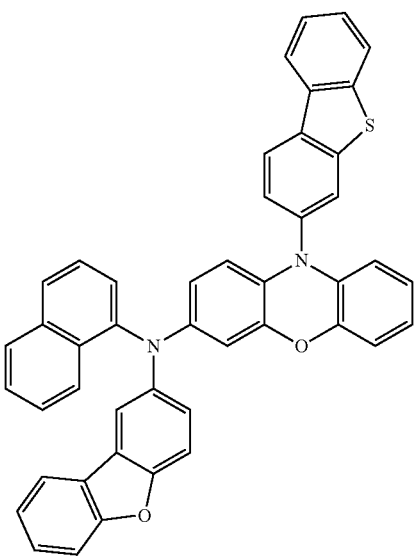

177
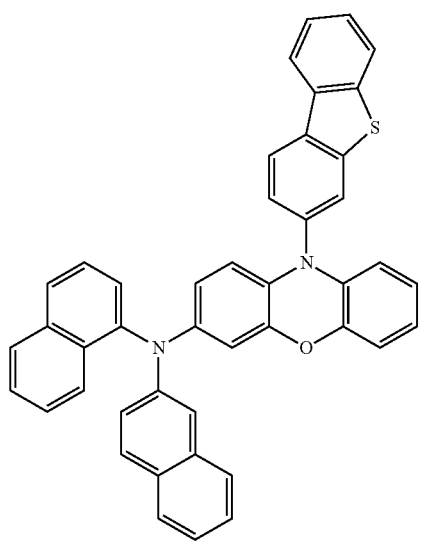
178
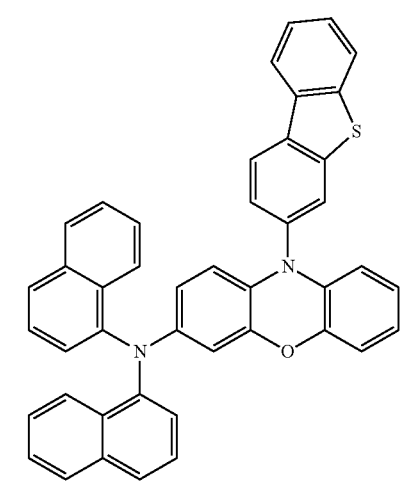
179
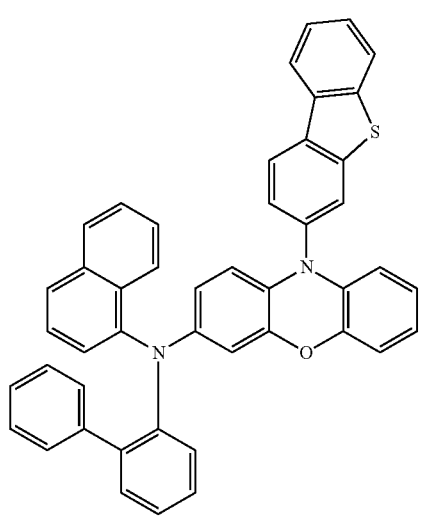
180
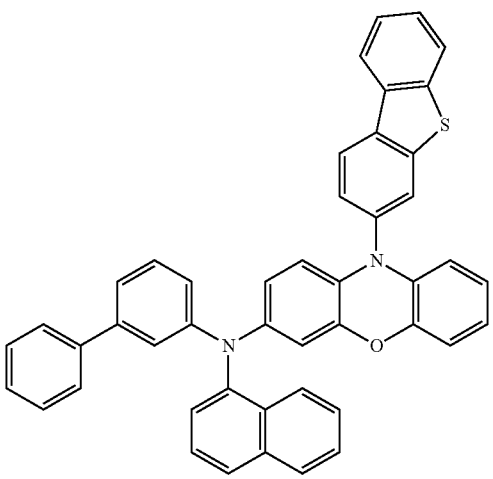
181
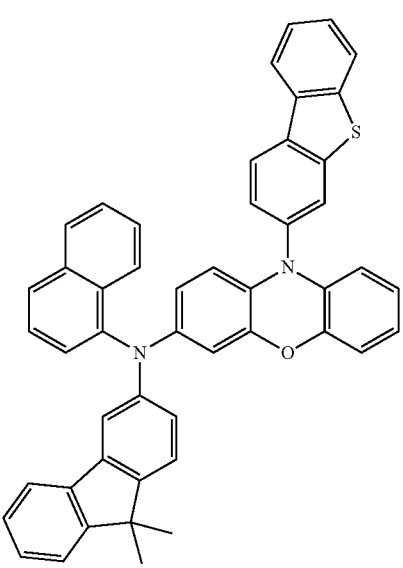
182
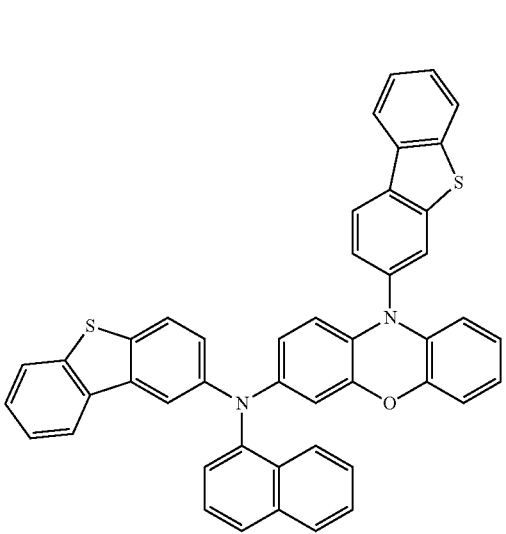

-continued
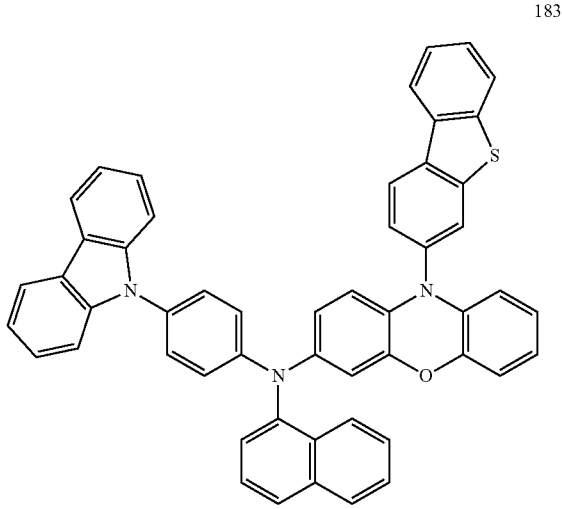
183
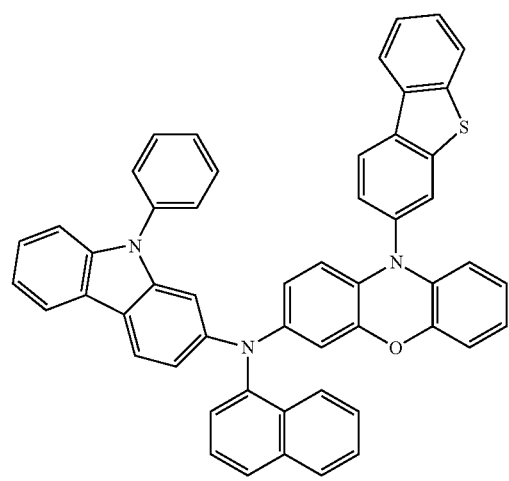
184
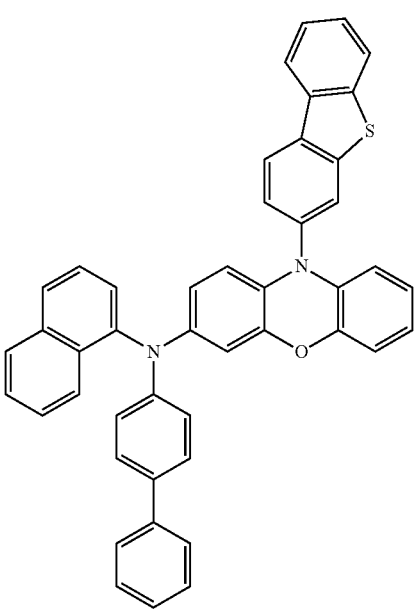
200
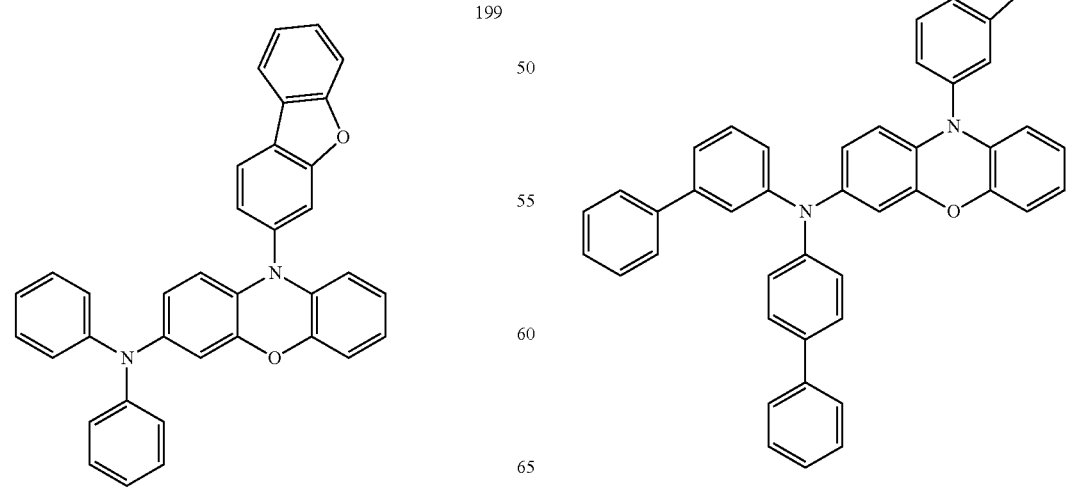

137
-continued
249
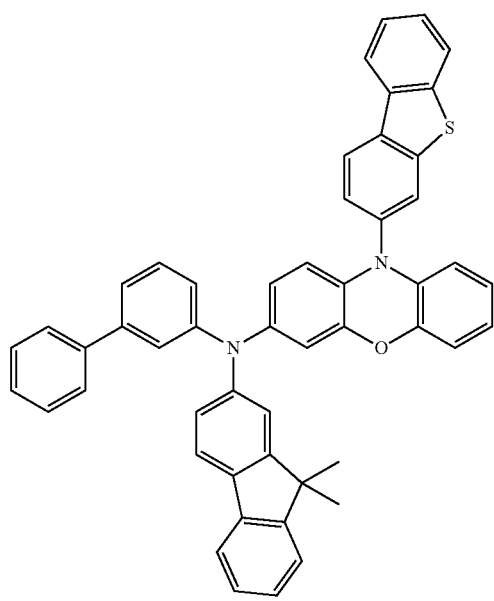
250
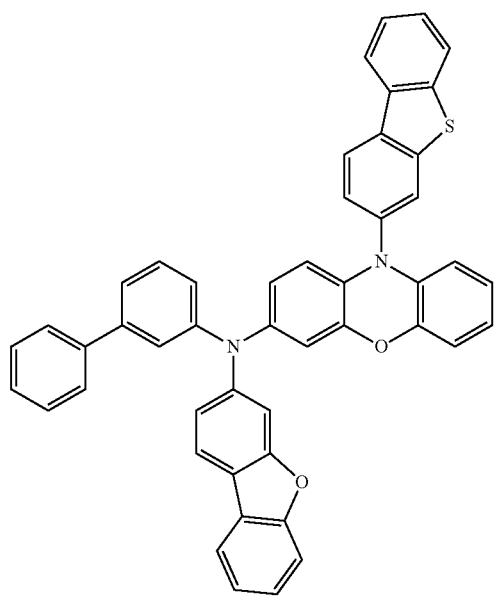
138
-continued
251
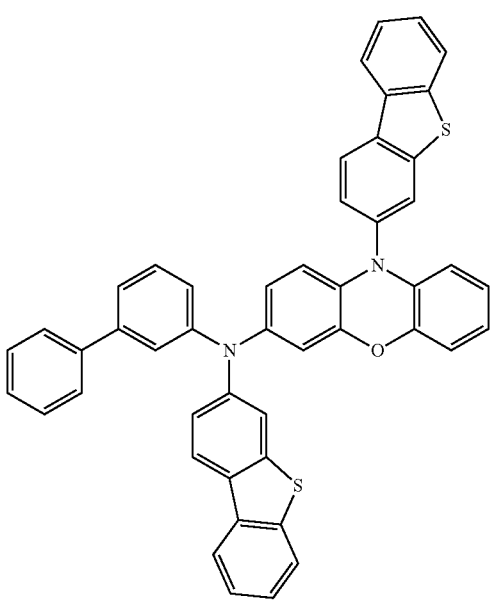
252
253

254
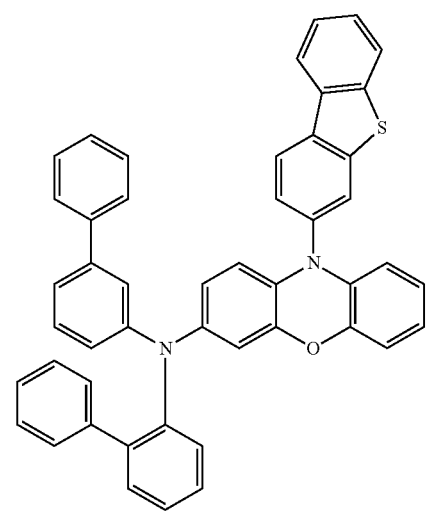
255
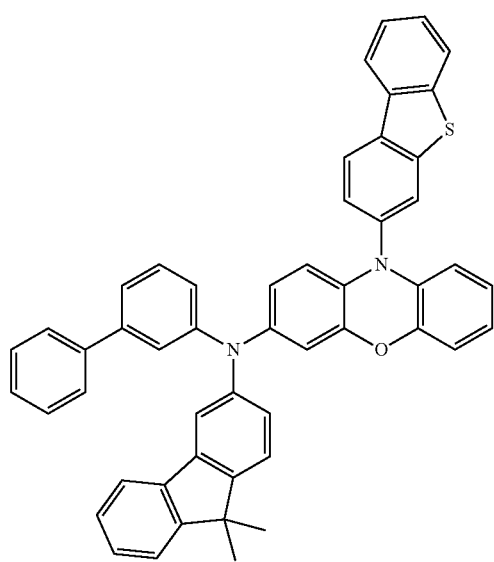
256
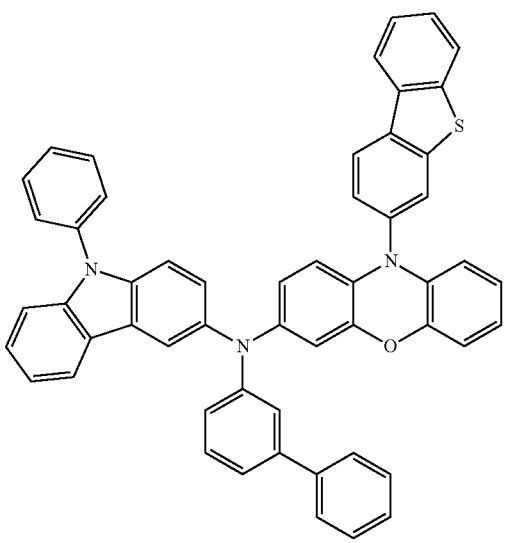
257
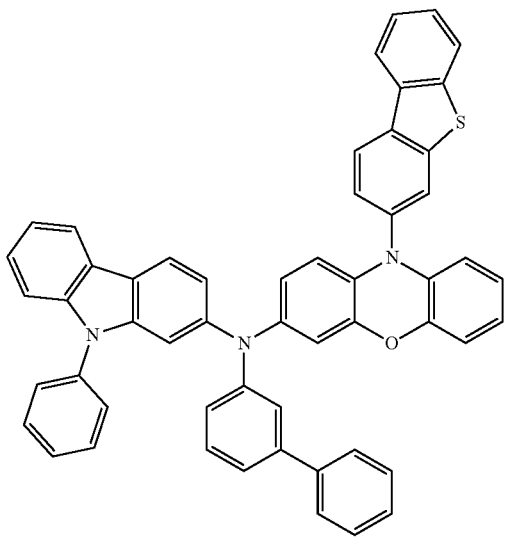
258
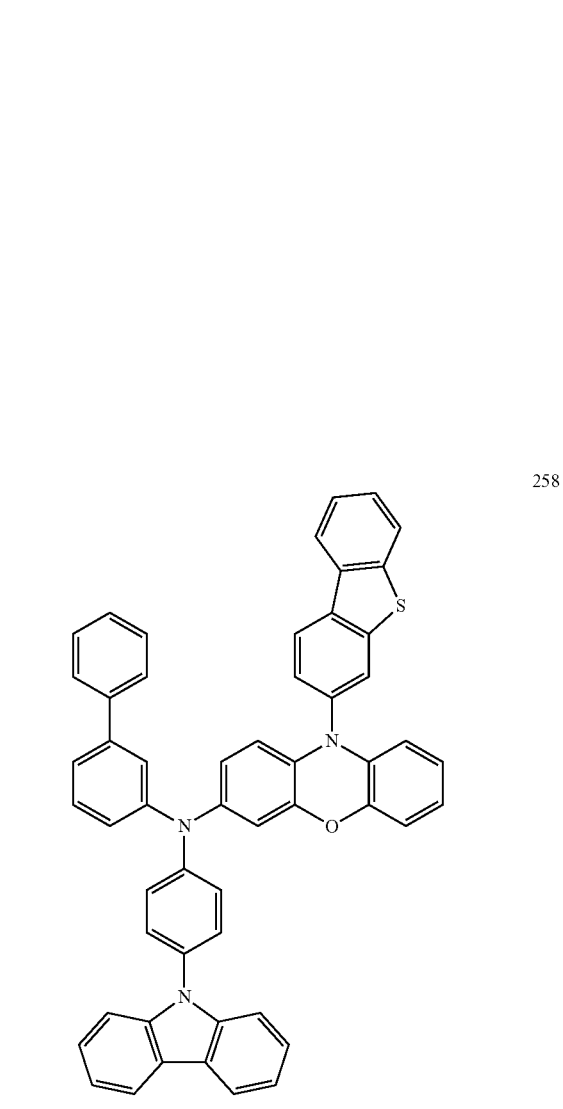

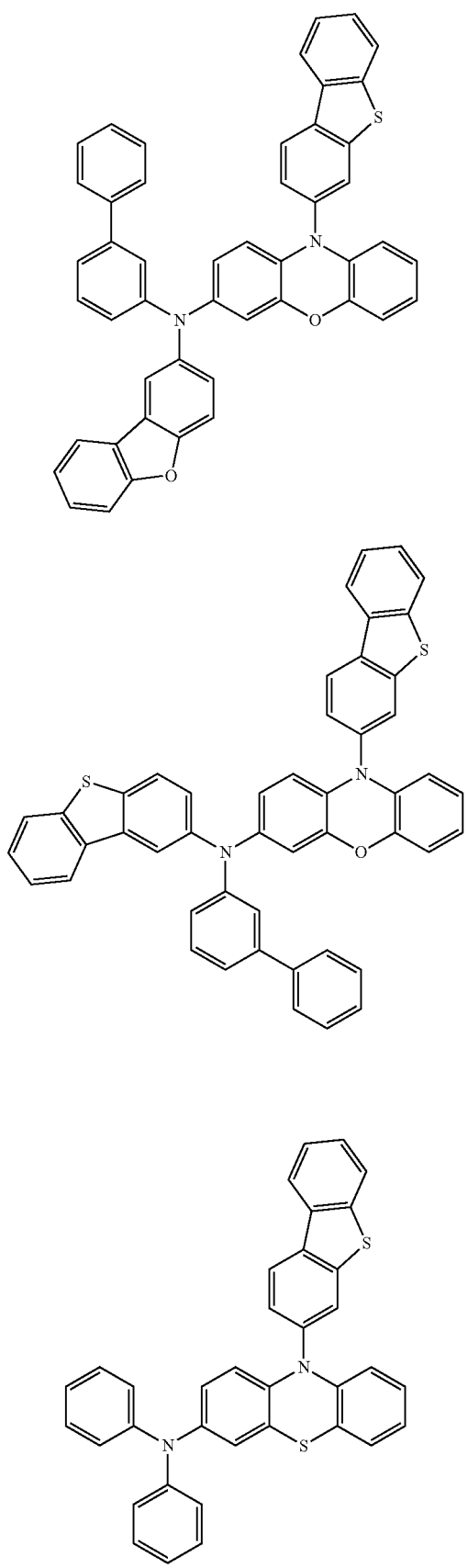

143
-continued
328
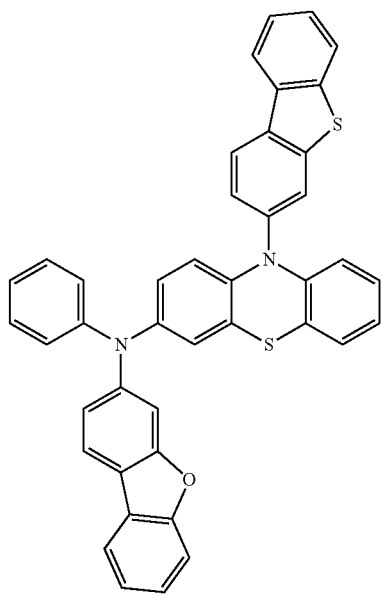
329
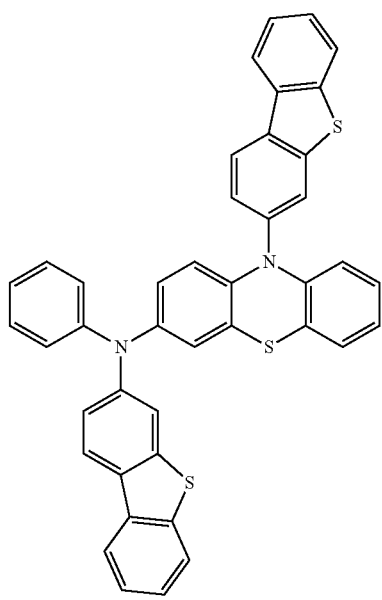
144
-continued
330
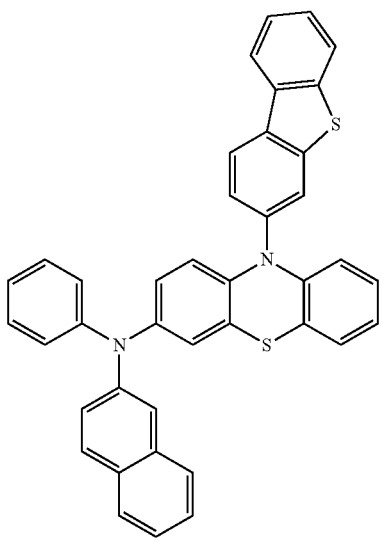
331
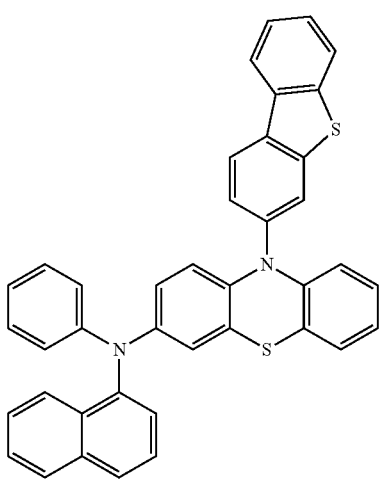
332
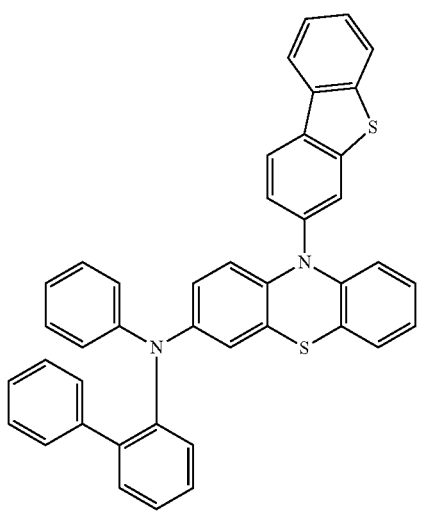

333
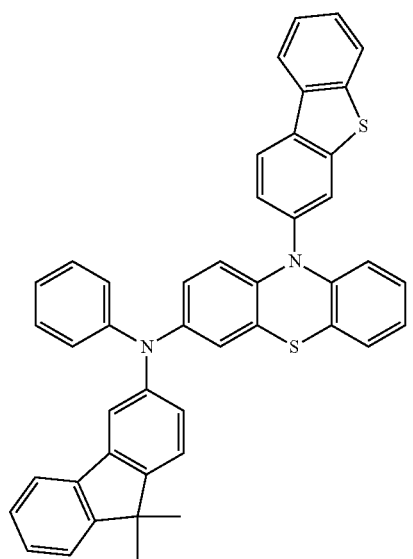
334
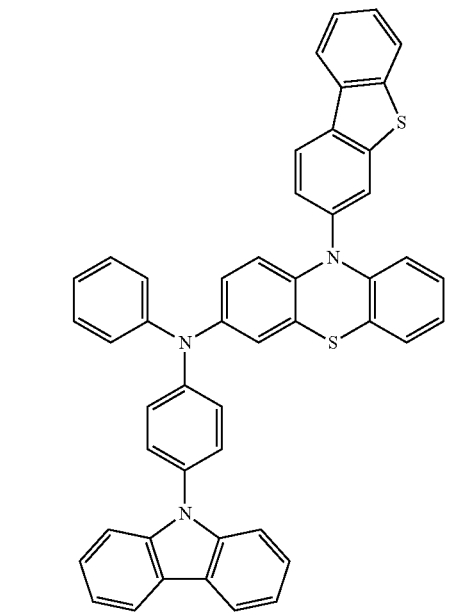
335
336
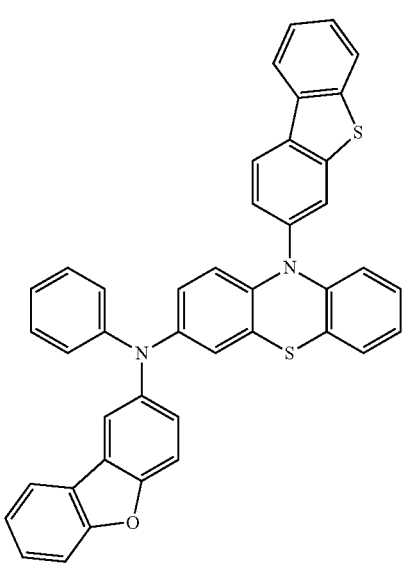
337
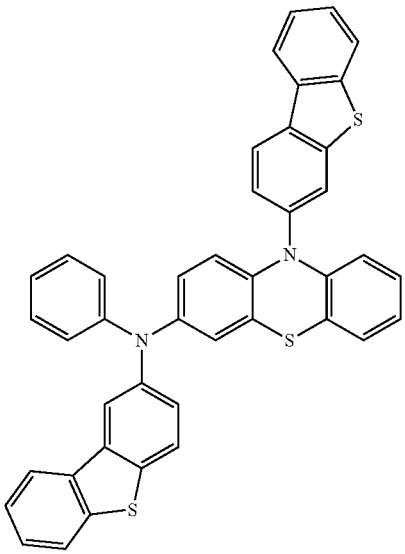

147
-continued
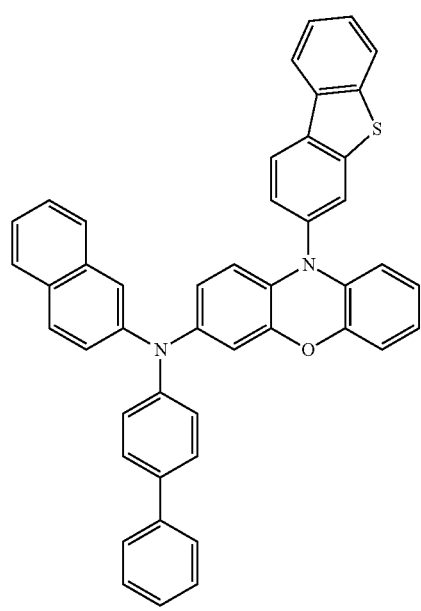
338
339
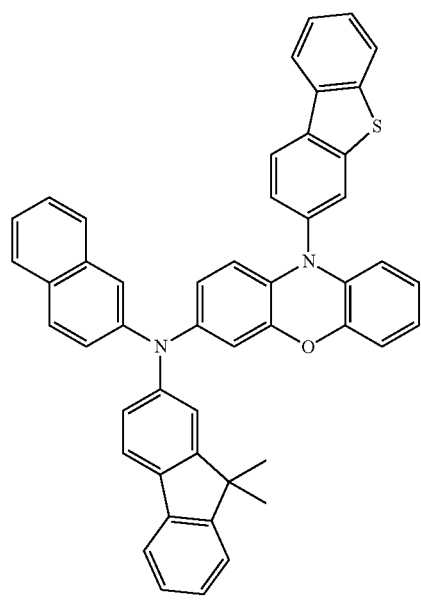
148
-continued
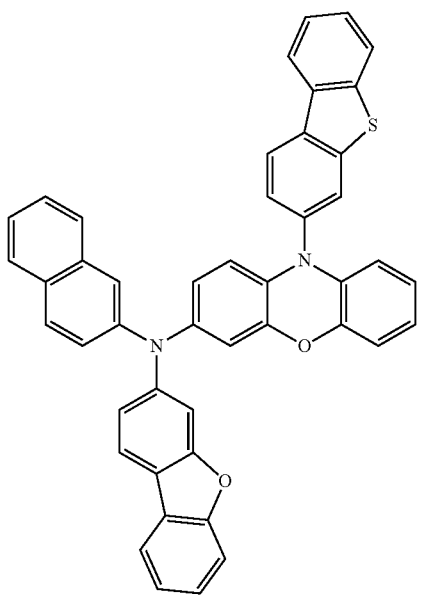
340
341
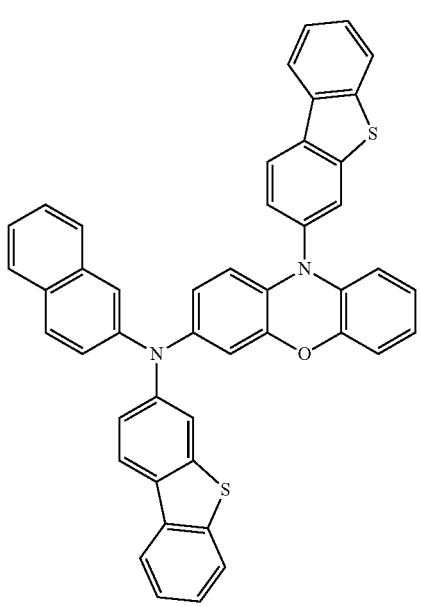

342
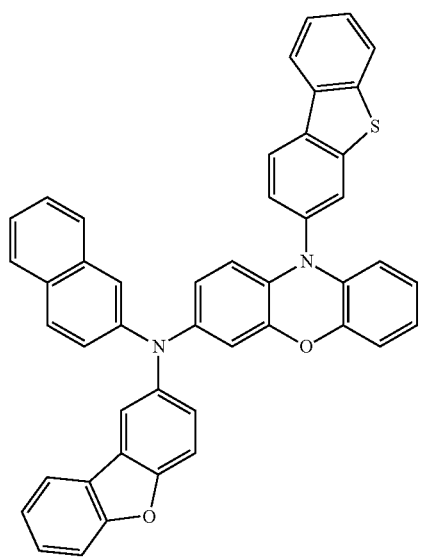
343
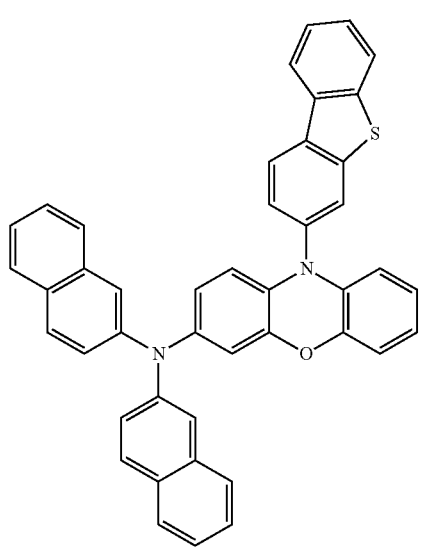
344
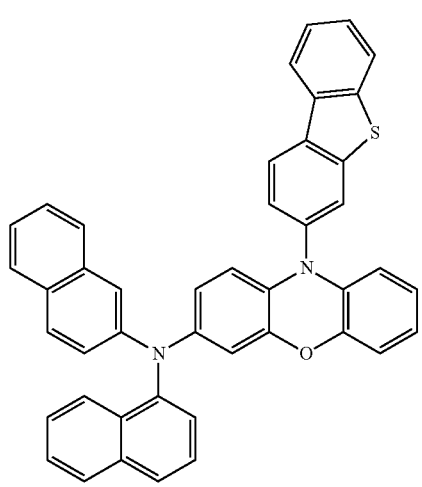
345
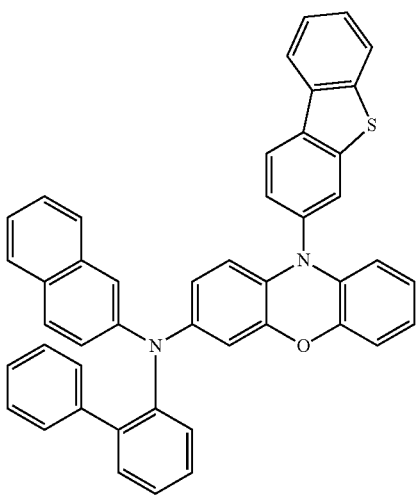
346
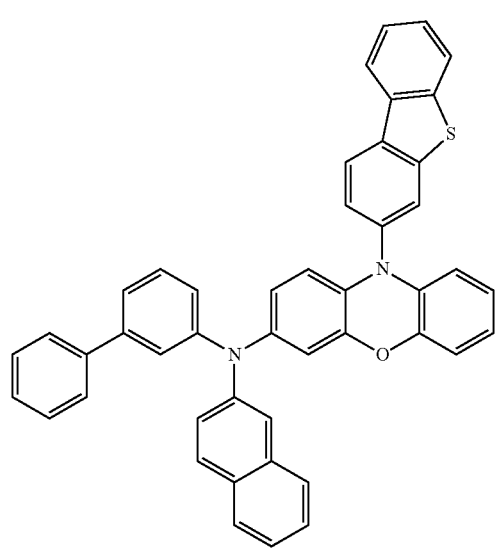
347
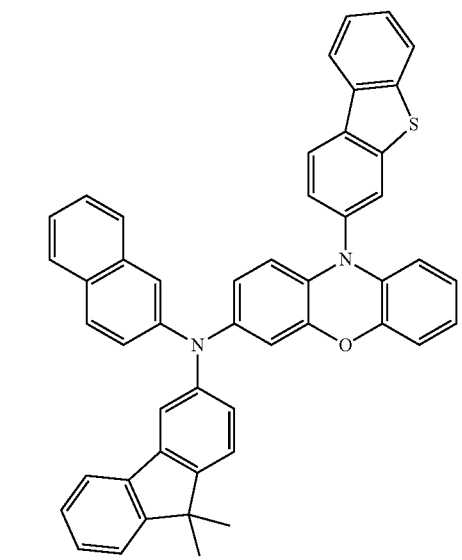

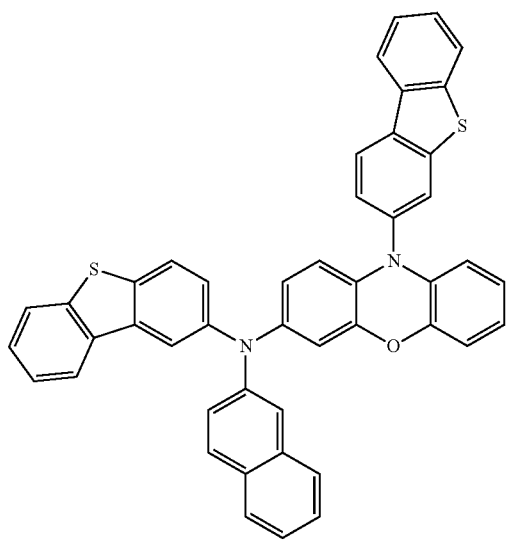
348
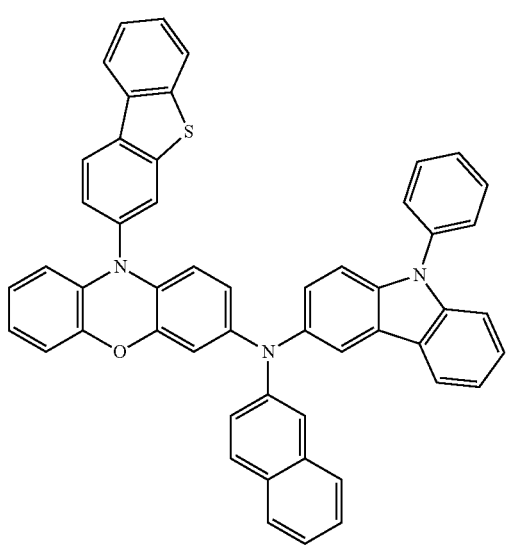
349
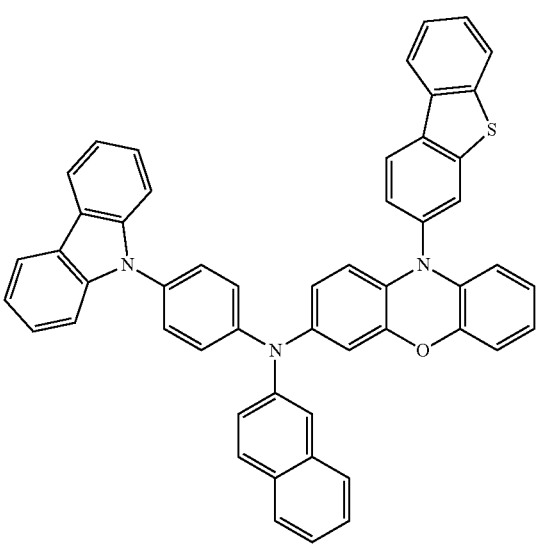
350
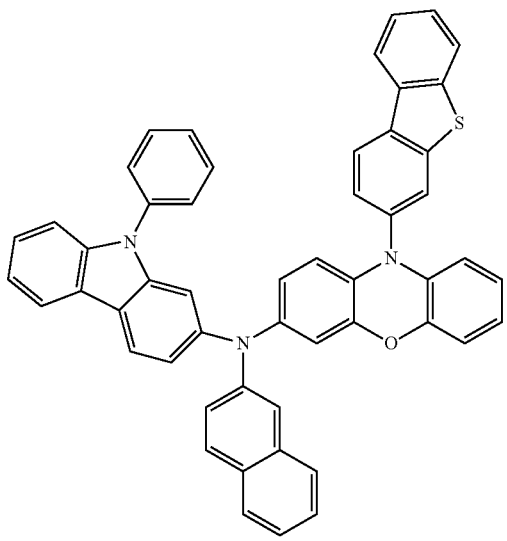
351
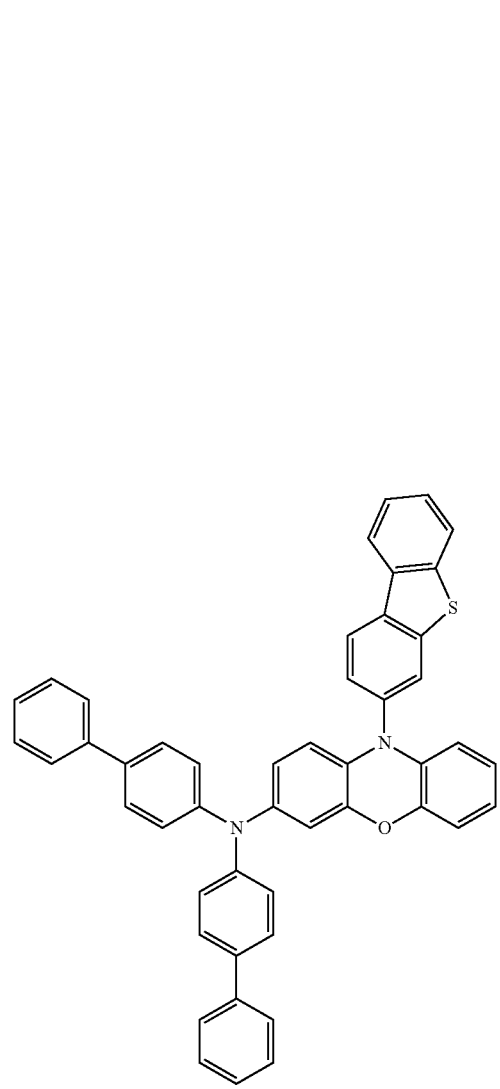
352

153
-continued
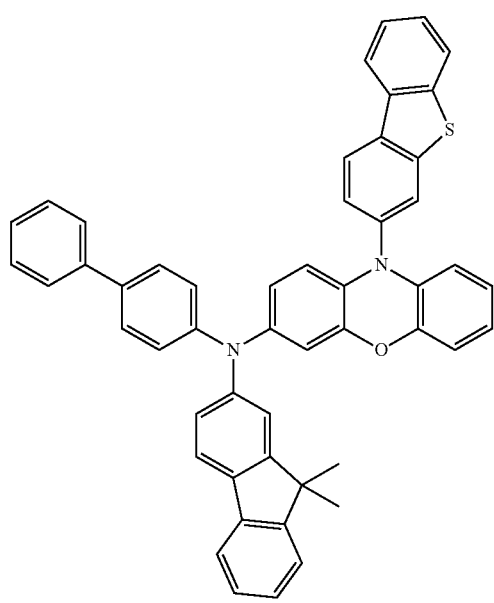
353
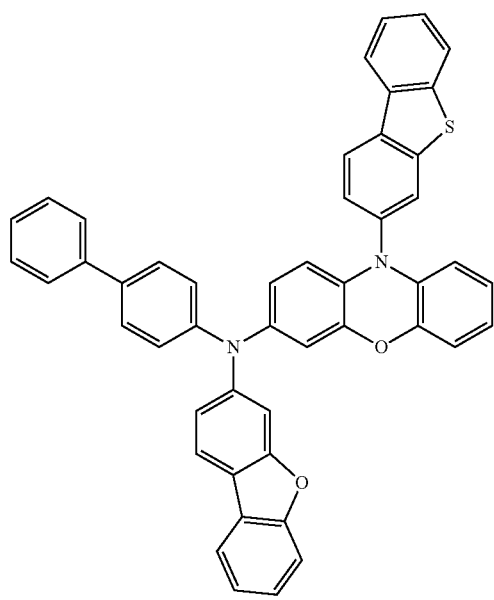
354
154
-continued
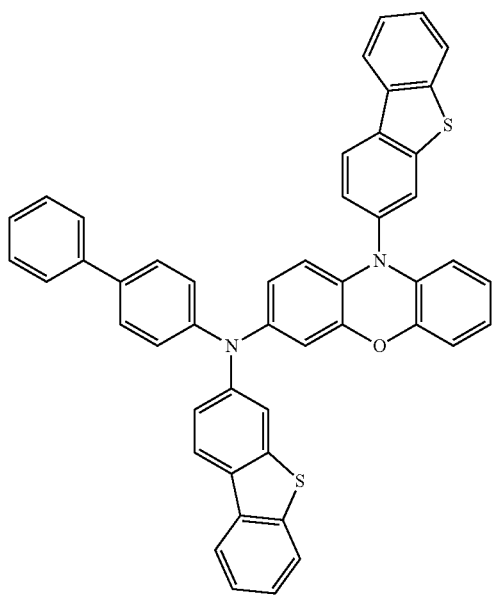
355
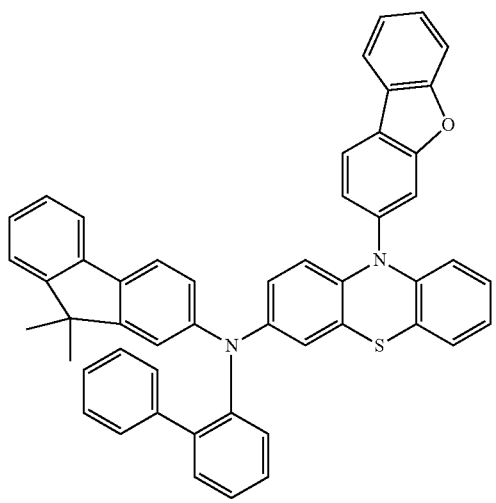
356
357

358
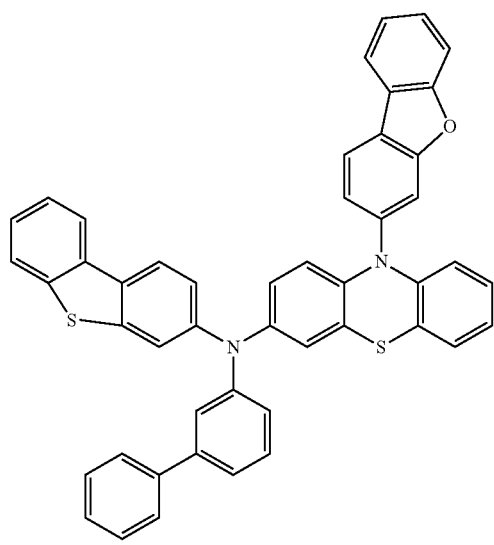
359
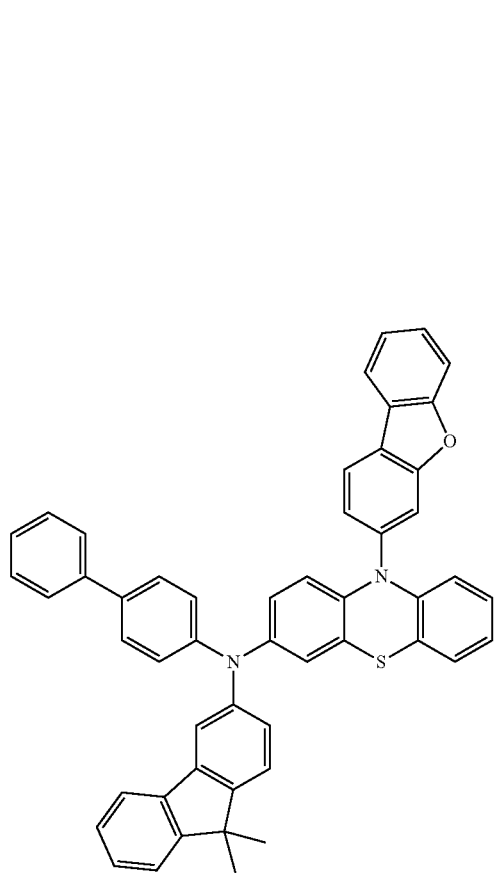
360
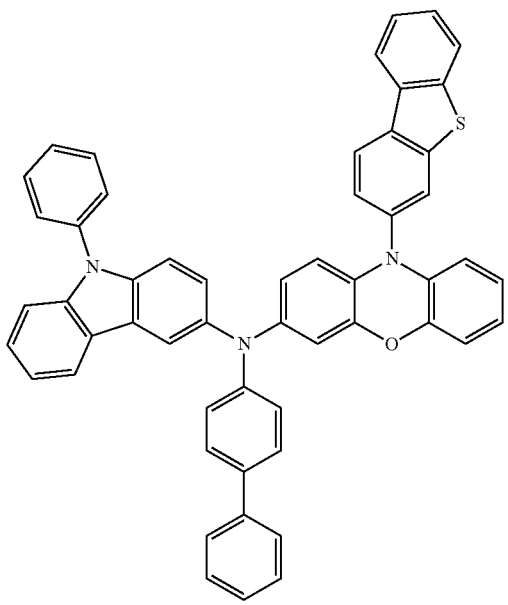
361
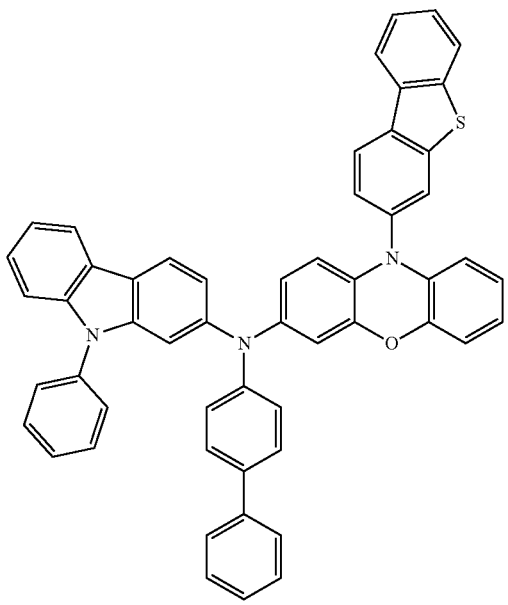

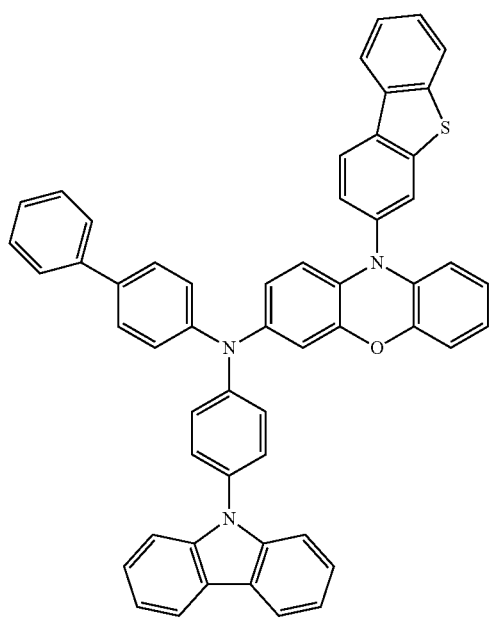
362
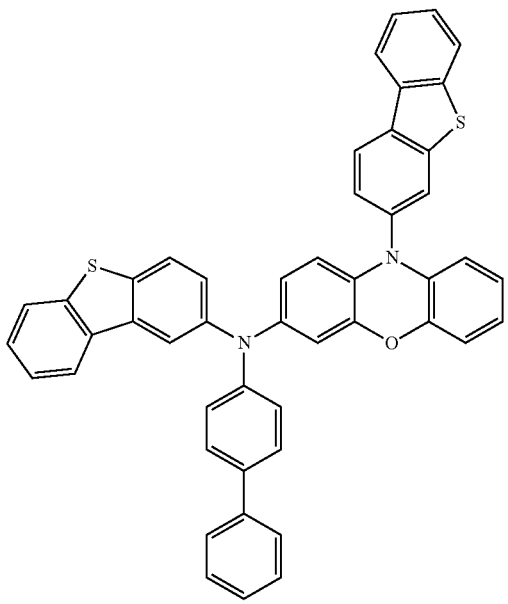
364
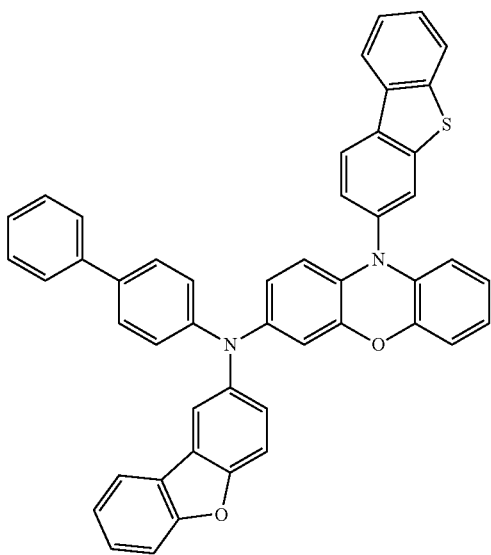
363
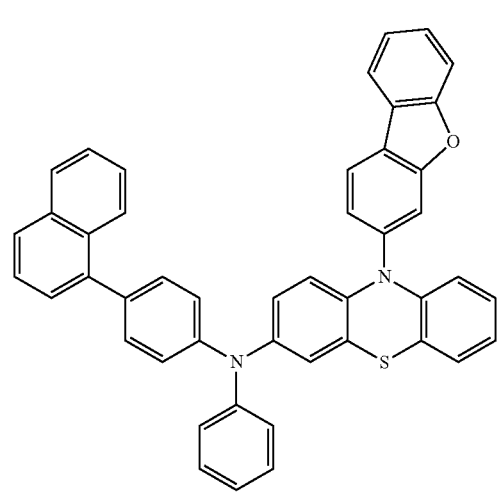
365
366

159
-continued
367
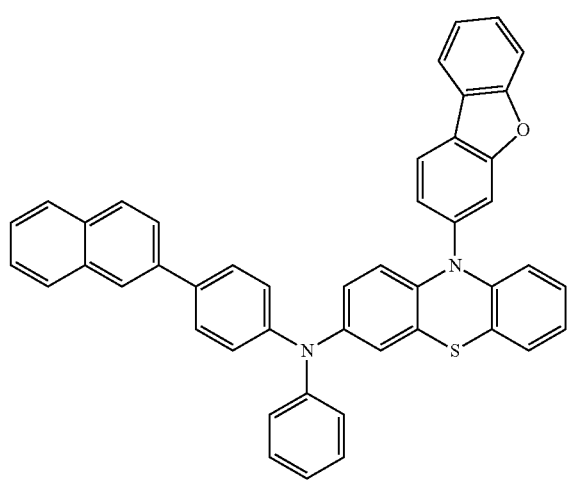
368
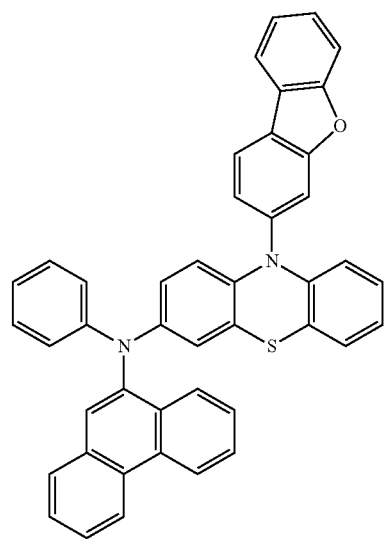
160
-continued
386
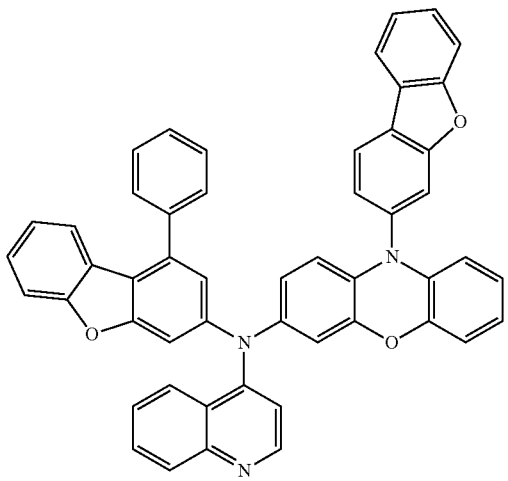
387
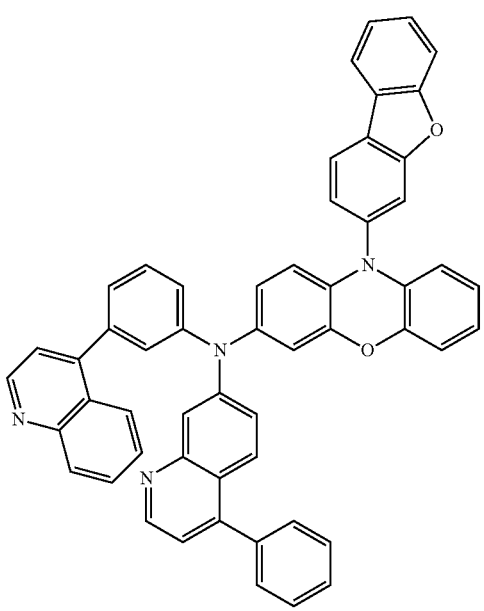

-continued

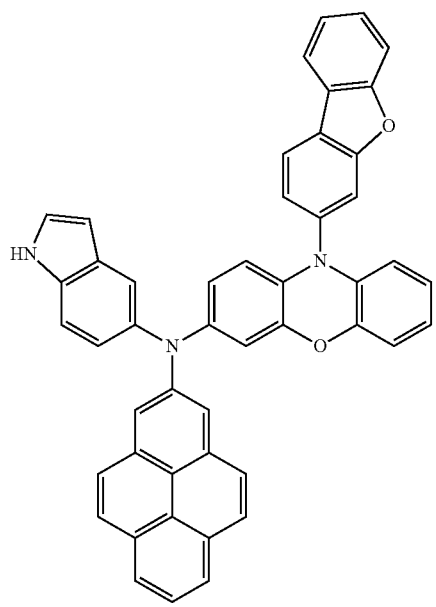

388

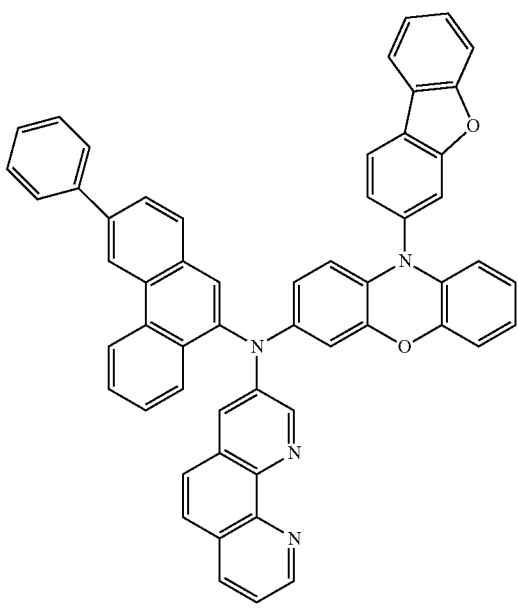

389

-continued

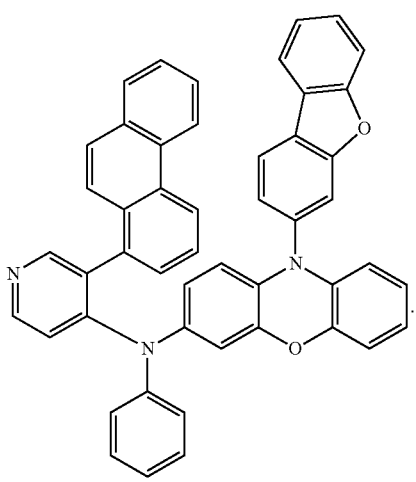

390

12. An electronic element, comprising an anode and a cathode that are arranged oppositely, and a functional layer arranged between the anode and the cathode,
wherein the functional layer comprises the nitrogen-containing compound according to claim 11.

13. The electronic element according to claim 12, wherein the functional layer comprises a hole transport layer, and the hole transport layer comprises the nitrogen-containing compound.

14. The electronic element according to claim 13, wherein the electronic element is an organic electroluminescent device or a solar cell.

15. An electronic device, comprising the electronic element according to claim 12.

* * * * *